US007347161B2

(12) United States Patent
Pratt

(10) Patent No.: US 7,347,161 B2
(45) Date of Patent: Mar. 25, 2008

(54) CATTLE MANAGEMENT METHOD AND SYSTEM

(75) Inventor: William C. Pratt, Canyon, TX (US)

(73) Assignee: Micro Beef Technologies, Ltd., Amarillo, TX (US)

( * ) Notice: Subject to any disclaimer, the term of this patent is extended or adjusted under 35 U.S.C. 154(b) by 0 days.

(21) Appl. No.: 10/903,963

(22) Filed: Jul. 30, 2004

(65) Prior Publication Data

US 2005/0000458 A1    Jan. 6, 2005

Related U.S. Application Data

(63) Continuation of application No. 10/323,115, filed on Dec. 18, 2002, now Pat. No. 6,805,075, which is a continuation of application No. 09/967,151, filed on Sep. 27, 2001, now Pat. No. 6,516,746, which is a continuation of application No. 09/426,412, filed on Oct. 25, 1999, now Pat. No. 6,318,289, which is a continuation of application No. 09/227,171, filed on Jan. 7, 1999, now Pat. No. 6,135,055, which is a continuation of application No. 08/838,768, filed on Apr. 10, 1997, now Pat. No. 6,000,361, which is a continuation of application No. 08/332,563, filed on Oct. 31, 1994, now Pat. No. 5,673,647.

(51) Int. Cl.
*A01K 5/00* (2006.01)

(52) U.S. Cl. .................................. 119/51.02

(58) Field of Classification Search ............. 119/51.02, 119/502, 511, 840, 841, 842; 348/89; 452/52, 452/53

See application file for complete search history.

(56) References Cited

U.S. PATENT DOCUMENTS 2,786,449 A    3/1957  Dahlerup (Continued)

FOREIGN PATENT DOCUMENTS

EP    0945060 A2 *  3/1999

(Continued)

OTHER PUBLICATIONS

"Answer to Request No. 20—List of Patents, Articles, and other prior art references," Fax Transmission from Mullin, Hoard & Brown to Klarquist Sparkman, 12 pp. (Dec. 2001).

(Continued)

*Primary Examiner*—Thomas Price
(74) *Attorney, Agent, or Firm*—Klarquist Sparkman LLP

(57) ABSTRACT

A highly automated method and system for providing individual animal electronic identification, measurement and value based management of cattle in a large cattle feedlot. Through the use of (1) a computer system integrated with (2) automatic individual animal identification (3) multiple measurement and remeasurement systems with automatic data input and (4) a cattle handling and sorting system, animals are individually (a) identified and (b) measured by weight, external dimensions and characteristics of internal body tissue. With this information together with animal physiological characteristics and historical data, the computer system calculates the optimum (c) slaughter weight, (d) economic end point and (e) marketing date for shipment to a packing plant. After measurement, individual animals are (f) sorted by direction of the computer in response to calculations from the measurements. The computer system also calculates from individual animal data and other data (g) each animal's pro rata share of total feed intake for the animal's feed group. The computer system (h) stores individual animal measurement, performance and location data, which is used by management to (i) select animals for shipment from the feedlot for slaughter at the optimum time. Following an animal's shipment to a slaughter facility, its identification in the computer system is used to (j) correlate the live animal physical characteristics and performance data to the measured and evaluated carcass characteristics data obtained during the slaughter process and (k) build a data base to more accurately identify and measure value-based characteristics in subsequent animals produced and fed for more effective value-based selection and management of those animals.

6 Claims, 34 Drawing Sheets

U.S. PATENT DOCUMENTS

| | | | |
|---|---|---|---|
| 2,891,722 | A | 6/1959 | Nuttall |
| 3,077,861 | A | 2/1963 | Eide |
| 3,465,724 | A | 9/1969 | Broadbent |
| 3,545,407 | A | 12/1970 | Moore |
| 3,848,112 | A | 11/1974 | Weichselbaum et al. |
| 3,929,277 | A | 12/1975 | Byrne et al. |
| 4,049,950 | A | 9/1977 | Byrne et al. |
| 4,129,096 | A | 12/1978 | Nickel |
| 4,135,241 | A | 1/1979 | Stanis et al. |
| 4,280,448 | A | 7/1981 | Ostermann |
| 4,288,856 | A | 9/1981 | Linseth |
| 4,336,589 | A | 6/1982 | Smith et al. |
| 4,461,240 | A | 7/1984 | Ostler |
| 4,461,241 | A | 7/1984 | Ostler |
| 4,463,706 | A | 8/1984 | Meister et al. |
| 4,517,923 | A | 5/1985 | Palmer |
| 4,589,372 | A | 5/1986 | Smith |
| 4,617,876 | A | 10/1986 | Hayes |
| 4,687,107 | A | 8/1987 | Brown et al. |
| 4,712,511 | A | 12/1987 | Zamzow et al. |
| 4,733,971 | A | 3/1988 | Pratt |
| 4,745,472 | A | 5/1988 | Hayes |
| 4,767,212 | A | 8/1988 | Kitahashi et al. |
| 4,786,925 | A | 11/1988 | Landwehr |
| 4,815,042 | A | 3/1989 | Pratt |
| 4,889,433 | A | 12/1989 | Pratt |
| 4,910,024 | A | 3/1990 | Pratt |
| 4,939,574 | A | 7/1990 | Petersen et al. |
| 4,963,035 | A | 10/1990 | McCarthy et al. |
| 5,008,821 | A | 4/1991 | Pratt et al. |
| 5,028,918 | A | 7/1991 | Giles et al. |
| 5,164,793 | A | 11/1992 | Wolfersberger et al. |
| 5,184,733 | A | 2/1993 | Arnarson et al. |
| 5,194,036 | A | 3/1993 | Chevalier et al. |
| 5,219,224 | A | 6/1993 | Pratt |
| 5,241,365 | A | 8/1993 | Haagensen |
| 5,315,505 | A | 5/1994 | Pratt et al. |
| 5,340,211 | A | 8/1994 | Pratt |
| 5,351,644 | A | 10/1994 | Everett |
| 5,673,647 | A | 10/1997 | Pratt |
| 6,000,361 | A | 12/1999 | Pratt |
| 6,516,746 | B2 | 2/2003 | Pratt |

FOREIGN PATENT DOCUMENTS

| | | |
|---|---|---|
| SU | 1704730 | 1/1992 |

OTHER PUBLICATIONS

"Articles Received from Future Beef," pp. 1-5.
"Cattle Scanning Systems," Rapid City, South Dakota, 2 pp. (undated).
"Executive Summary National Beef Quality Audit," Published by the National Cattlemen's Association in Coordination with Colorado State University and Texas A&M University, 24 pp. (1992) (month not in issue, year sufficiently early—"the year of publication [without the month] will be accepted if the applicant points out in the information disclosure statement that the year of publication is sufficiently earlier than the effective U.S. filing date and any foreign priority date so that the particular month of publication is not in issue" MPEP 609).
"XIIIth World Congress on Diseases of Cattle," World Buiatrics Association, Proceedings vol. 1 (Sep. 1984).
Abdullah et al., "Relationships between objective and subjective measurements of carcass muscularity," Proceedings of the New Zealand Society of Animal Production, vol. 53, pp. 397-402 (1993) (month not in issue, year sufficiently early).
Abraham et al., "Factors Affecting Beef Carcass Cutability: An Evaluation of the USDA Yield Grades for Beef," *J. Animal Science*, 50:841-851 (1980) (month not in issue, year sufficiently early).
Allen et al., "Relationship of physically separable muscle, fat and bone from the left side of steer carcasses to yields of retail cuts, fat trim and bone of the right side," pp. 311-315 (Circa more than one year prior to Oct. 31, 1994).
Article from *Feed Management*, vol. 36, No. 3, pp. 55-58 (Mar. 1985).
Aughtry, *SMS Feedlot Management System*, and attachments (54 pp.). At least one copy has been distributed, on a nonconfidential basis, at least as early as (Jun. 1986).
Barber et al., "Charolais and angus steers slaughtered at equal percentages of mature cow weight. I. Effects of slaughter weight and diet energy density of carcass traits," pp. 218-230 (Circa more than one year prior to Oct. 31, 1994).
Beltran et al., "Growth Patterns of Two Lines of Angus Cattle Selected Using Predicted Growth Parameters," *J. Animal Science*, 70:734-741 (1992) (month not in issue, year sufficiently early).
Bishop et al., "Divergent Selection of Postweaning Feed Conversion in Angus Beef Cattle: I. Mean Comparisons," *J. Animal Science*, 69:4348-4359 (1991) (month not in issue, year sufficiently early).
Bond et al., "Effects of Feeding Level on Growth, Composition of Gain, Carcass Quality and Mature Body Size in Steers at Ages up to Six Years," *Growth*, pp. 388-403 (1982) (month not in issue, year sufficiently early).
Brackebusch et al., "Relationship Between Longissimus Composition and the Composition of Other Major Muscles of the Beef Carcass," *J. Animal Science*, 69:631-640 (1991) (month not in issue, year sufficiently early).
Brethour, "Estimating Marbling Score in Live Cattle from Ultrasound Images Using Pattern Recognition and Neural Network Procedures," [Fort Hays Branch Experiment Station] Kansas State University, Fort Hays Branch Experiment Station (Circa more than one year prior to Oct. 31, 1994).
Brethour, "Quality Management in the Cattle Industry," *KAES Report of Progress No. 653*, Fort Hays Branch Experiment Station, Kansas State University, pp. 1-25 (Apr. 1992).
Brethour, "Relationship of Ultrasound-Measured Backfat to Feedlot Performance of Beef Steers," *KAES Report of Progress No. 627*, Fort Hays Branch Experiment Station, Kansas State University, pp. 1-30 (Apr. 1991).
Brethour, "Technology to Implement Quality into Beef Production," *KAES Report of Progress No. 706*, Fort Hays Branch Experiment Station, Kansas State University, pp. 13-17 (Circa more than one year prior to Oct. 31, 1994) (Circa more than one year prior to Oct. 31, 1994).
Brethour, "Using Ultrasound Technology to Increase Cattle Feeding Profits," *KAES Report of Progress No. 570*, Fort Hays Branch Experiment Station, Kansas State University, pp. 5-12 (Apr. 1989).
Brown and Shrode, "Body Measurements of Beef Calves and Traits of Their Dams to Predict Calf Performance and Body Composition as Indicated By Fat Thickness and Condition Score," *J. Animal Science*, 33:7-12 (1971) (month not in issue, year sufficiently early).
Brown et al., "Evaluating Relationships Among Immature Measures of Size Shape and Performance of Beef Bulls, II. The Relationships Between Immature Measures of Size, Shape and Feedlot Traits in Young Beef Bulls," *J. Animal*

*Science*, 36:1021-1031 (1973) (month not in issue, year sufficiently early).
Busch et al., "Body Measurements, Subjective Scores and Estimates of Certain Carcass Traits as Predictors of Edible Portion in Beef Cattle," pp. 557-556 (Circa more than one year prior to Oct. 31, 1994).
Butcher and Webb, "Equipment for Farm Use in the National Cooperative Dairy Herd Improvement Program," National Cooperative Dairy Herd Improvement Program Handbook (1985) (month not in issue, year sufficiently early).
Butts et al., "Relationships Among Definable Characteristics of Feeder Calves, Subsequent Performance and Carcass Traits. I. Objective Measurements," *J. Animal Science*, 51:1297-1305 (1980) (month not in issue, year sufficiently early).
Butts et al., "Relationships Among Definable Characteristics of Feeder Calves, Subsequent Performance and Carcass Traits. II. Subjective Scores," *J. Animal Science*, 51:1306-1313 (1980) (month not in issue, year sufficiently early).
Clayton, "Prediction of Feedlot Characteristics and Carcass Characteristics Using Feeder Cattle Traits," Thesis, Colorado State University (1982) (month not in issue, year sufficiently early).
Coleman et al., "Body and Carcass Composition of Angus and Charolais Steers as Affected by Age and Nutrition," *J. Animal Science*, 71:86-95 (1993) (month not in issue, year sufficiently early).
Corah et al., "Feeding Your Cows by Body Condition", November Kansas State University [Agricultural Experiment Station and Cooperative Extension Services] (1991) (month not in issue, year sufficiently early).
Cornett, "Sorting By Computer Eye: System measures body so arrivals can be grouped to hit carcass specs." *Beef*, pp. 74-78 (Apr. 1994).
Cornett, S., "The New Tools—Sorting By Computer Eye," *Beef*, pp. 74, 76, 78, (Apr. 1994).
Crouse et al., "Prediction of Feeder Calf Performance and Subsequent Carcass Characteristics," *J. Animal Science*, 38:256-263 (1974) (month not in issue, year sufficiently early).
Cundif et al., "Breeding Cattle for Improved Product Consistency," Roman L. Hurska US Meat Animal Research Center, Clay Center, Nebraska, pp. 1-28 (1994) (month not in issue).
CVP Withdrawl Time Charts (Circa more than one year prior to Oct. 31, 1994).
Daley, "Prediction of Beed Carcass Composition Using Preslaughter Linear Measures," Thesis, Colorado State University (1981) (month not in issue, year sufficiently early).
Daley, "Relationship of Pre-weaning Measures and Performance Traits in Beef Cattle," Dissertation, Colorado State University (1984) (month not in issue, year sufficiently early).
Doye and Northcutt, "Integrated Resource Management (IRM) Tools: Standard Performance Analysis Cow-Calf Software," Oklahoma Cooperative Extension Service, Oklahoma State University, F-22, pp. 222.1-222.4 (May 1994).
Edwards et al., "Using Ultrasound, Linear Measurements and Live Fat Thickness Estimates to Determine the Carcass Composition of Market Lambs," *J. Animal Science*, 67:3322-3330 (1989) (month not in issue, year sufficiently early).
Effertz, "Anxiously Awaiting Alliances," *Beef Today*, pp. 18-20 (Aug. 1994).

Epley et al., "Prediction of Weight and Percent Retail Cuts of Beef Using Five Carcass Measurements," *J. Animal Science*, 30:872-879 (1970) (month not in issue, year sufficiently early).
Faulkner et al., "Prediction of Fat Cover and Carcass Composition from Live and Carcass Measurements," *J. Animal Science*, 68:604-610 (1990) (month not in issue, year sufficiently early).
Fee, R., "High-Tech, High-Spec Cattle Feeding," *Successful Farming*, 22 pp., (Jan. 1994).
Feuz et al., "Analysis of the Efficiency of Four Marketing Methods for Slaughter Cattle," *Agribusiness*, vol. 9, No. 5, pp. 453-463 (1993) (month not in issue, year sufficiently early).
Fox and Black, "A System for Predicting Body Composition and Performance of Growing Cattle," *J. Animal Science*, 58:725-739 (1984) (month not in issue, year sufficiently early).
Fox and Perry, "Predicting Individual Feed Requirement, Incremental Cost of Gain, and Carcass Composition in Live Cattle Varying in Body Size," 8 pp. (Circa more than one year prior to Oct. 31, 1994).
Fox et al., "A Manual for Using the Cornell Net Carbohydrate and Protein System for Evaluating Cattle Diets," Revised on CNCPS Release 2 (Aug. 1993).
Fox et al., "A Net Carbohydrate and Protein System for Evaluating Cattle Diets: III. Cattle Requirements and Diet Adequacy," *J. Animal Science*, 70:3578-3596 (1992) (month not in issue, year sufficiently early).
Fox et al., "Cornell Cattle Systems 5 Users Guide: Cattle Growth and Profit Prediction Model For All Classes of Growing Cattle," (Circa more than one year prior to Oct. 31, 1994).
Gibb, "Relationships Among Feeder Cattle Characteristics and Subsequent Production Traits," Thesis, Colorado State University (1985) (month not in issue, year sufficiently early).
Gill and Lusby, "Limit Feeding Light-Weight Cattle Height Nutrient Density Diets: Programming Feeding for Calves (PROGFED2)," *Oklahoma Cooperative Extension Service Current Report*, Oklahoma State University, CR-3025, pp. 3025.1-3025.8 (Jul. 1992).
Gill et al., "Spreadsheet Programs for Calculation of Complete Diets for Beef Cattle, Checking for Nutrient Balance and Estimating Gain," *Oklahoma Cooperative Extension Service Current Report*, Oklahoma State University, CR-3027, pp. 3027.1-3027.8 (Apr. 1994).
Grafel, "Electronic tracking expands role," *Drovers Journal*, p. 12 (Circa more than one year prior to Oct. 31, 1994) (Circa more than one year prior to Oct. 31, 1994).
Greathead et al., "The relationship between ultrasonic point readings in live cattle and carcass fat cover," *J. Agric. Sci.*, pp. 651-657 (1984) (month not is issue, year sufficiently early).
Gross, C., "Computer Judgments in the Feedlot," *Calf News*, pp. 6, 28, 29, (Aug. 1984).
Hakason, W., "The Future is Now in the Health Care Industry," *Automatic I.D. News*, p. 49, (May 1987).
Hankins and Berk, "Relationships Among Production and Grade Factors of Beef," [Technical Bulletic No. 665] US Department of Agriculture (Nov. 1938).
Harrison, "Optimizing Marketing Dates for Steers by Accounting for Individual Differences," *Agriculture Economic Report*, No. 372, U.S. Department of Agriculture (Jun. 1977).

Herring et al., "Evaluation of Machine, Technician, and Interpreter Effects on Ultrasonic Measures of Backfat and Longissimus Muscle Area in Beef Cattle," *J. Animal Science*, 72:2216-2226 (1994) (month not in issue).

Hicks et al., "Daily Dry Matter Intake by Feedlot Cattle: Influence of Breed and Gender," *J. Animal Science*, 68:245-253 (1990) (month not in issue, year sufficiently early).

Hicks et al., "Dry Matter Intake by Feedlot Beef Steers: Influence of Initial Weight, Time on Feed and Season of Year Received in Yard," *J. Animal Science*, 68:254-265 (1990) (month not in issue, year sufficiently early).

Houghton et al., "Application of Ultrasound for Feeding and Finishing Animals: A Review," *J. Animal Science*, 70:930-941 (1992) (month not in issue, year sufficiently early).

Hyer et al., "The Relationship of Body Composition and Feed Intake of Beef Steers," *Animal Science Research Report*, Agriculture Experiment Station, Division of Agriculture, Oklahoma State University (May 1986).

Jeffrey et al., "Weight-based Adjustment for Ultrasonically Derived Carcass Traits Among Performance Tested Angus Bulls," *Animal Science Research Report*, pp. 49-54, (1993) (month not in issue, year sufficiently early).

Kent et al., "Estimates of Beef Carcass Intermuscular Fat," *J. Animal Science*, 69:4836-4844 (1991) (month not in issue, year sufficiently early).

Koch et al., "Characterization of Biological Types of Cattle III. Carcass Composition, Quality and Palatability," *J. Animal Science*, 43:48-62 (1976) (month not in issue, year sufficiently early).

Koch et al., "Characterization of Biological Types of Cattle-Cycle II: III. Carcass Composition, Quality and Palability," *J. Animal Science*, 49:448-460 (1979) (month not in issue, year sufficiently early).

Koch, "Selection in Beef Cattle III. Correlated Response of Carcass Traits to Selection for Weaning Weight, Yearling Weight and Muscling Score in Cattle," *J. Animal Science*, 47:142-150 (1978) (month not in issue, year sufficiently early).

Lee et al., "Effect of Cattle Type and Energy Intake on Carcass Traits and Adipose Tissue Cellularity," *J. Animal Science*, 57:621-627 (1983) (month not in issue, year sufficiently early).

Lusby and Gill, "Basic Considerations for Rations and Supplements," *OSU Extension Facts*, Oklahoma Extension Service, Oklahoma State University, No. 3012, pp. 3012.1-3012.2 (Mar. 1982).

Lusby and Gill, "Formulating Complete Rations," *OSU Extension Facts*, Oklahoma Extension Service, Oklahoma State University, No. 3013, pp. 3013.1-3013.4 (Mar. 1982).

Lusby and Gill, "Spreadsheet for Calculating Livestock Rations," *OSU Extension Facts*, Oklahoma State University, No. 3024, pp. 3024-1-3024.4 (Jul. 1991).

Lusby and Gill, "Stocker Cattle Nutrition III: Formulating Supplements," *OSU Extension Facts*, Oklahoma Extension Service, Oklahoma State University, No. 3014, pp. 3014.1-3014.4 (Jul. 1982).

Maday, "Cattle Sorting Enters a New Age," *DJ Feeder Management*, pp. 1-5 & 8 (Sep. 1994).

Maday, J., "Cattle Sorting Enters a New Age," *DJ Feeder Management*, pp. 1-5 & 8, (1994).

McPeake, "Hip Height and Frame Score Determination," *OSU Extension Facts*, Oklahoma Extension Service, Oklahoma State University, F 3271, pp. 3271-1-3271.2 (Circa more than one year prior to Oct. 31, 1994) (Circa more than one year prior to Oct. 31, 1994).

Miller et al., "Evaluation of Live and Carcass Techniques for the Predicting Beef Carcass Composition," *Meat Science*, pp. 111-129 (1988) (month not in issue, year sufficiently early).

Murray et al., "Effects of three different growth rates on empty body weight, carcass weight and dissected carcass composition of cattle," *J. Agric. Sci.*, vol. 82, pp. 535-547 (1974) (month not in issue, year sufficiently early).

Nour and Thonney, "Technical Note: Chemical Composition of Angus and Holstein Carcasses Predicted from Rib Section Composition," *J. Animal Science*, 72:1239-1241 (1994) (month not in issue).

Old and Garrett, "Effect of Energy Intake on Energetic Efficiency and Body Composition of Beef Steers Differing in Size at Maturity," *J. Animal Science*, 65:1371-1380 (1987) (month not in issue, year sufficiently early).

Olson, "Effect of Winter Environment (Range vs Drylot) on Replacement Heifer Development and Behavior," *KAES Report of Progress No. 597*, Fort Hays Branch Experiment Station, Kansas State University, pp. 1-33 (Apr. 1990).

Oltjen and Garrett, "Effects of Body Weight, Frame Size and Rate of Gain on the Composition of Gain of Beef Steers," *J. Animal Science*, 66:1732-1738 (1988) (month not in issue, year sufficiently early).

Oringderff, "A Little Black Box," pp. 39-44 (Circa more than one year prior to Oct. 31, 1994).

Owens et al., "Factors that Alter the Growth and Development of Ruminants," *J. Animal Science*, 71:3138-3150 (1993) (month not in issue, year sufficiently early).

Park et al., "Divergent Selection for Postweaning Feed Conversion in Angus Beef Cattle: III. Linear Body Meansurements of Progeny," *J. Animal Science*, 71:334-340 (1993) (month not in issue, year sufficiently early).

Perkins et al., "Evaluation of Ultrasound Estimates of Carcass Fat Thickness and Longissimus Muscle Area in Beef Cattle," *J. Animal Science*, 70:1002-1010 (1992) (month not in issue, year sufficiently early).

Phillips et al., "Effect of Pre- and Postweaning Management System on the Performance on Brahman Crossbred Feeder Calves," *J. Animal Science*, 69:3102-3111 (1991) (month not in issue, year sufficiently early).

Pratt, U.S. Appl. No. 09/227,171, Cattle Management Method and System, filed Jan. 1999.

Pratt, U.S. Appl. No. 09/426,412, Cattle Management Method and System, filed Oct. 1999.

Prior et al., "Influence of Dietary Energy and Protein on Growth and Carcass Composition in Different Biological Types of Cattle," *J. Animal Science*, 45:132-146 (1977) (month not in issue, year sufficiently early).

Sainz and Oltjen, "Improving Uniformity of Feeder Steers Using Ultrasound and Computer Modeling," *Proceedings, Western Section, American Society of Animal Science*, vol. 45, pp. 179-181 (1994) (month not in issue).

Scofield, W. & B. Boyd, "MSI Messenger," *Cattle Scanning Systems Newsletter*, vol. 1, No. 1, 2 pp., (Apr. 1994).

Swatland et al., "A Review of Probes and Robots: Implementing New Technologies in Meat Evaluation," *J. Animal Science*, 72:1475-1486 (1994) (month not in issue).

Tatum et al., "Carcass Characteristics, Time on Feed and Cooked Beef Palatability Attributes," *J. Animal Science*, 50:833-840 (1980) (month not in issue, year sufficiently early).

Tatum et al., "Infulence of Diet on Growth Rate and Carcass Composition of Steers Differing in Frame Size and Muscle Thickness," *J. Animal Science*, 66:1942-1954 (1988) (month not in issue, year sufficiently early).

Tatum et al., "Effects of Management History, Breed-Type and Carcass Characteristics of Palatability Arributes of Beef," Dissertation, Texas A&M University (Aug. 1978).

Tatum, "Evaluation of Ultrasound and Visual Appraisal for Estimation of Fat Thickness and Ribeye Area in Live Cattle," pp. 99-103 (Circa more than one year prior to Oct. 31, 1994).

Thornton et al., "Feed Intake by Feedlot Beef Steers: Inflence of Initial Weight and Time on Feed," *Animal Science Research Report*, Agriculture Experiment Station, Division of Agriculture, Oklahoma State University, pp. 321-331 (1985) (month not in issue, year sufficiently early).

Waldner et al., "Validation of Real-Time Ultrasound Technology for Predicting Fat Thickness, Longissimus Muscle Areas, and Composition of Brangus Bulls from 4 Months to 2 Years of Age," *J. Animal Science*, 70:3044-3054 (1992) (month not in issue, year sufficiently early).

Whittaker et al., "Principles of Ultrasound and Measurement of Intramuscular Fat," *J. Animal Science*, 70:942-952 (1992) (month not in issue, year sufficiently early).

Williams et al., "Comparison of Ultrasound Measurements for Predicting Retail Product and Trimmable Fat in Beef Carcasses," Abstracts from *J. Animal Science*, vol. 66, abstract 213 (1988) (month not in issue, year sufficiently early).

Williams et al., "Simulated influence of postweaning production system of performance of different biological types of cattle. II. Carcass composition, retail product and quality," Roman L. Hruska US Meat Animal Research Center, Clay Center, Nebraska, pp. 1-28 (Circa more than one year prior to Oct. 31, 1994).

Williams et al., "The Effects of Muscle Thickness and Time on Feed on Hot Fat Trim Yields, Carcass Characteristics and Boneless Subprimal Yields," *J. Animal Science*, 67:2669-2676 (1989) (month not in issue, year sufficiently early).

Zinn et al., "Feedlot and Carcass Grade Characteristics of Steers and Heifers as Influenced By Days on Feed," *J. Animal Science*, 31:302-306 (1970) (month not in issue, year sufficiently early).

"Cattle Scanning Systems," *MSI Messenger*, vol. 1, No. 1, 2 pages, Apr. 1994.

"Introducing Sorting with the MSI Scanner," Stockmen's Livestock Exchange, Dickinson, North Dakota, Feb. 1995.

"On the Humanside" *CALF News Cattle Feeder*, 1 page, Aug. 1994.

"Scanner Cuts Feed Costs by 14%," CBW, 1 page, Aug. 1993.

"The MSI Scanner," Primeline® Livestock Marketing advertisement, 2 pages, Jan. 1994.

"The Shape of Things to Come," *Feed Lot*, 2 pages, Apr./May/Jun. 1994.

Cornett, "Sorting by Computer Eye," *Beef*, 3 pages, Apr. 1984.

Fee, "High-Tech, High-Spec Cattle Feeding," *Successful Farming*, 2 pages, Jan. 1994.

Kay "New Scanner May Change Industry," *Cattle Buyer's Weekly*, 1 page, circa Sep. 1993.

* cited by examiner

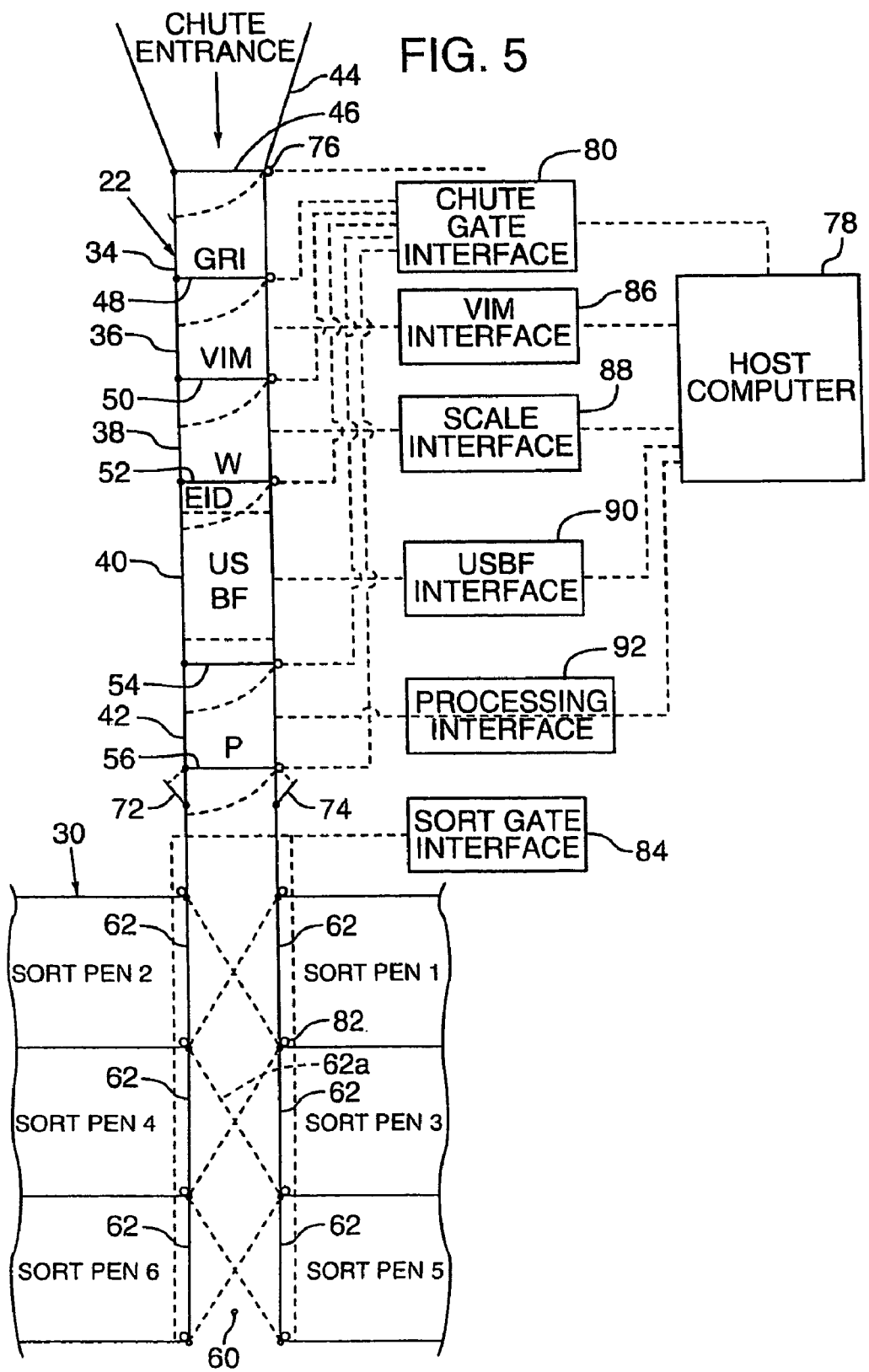

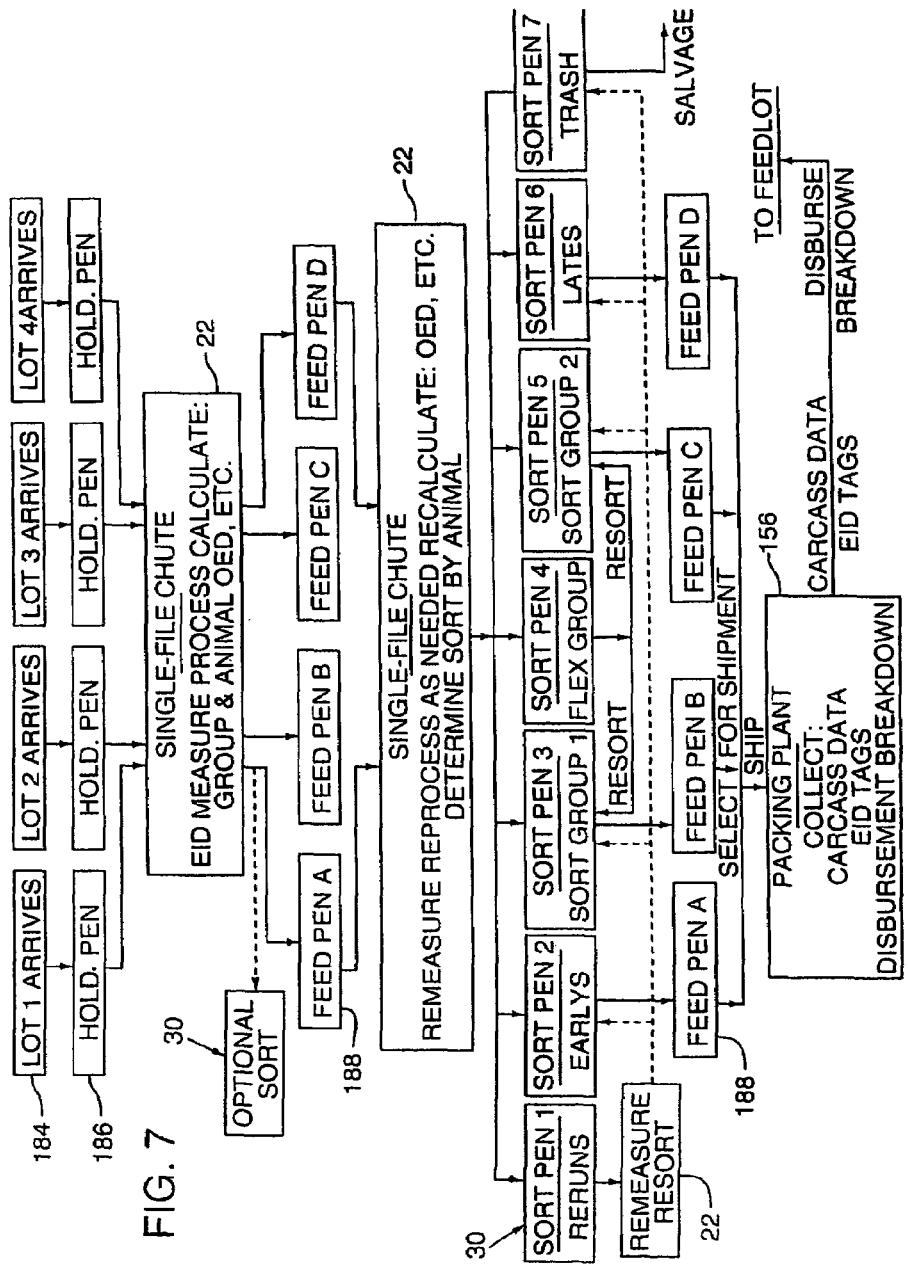

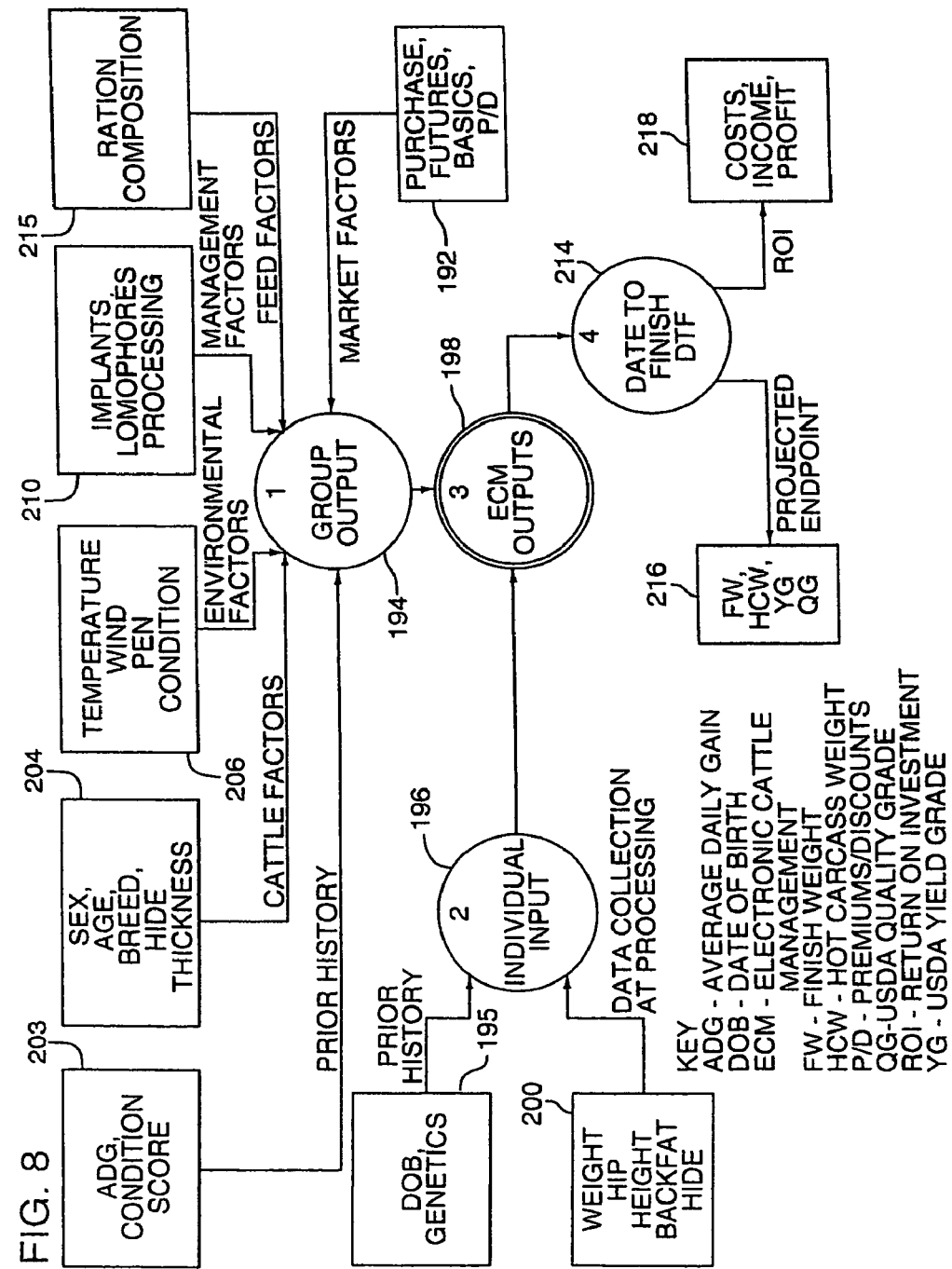

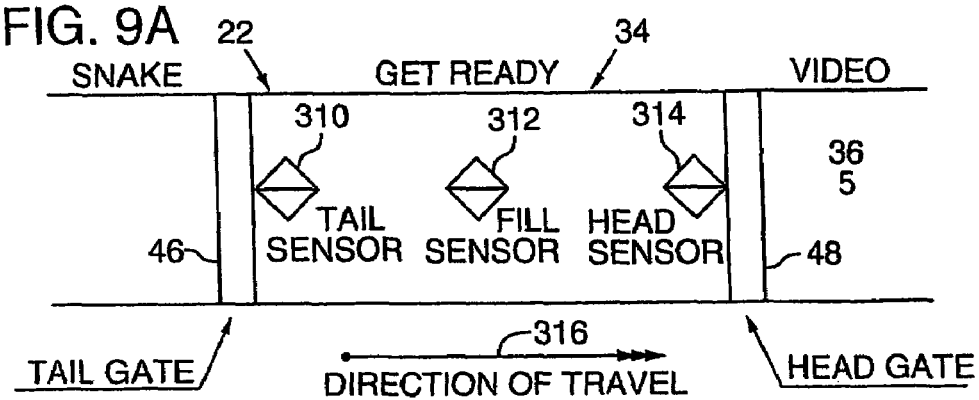
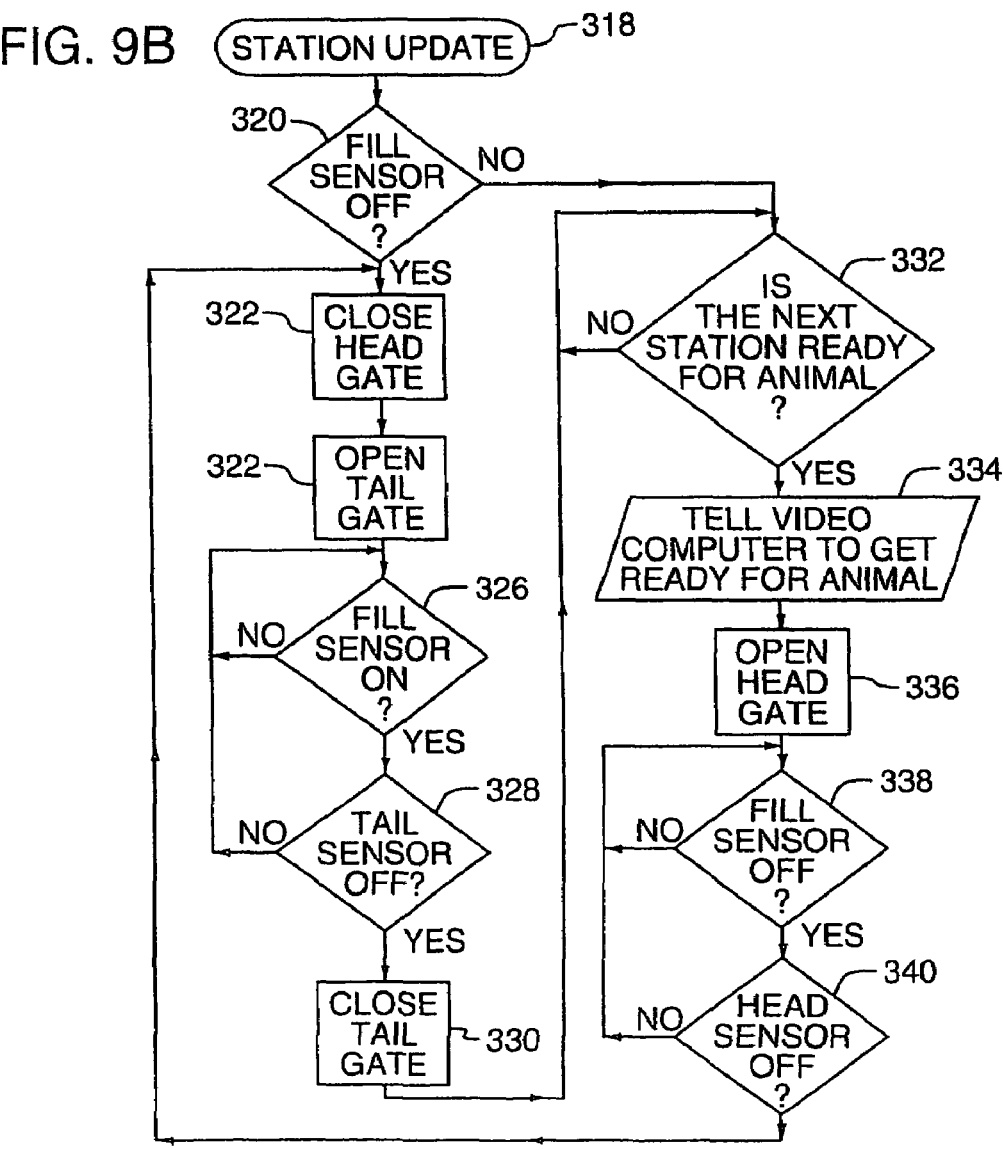

FIG. 14B
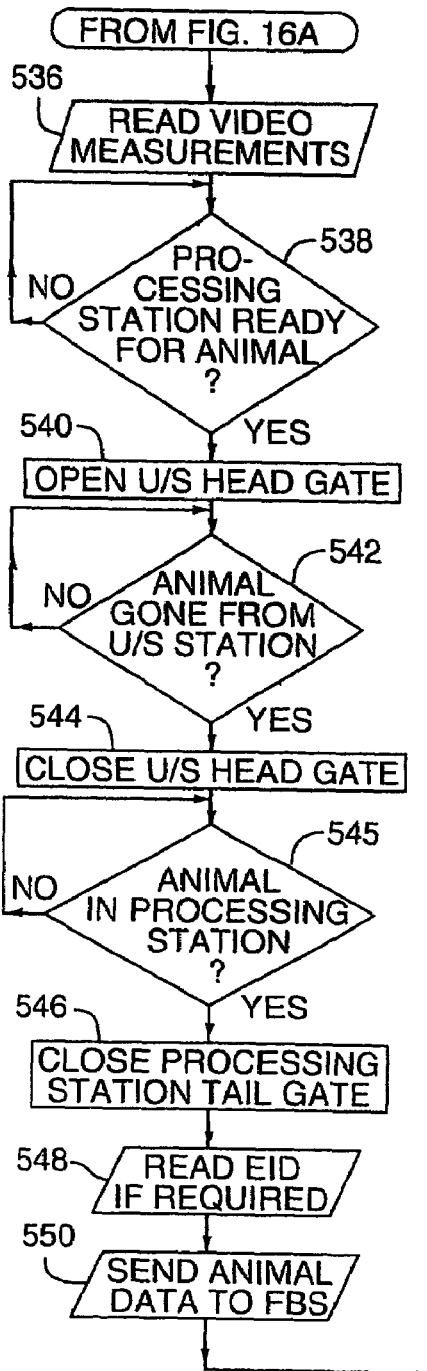
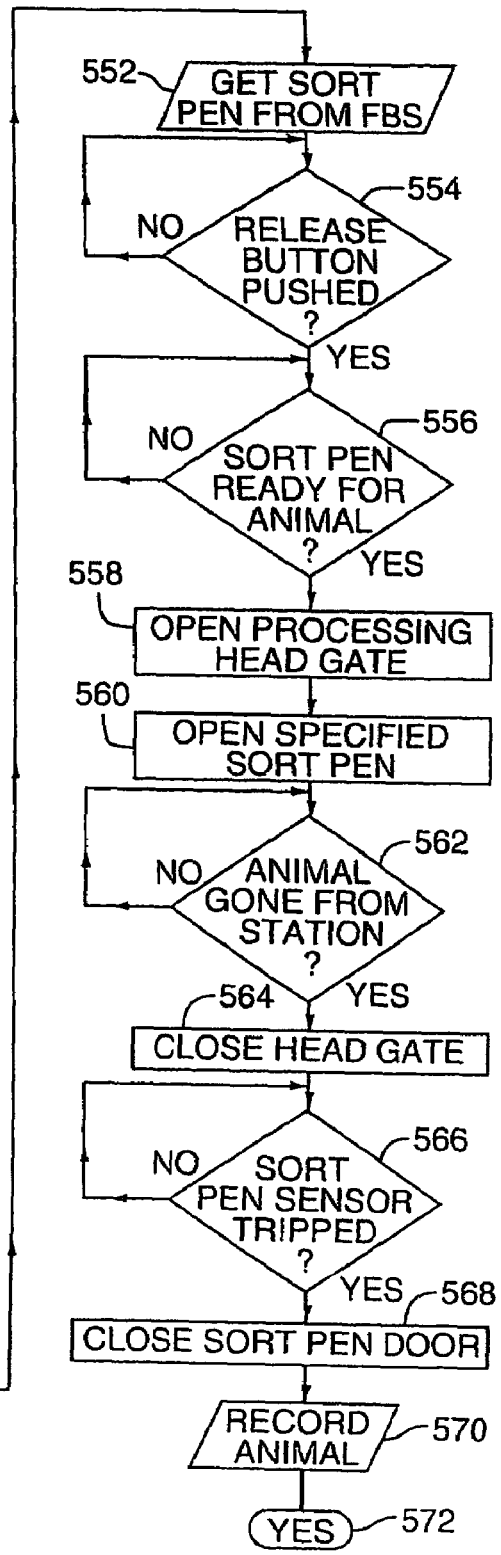

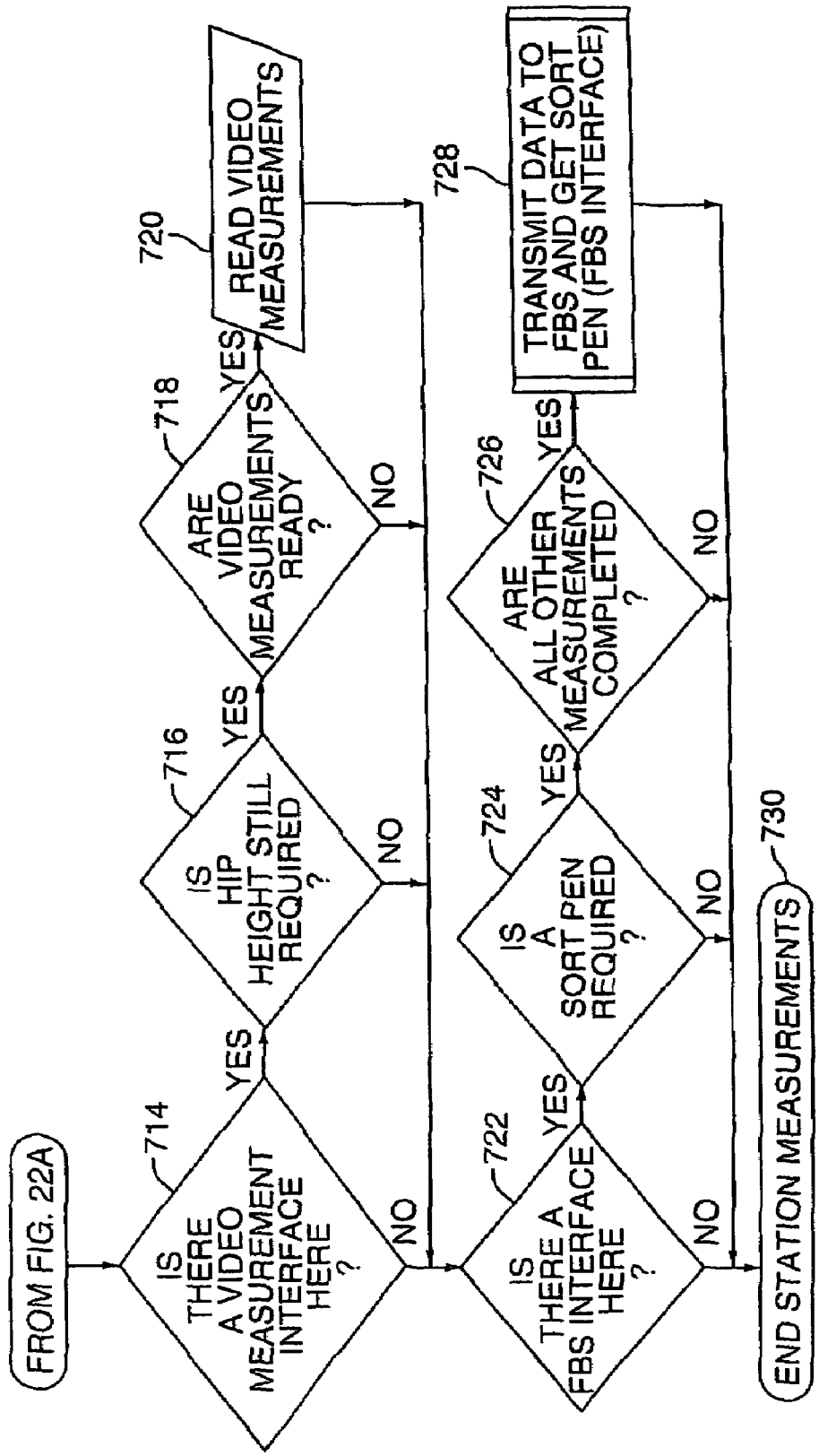

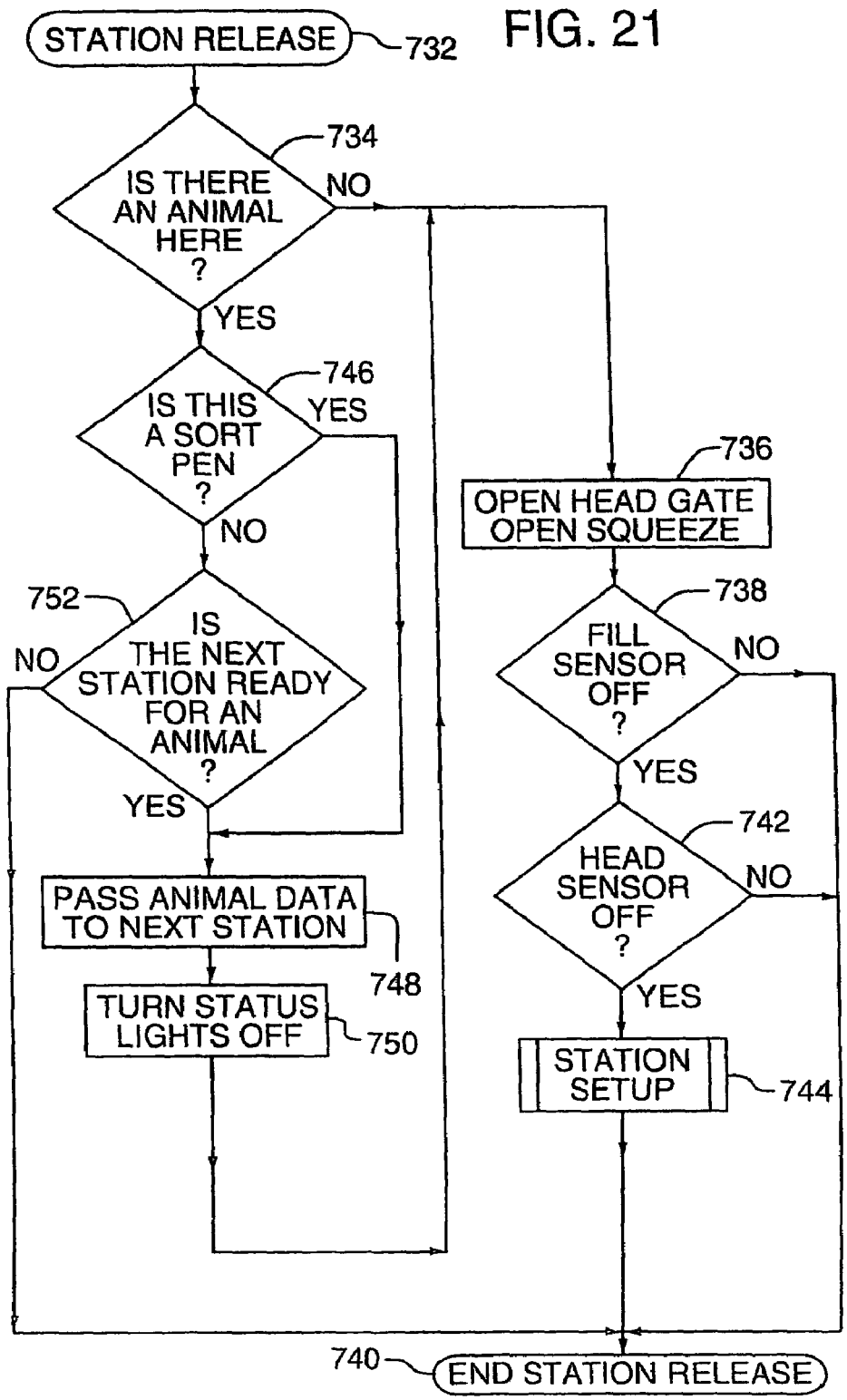

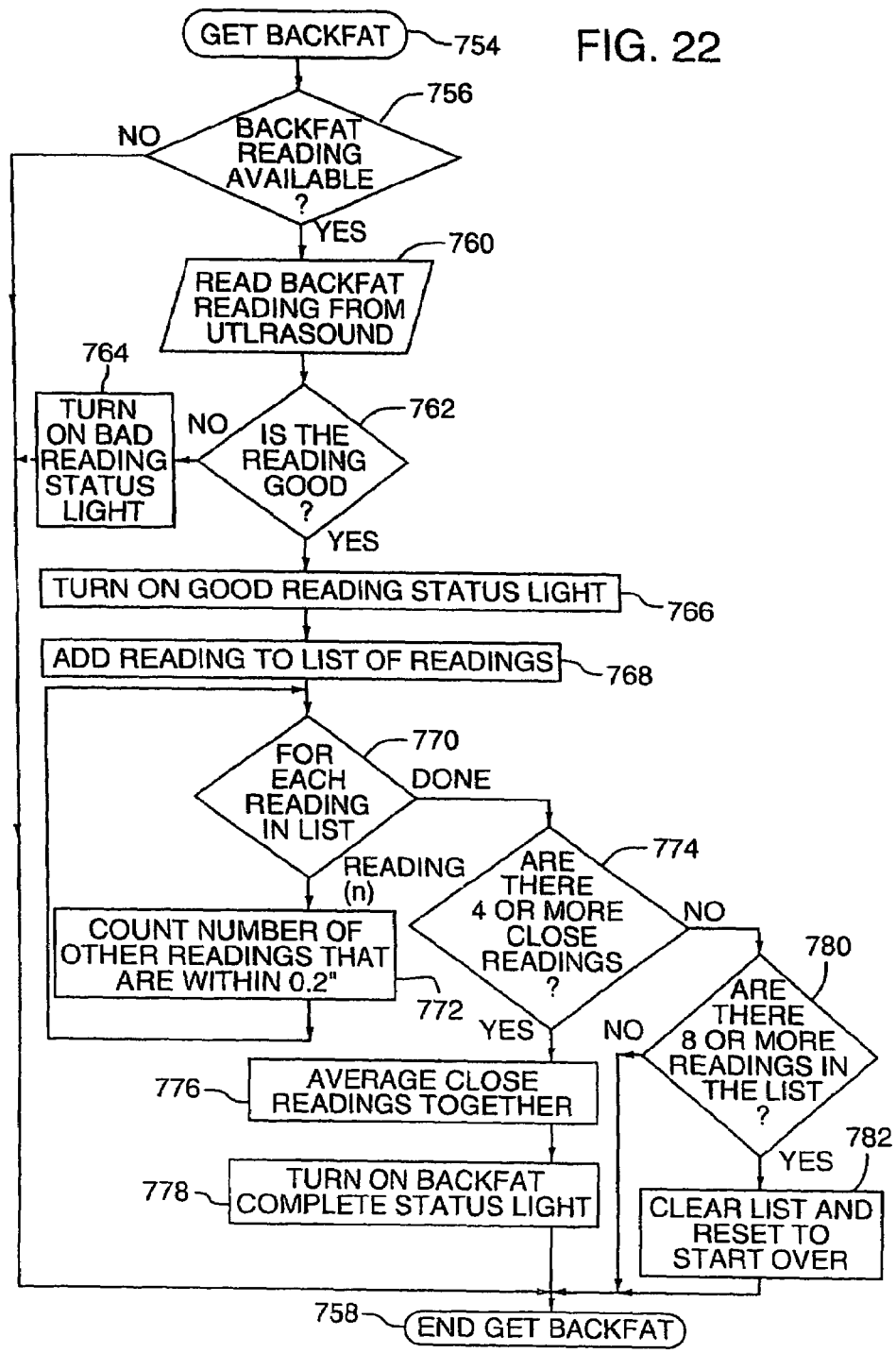

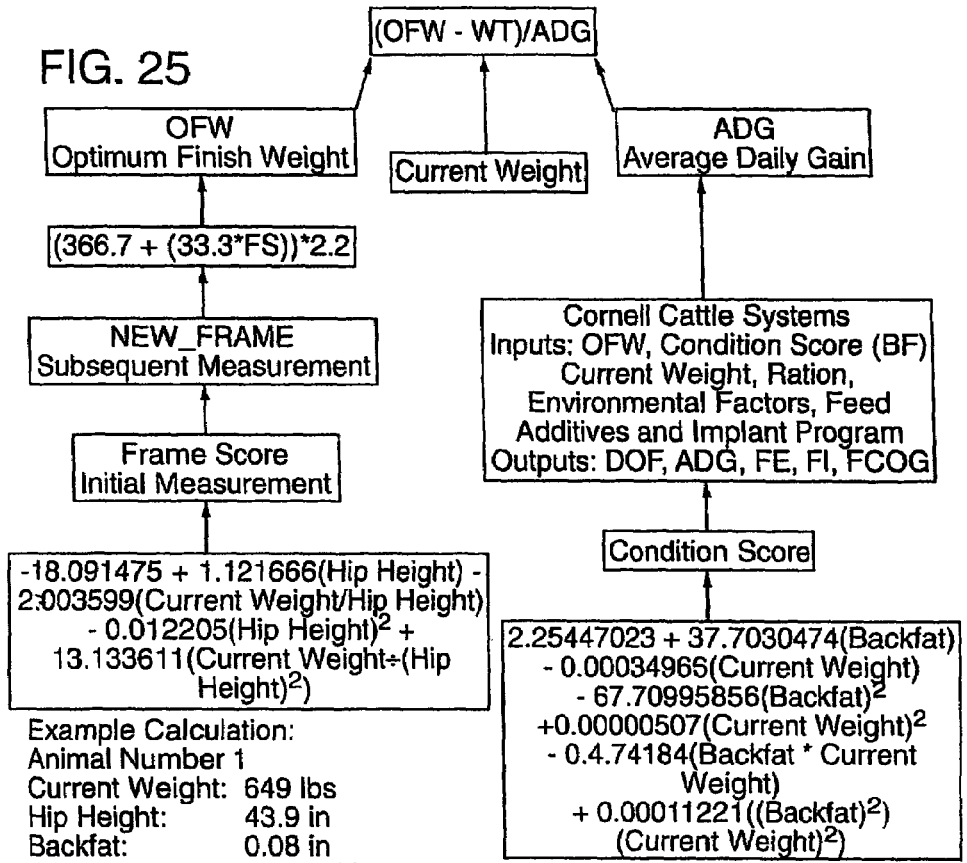

FIG. 25

Example Calculation:
Animal Number 1
Current Weight: 649 lbs
Hip Height: 43.9 in
Backfat: 0.08 in
Optimum Finish Weight (OFW)
Initial Measurement:
Frame Score = -18.091475+0.03365(649)+1.121666(43.9)-2.003599
  (649/43.9) -0.012205(43.9)$^2$+13.133611(649(43.9)$^2$)
=4.27 (rounded to 2 decimal places)
Subsequent Measurement;
NEW_FRAME = ((BFDR - 0.01253)÷(-0.00065) (From DTF Method One)
=(0.0097689 - 0.01253)÷(-0.00065)=4.25
OFW=(366.7 + (33.3*4.25))*2.2=1118 lbs
Condition Score:
=2.25447023+37.703047(0.08)-0.00034966(649)-67.70995853(0.08)$^2$
  +0.00000507(649)$^2$-0.04374184(649*0.08)+0.00011221((0.08)$^2$*(649)$^2$)
-5 (rounded to nearest whole number)
Input into Cornell Model: Current Weight, OFW, Condition Score
Output from Cornell Model: ADG = 3.34
DTF=(1118-649)÷3.24=145 Days (rounded to nearest whole number)

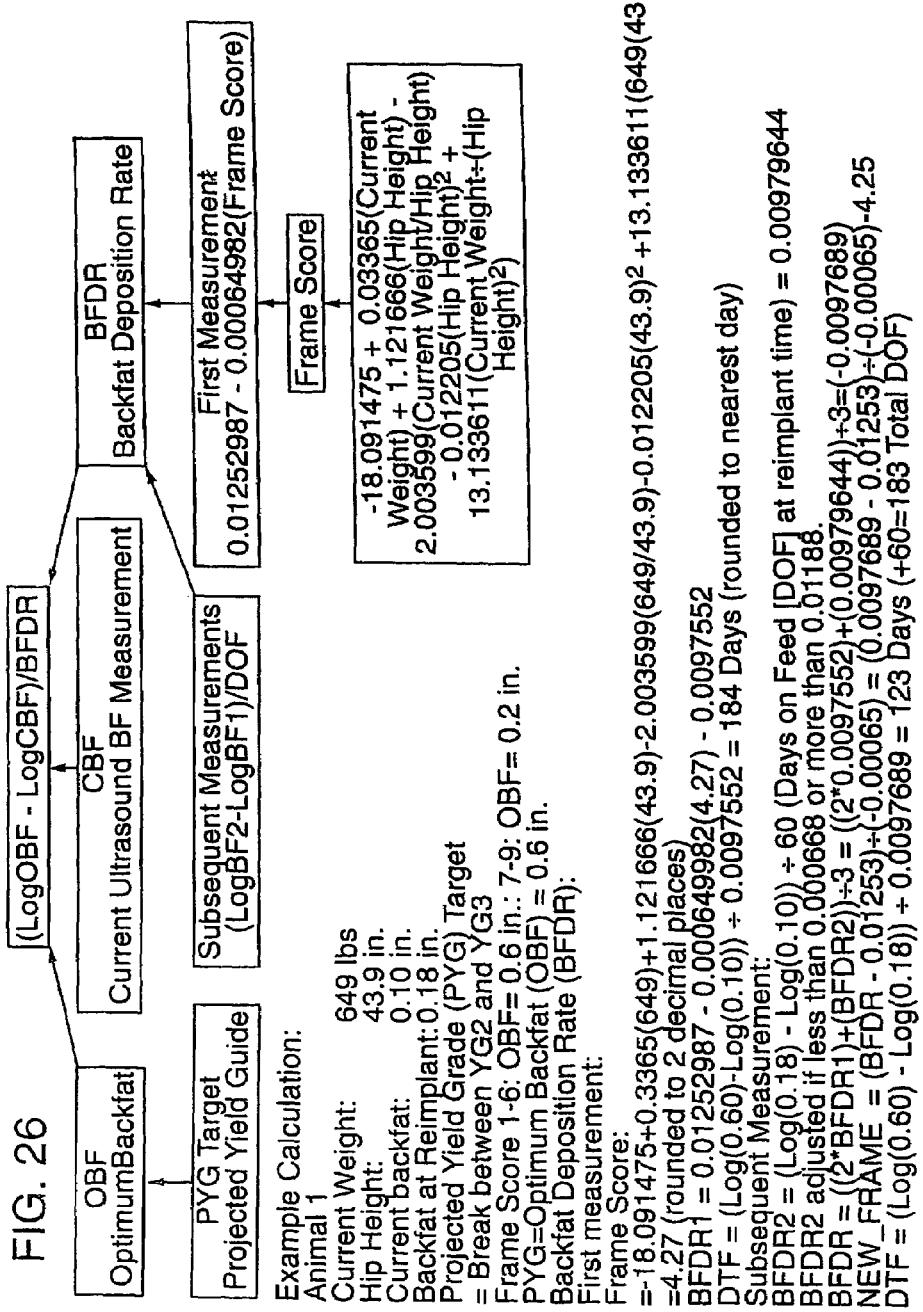

FIG. 28b

2) Calculate DMI ratios to be used from the remeasurement date to the next measurement to prorate feed to each lot/pen., by inputting Hip Height, Backfat, Current Weight and OFW. When a final weight is calculated for each animal (after slaughter), the Cornell Cattle Systems model will be used to determine DMI ratios for each animal to reapportion total feed fed per pen to calculate individual animal consumption in each lot/pen. Inputs are Initial Weight, Final Weight and Condition Score (based on actual Backfat)

Example Calculation:

| Animal # | Weight | Current Wt | Hip Height | Backfat | FS | CS | | OFW |
|---|---|---|---|---|---|---|---|---|
| 85 | 829 | 1028 | 45.8 | 0.14 | 4.50 | 6 | | 1136 |
| 10 | 867 | 1066 | 47.2 | 0.18 | 5.14 | 6 | | 1183 |
| 68 | 738 | 937 | 43.3 | 0.2 | 3.45 | 6 | | 1059 |
| 36 | 777 | 976 | 45.2 | 0.12 | 4.37 | 5 | | 1127 |

| Animal # | CP¹DMI | Ratio | | CP | | NP2 DMI | Ratio | NP Feed Fed | NP Prorated Feed |
|---|---|---|---|---|---|---|---|---|---|
| | | | | Feed Fed | Prorated Feed | | | | |
| 85 | 19.47 | 0.255646 | | | 767 | 21.13 | 0.253206 | | 1519 |
| 10 | 20.13 | 0.264312 | | | 793 | 21.81 | 0.261354 | | 1568 |
| 68 | 17.92 | 0.235294 | | | 706 | 19.81 | 0.237388 | | 1424 |
| 36 | 18.64 | 0.244748 | | | 734 | 20.7 | 0.248053 | | 1488 |
| Total | 76.16 | 1 | | | 3000 | 83.45 | 1 | | 6000 |

| Animal # | HCW | Actual BF | Final Wt. | DMI Overall | Ratio | Feed Fed | Prorated Feed | Feed/Gain |
|---|---|---|---|---|---|---|---|---|
| 85 | 716 | 0.25 | 1128 | 20.50 | 0.25262 | | 2440 | 8.17 |
| 10 | 745 | 0.3 | 1163 | 21.26 | 0.26203 | | 2531 | 8.54 |
| 68 | 667 | 0.35 | 1034 | 19.22 | 0.23686 | | 2288 | 7.72 |
| 36 | 710 | 0.25 | 1118 | 20.16 | 0.24849 | | 2400 | 7.03 |
| | | | | 81.14 | 1 | 9660 | 9660 | |

¹CP - Current Period (initial measurement to remeasurement)
²NP - Next Period - DMI ratios to be used for period from remeasurement to next measurement.

CATTLE MANAGEMENT METHOD AND SYSTEM

CROSS REFERENCE TO RELATED APPLICATION

This application is a continuation of prior U.S. application Ser. No. 10/323,115, filed Dec. 18, 2002 now U.S. Pat. No. 6,805,075, which is a continuation of U.S. application Ser. No. 09/967,151, filed Sep. 27, 2001, now issued as U.S. Pat. No. 6,516,746, which is a continuation of U.S. application Ser. No. 09/426,412, filed Oct. 25, 1999, now issued as U.S. Pat. No. 6,318,289, which is a continuation of U.S. application Ser. No. 09/227,171, filed Jan. 7, 1999, now issued as U.S. Pat. No. 6,135,055, which is a continuation of U.S. application Ser. No. 08/83 8,768, filed Apr. 10, 1997, now issued as U.S. Pat. No. 6,000,361, which is a continuation of U.S. application Ser. No. 08/332,563, filed on Oct. 31, 1994, now issued as U.S. Pat. No. 5,673,647.

FIELD OF THE INVENTION

The present invention relates generally to the management of cattle in a feedlot for optimum beef quality and optimum return on investment to the producer and feedlot.

This invention relates more particularly to processes and systems for individual animal value-based management of cattle for the production of beef for human consumption by measuring, sorting and tracking animals individually and in groups to manage the diversity in individual animals for optimum efficiency and value.

BACKGROUND OF THE INVENTION

A feedlot is a place where cattle producers, such as ranchers, send their cattle to promote their growth and improve their condition and characteristics before shipment to a meat packer for slaughter.

Feedlots generally care for thousands of head of cattle or other animals at once in various stages of growth. These animals come from a variety of sources with widely varying previous care and feeding performance history. Cattle within a feedlot are physically contained in cattle pens, each pen typically having a feed bunk to receive feed, a water source for drinking, and manually-operated gates to enter and exit the pens. A feedlot typically includes a hospital area where individual animals that are ill or otherwise in need of treatment can be medicated or otherwise treated and returned to their pens. It also includes a receiving area where cattle are contained upon their arrival at a feedlot, a processing area where cattle, shortly after their arrival, are tagged, weighed and given health care and growth promotant products, and shipping area where cattle are prepared for shipment to a packing plant for slaughter.

Ownership of particular cattle in a feedlot is defined by a unique lot number. The number of cattle in a lot may vary, and an owner may own a portion of a lot, a portion of multiple lots, or all of one or more lots. Each lot may occupy one or multiple pens.

Proper care for animals in a large feedlot is a complex and time-consuming task because of, for example, feeding, water supply, insect control, and individual or group treatment requirements. Treatments may include group treatments where various medications are added to the feed, or individual treatments that are applied topically, orally, by injection or by implantation to selected individual or groups of animals. Regular sorting of animals also occurs.

Movement of the animals individually and in groups may occur several times during the several month period each animal is kept in the feedlot due to the above-mentioned reasons and others. This movement of animals from their home pen to other pens, from a home pen to a treatment area and later return, and from several pens into a common pen, is necessary for the proper care and maintenance of the animals.

Feedlots have various charges assessed to owners for the care and maintenance of their animals. These charges are typically assessed by lot number at periodic intervals based on feedlot care and maintenance records, not on an individual animal basis. Examples of these are feed ration charges in dollars per ton, health care and growth promotion product charges, a daily yardage fee per head, and handling charges. For optimum accuracy of these records and charges, they would be kept on an individual animal basis, but this is not possible with current feedlot management systems.

Within the feeder cattle population, there is tremendous diversity in individual animal characteristics due to both genetic and environmental factors such as weight, frame size, muscling, fat content and deposition rate, breed type, rate of gain, feed efficiency, intramuscular fat (marbling), sex, age, health and drug treatments, nutrition and growth history, and other factors.

Ideally, the physical and growth characteristics of each animal should be known at every stage of its stay in the feedlot in order to determine when the animal should be slaughtered for optimum growth efficiency and value of the carcass based upon a carcass grading target and market conditions. However, this is not now possible, as a practical matter, in large feedlots, with existing feedlot management methods and systems.

This extreme diversity in the cattle population within a feedlot coupled with the need to produce a quality end product at the lowest possible cost for the maximum economic return to the feedlot and the producer, results in a need to be able to measure and track the physical and performance characteristics of each animal during its residence in the feedlot for optimum marketing date selection. This is something that heretofore has not been possible, as a practical matter.

Methods and systems used prior to this invention have been too inaccurate or have lacked the capability to identify and track characteristics of performance and charges on an individual animal basis. Additionally, they have been too labor intensive and too injurious to animals, and have required skill levels not readily available in feedlots.

The livestock industry has tried for years, with limited success, to improve the genetics of the cattle population to produce the types of animals that will yield a high percentage of lean meat and a low percentage of fat efficiently. However, until now there has been no effective way for large feedlots to measure and sort animals individually, keep accurate and complete records of live physical characteristics and charges for each animal, and to produce an economic end point determination for each animal using growth performance data. Nor has there been an effective way to match growth performance data to end product carcass data for each animal from slaughtering operations that would enable a correlation between carcass value and live animal performance and measured characteristics so as to help identify superior genetic types for future breeding and management purposes, and to identify management practices that will maximize the value of the arrival in the market.

The cattle growth and production industry comprises two major components, producers and feedlots with many grower-type operations in between. The cattle producers maintain cow herds. The herds produce calves that are raised and grown on pasture grazing land, much of which is unsuitable for cultivation. The calves are grown to a certain size, after which they are moved to a confined feedlot where they are fed grain and other products grown on tillable farmland, in a nutritionally balanced ration. Although feedlot sizes range from a one-time capacity of a few head to a capacity of over one hundred thousand head, the trend in North America is towards large feedlots in the ten thousand to one hundred thousand head capacity.

These larger feedlots feed the majority of feedlot-fed cattle in North America intended for beef consumption.

The extremely diverse beef cattle population results in an extremely variable beef product for the consumer in terms of eating quality, fatness, tenderness, size of cuts and other factors. It has been a primary goal of the beef industry associations to improve the quality and uniformity of beef for the American consumer for many years. The 1991 Beef Quality Audit identified approximately $280 per head being wasted, of which more than $150.00 was excess fat. In order to improve the current beef product, it is first necessary that the current diverse cattle population be managed for optimum efficiency and desired carcass cut out quality and value for the consumer. Second, ultimately the genetic make up of the producer cow herd must be changed based on feed-back of data concerning the quality and quantity of lean meat yield from carcasses, live performance and the live physical data from individual animals. Such data can then be traced to the sire and dam of each animal in order to make breeding decisions about the types of animals to produce in the future.

While many methods of measurement and selection of cattle in feedlots have been tried, both visual and automated, none have been successful in accomplishing the desired end result. That end result is the ability to select a given animal for shipment at the optimum time, considering the animal's condition, performance and market factors, the ability to grow the animal to its optimum individual potential of physical and economic performance, and the ability to record and preserve each animal's performance history in the feedlot and carcass data from the packing plant for use in cultivating and managing current and future animals for meat production. The beef industry is extremely concerned with its decreasing market share relative to pork and poultry. Yet to date, it has been unable to devise a system or method to accomplish on a large scale what is needed to manage the current diversity of cattle to improve the beef product quality and uniformity fast enough to remain competitive in the race for the consumer dollar spent on meat.

In order for this problem to be solved, some method and system is needed for managing cattle in large feedlots which has the ability to identify and monitor key characteristics of individual animals and manage those individual animals to maximize their individual potential performance and edible meat value. Such system must further be able to collect, record and store such data by individual animal identification so that it is usable to improve future animals bred by the producer and managed by the feedlot.

KNOWN METHODS AND SYSTEMS RELATING TO FEEDLOT OPERATIONS

While others have conceived or used apparatuses or methods intended to simplify or otherwise improve certain specified aspects of a feedlot operation, none have been known to address the broader need for a system and method for managing all aspects of the care, feeding, and marketing of cattle in a feedlot, on an individual animal basis if desired, from the time of their arrival to the time of their shipment for slaughter, for optimum feed and drug efficiency, animal health, animal performance, and profit to the feedlot producer.

For example Pratt U.S. Pat. No. 4,733,971, issued Mar. 29, 1988, U.S. Pat. No. 4,889,433, issued Dec. 26, 1989, U.S. Pat. No. 4,815,042, issued Mar. 21, 1989, U.S. Pat. No. 5,219,224, issued Jun. 15, 1993, and U.S. Pat. No. 5,340, 211, issued Aug. 23, 1994, address the problem of delivering feed additives into animal feed rations in a feedlot accurately and on a customized basis at the time of feeding. Pratt U.S. Pat. No. 5,008,821, issued Apr. 16, 1991, addresses the problem of determining accurately the amount of feed ration to deliver to a particular pen of animals at each feeding. Pratt U.S. Pat. No. 5,315,505, issued May 24, 1994, addresses the problem of keeping track of drug inventories, drugs administered to particular animals, and animal health histories in a cattle feedlot, and determining what drugs or combinations thereof should be administered, and in what dosages, to a particular animal diagnosed with a specific illness.

While the foregoing patents address important aspects of cattle management in a feedlot, they do not address the broader aspect of how, when and how often to measure, sort, feed and treat animals in a feedlot, how long to feed them, and how and when to select them for shipment from the feedlot.

Hayes U.S. Pat. No. 4,745,472, issued May 17, 1988, and others, have proposed ways to accurately measure an animal's external dimensions by scanning using video imaging techniques. Similarly, ultrasound backfat measurement of cattle is known, at least on an experimental basis, from the work of Professor John Brethour of Kansas State University's Fort Hayes Experimental Station, as explained in an article entitled "Cattle Sorting Enters a New Age" appearing at pages 1-5 and 8 of the September, 1994 issue of *D.J. FEEDER MANAGEMENT*. Professor Brethour has, on an experimental basis, used the data from such measurements to project an estimated optimum shipping or end date (OED) for the measured animals.

Also, various methods of sorting and weighing cattle have been known or proposed, as disclosed, for example, in Linseth U.S. Pat. No. 4,288,856, Hayes U.S. Pat. No. 4,617,876, and Ostermann U.S. Pat. No. 4,280,448.

Cattle Scanning Systems of Rapid City, S. Dak., markets a computerized video imaging and sorting system that includes weighing and scanning external dimensions of each animal, assigning a frame score and muscle score to the animal based on such dimensions, calculating a predicted optimal end weight and marketing date from the composite score and current weight data, and then sorting the animals for feeding according to their optimal marketing dates.

Recently, within the last year, the aforementioned Brethour has suggested using data from ultrasound backfat measurement of individual animals, 60-80 days into a feeding period, and a computer modeling program, to physically sort cattle into groups according to projected marketing dates as they are measured, apparently based on the ultrasound-generated data alone.

The aforementioned Hayes U.S. Pat. No. 4,617,876 discloses a computerized system for controlling, by weight, the movement and location of individual animals within one or multiple pens in a feedlot using a system of animal watering and weighing stalls and electronic ear tags to identify each animal. The weight of an animal as measured within the stall determines where the animal is routed within sections of a pen or among multiple pens. Although the Hayes '876 patent suggests generally that criteria other than weight may be used to control the operation of a stall exit gate and other gates to route an animal to a desired location, it does not suggest how such other criteria could be efficiently obtained, or that such criteria can be used to determine an animal's economic and physical performance and value, or to improve future feedlot management practices or future breeding and selection practices. Nor does it suggest that combinations of two or more criteria may be used to route an animal or determine its location within multiple pens or other areas.

The aforementioned Linseth patent discloses a computerized method of sorting animals in a feedlot according to weight gain. Each incoming animal is identified and weighed in a walk-through scale, and its identification and weight are recorded. At a later date each animal is reweighed in the walk-through scale and its weight gain is determined. From this determination, the animals are sorted into pens according to weight gain, and underperforming animals are culled from the group.

None of the foregoing methods or systems use more than two criteria for selecting, sorting or predicting an optimal marketing date. Also, none teaches or suggests a way in which such prior methods or systems might be integrated into a total system of cattle management for maximum economic return to the feedlot and the producer, and for optimum use of the accumulated data for each animal to determine production costs of each animal and to improve the genetics of future breeding stocks.

There is a need for such a total management system, and this need is addressed by the present invention.

OBJECTIVES AND SUMMARY OF THE INVENTION

Therefore, a primary objective of the present invention is to provide a system and method of cattle management in a feedlot that will produce the optimum economic return to the feedlot and producer for each animal in the feedlot.

Other objectives are to provide a method and system as aforesaid that:

(1) enables the accurate determination, tracking and projection of animal performance, feed consumption, health history, costs of feed, drugs, and handling, physical characteristics, optimal marketing date, carcass data and profit, on an individual animal basis;

(2) enables efficient and accurate measurement, movement, selection, sorting, and remeasurement and resorting if desired, of animals into groups for feeding, processing or marketing, based on individual animal factors other than ownership, type, date of arrival, or the like, for optimum feeding, treatment, handling and marketing efficiency;

(3) enables the accurate and efficient grouping of animals, and, if desired, regrouping of animals, in a feedlot according to similar projected shipping dates, similar physical characteristics, similar feed ration requirements, or any other desired factors or combinations thereof, without regard to ownership, arrival date, lot number, or the like; and (4) enables the accurate and efficient accumulation, recording and correlation of historical data, feedlot performance data, and carcass data for each animal, and the transmission of such data (a) to the producer for use in the genetic selection and breeding of future animals for beef production, and (b) to the feedlot for improving the accuracy of performance, feed and marketing projections for future animals of similar characteristics in the feedlot;

(5) enables the accurate and efficient measurement, selection and tracking of individual animals and their respective physical, performance and carcass characteristics, and the correlation of those characteristics for improved slaughter date and production cost projections, for improved efficiency and value, and for use of such data to more accurately and efficiently breed, select and manage future animals;

(6) enables tracking each animal or group of animals from one location to another in a feedlot, even when mixed with other animals or groups, so that an accurate calculation and allocation of production costs by individual animal can be determined;

(7) enables the user quickly to review from a remote location an up-to-date cattle inventory by individual or group by location including health and performance status of individual animals after those animals have been sorted, remixed and retained and fed in a group, along with projected slaughter dates, production costs and animal growth status so that the user may use such data to make a decision on the proper date to ship a particular animal for slaughter;

(8) provides a high speed, gentle, multiple measurement, selection and sorting system for sorting of animals with diverse characteristics into uniform marketing groups based upon optimum slaughter date, or groups based upon uniform physical characteristics, or both, regardless of ownership, original lot number or other commonly used criteria for pen allocation; and (9) allows the user to assign treatment, sorting and movement criteria, and other instructions for cattle management, electronically by cable or RF transmission directly from a remote location to the animal location for action that avoids the need for handwritten or printed messages, delays or loss of information.

(10) enables the accurate measurement, tracking and projection of the performance of individual animals so they may be selected for marketing at a time which will maximize the optimum economic performance of each animal.

(11) enables the accurate determination of individual animal projected marketing dates utilizing projected incremental production costs of individual animals compared to projected market value of such individual animals and using that data to select individuals or groups of animals for shipment for slaughter on a date that will maximize the economic performance of the individual or group.

To achieve these objectives, a process and system for recording, measuring, sorting and tracking individual animals includes a computer system for receiving, recording, and storing data by individual animal, and for calculating performance, marketing, sorting, costs and other information from such data by individual animal. Providing such data to the computer are automatic data entry means accessible at the various animal locations. The accuracy and integrity of the data is made possible by the use of electronic or other automatic identification devices on each animal, and by computerized reading of the automatic identification device and multiple measurements without the need for an operator visually to interpret measurements and enter them into a computer keyboard, thus eliminating human error.

To retrieve information or monitor animal performance and cost/value status, operators can remotely access the information with computer terminals, with RF signals such as RF transmitters and receivers, or via cables to other parts of the system.

To achieve these objectives, the invention includes an integrated measuring, sorting, performance monitoring, cost allocation and market selection system that measures and monitors various characteristics of individual animals multiple times or in multiple ways, for example:

A) by weight multiple times;
B) by external dimensions; or
C) by internal fat or other tissue characteristics (dimensions or texture).

It has been determined that previous management methods have not obtained enough individual animal data to (a) accurately measure performance, (b) project performance and slaughter dates accurately, (c) build an accurate historical database, and (d) quickly and accurately identify a sufficient number of physical characteristics to enable accurate calculation of performance and value. Also, prior methods and systems have been unable to measure, project and keep track of animal feed consumption and production costs accurately on an individual animal basis.

In a presently preferred embodiment, each animal arriving at a feedlot is directed through a one-way, single-file chute, where it is at least weighed, identified with an electronic ear tag, and processed such as by implantation of a growth promotant. It may also be scanned by video imaging to determine its external dimensions or measured for backfat using ultrasound, or both. All measurement and processing occurs within computer-controlled gated stalls within the single-file chute. The animals are then directed to feed pens for an initial feed period. During this initial period the animals may be grouped by ownership, weight, projected marketing date, any other criteria, or even randomly.

In any case, from the initial measurement and historical data available, a projected marketing date, projected average daily gain, and feed proration is calculated for each animal.

Sixty to ninety days into the feeding period, typically at reimplantation time, if required, selected groups of the animals having, for example, similar projected marketing dates, are moved again through the single-file chute, where they are reweighed, video-scanned for external dimensions, subjected to ultrasound for backfat measurement, and reprocessed (reimplanted) if necessary. From the new data and previous data, the average actual daily gain is calculated, and feed proration and projected marketing date are recalculated.

Based on the data, the computer system also sorts each animal into one of seven groups, including "earlies", "lates", "sorting group 1", "sorting group 2", "flex groups", "reruns" and "trash". These groups are automatically directed into sorting pens, by group as they exit the single-file chute. The "trash" group consists of underperforming animals that are removed from the feeding process. The "reruns" are animals whose measurements were not recorded and are sent back through the single-file chute for remeasuring and then sorted into one of the remaining groups. The "flex" group consists of animals that are in-between the group 1 and group 2 sort standards. They are sent back through the single-file chute identification and then resorted either into group 1 or group 2 to fill out the desired number of animals in those two groups. The resulting four groups are then moved from the sorting pens to respective feed pens. There they are fed and monitored, and finally selected for shipment to the packing plant, based on their performance, projected shipping dates and market conditions. While the animals are in their feed pens, their weight may be monitored using a portable or permanent identification and weighing system within or close to the pen. Selection for shipment may be on a group or individual basis, and may be done manually (visually) or by computer.

When an animal is shipped to the packing plant, its electronic ear tag goes with it so that the animal's carcass data recorded at the packing plant can be correlated to the live animal and to its feedlot and historical data. The carcass data for each animal, including grading, cost and market value data, can then be transmitted to the feedlot, and to the producer for use by each, the producer in making breeding, selection or purchase decisions, and the feedlot in making management decisions and in allocating costs to the owner on an individual animal basis.

BRIEF DESCRIPTION OF DRAWINGS

FIG. 5 is an enlarged schematic diagram of the single-file measuring chute and adjacent sorting pens similar to those shown in FIG. 1, but on an enlarged scale and showing schematically a control means for controlling the operation thereof.

FIG. 7 is a cattle processing diagram but in considerably greater detail than those of FIGS. 4A, 4B and 4C to illustrate a method of the present invention.

FIG. 8 is a data flow block diagram illustrating the data flow in a computerized control system according to the present invention.

FIG. 9A is an enlarged schematic diagram of the get ready stall of the single-file chute shown in FIGS. 1 and 5, including the locations of sensors used in such stall.

FIG. 9B is a flow diagram of the computer program used to operate the entrance (tail) gate and exit (head) gate in conjunction with the sensors of FIG. 11A for the get ready station.

FIG. 21 is a flow diagram of a computer program used for preparing a station or a sort pen for releasing an animal from the station or sort pen to another destination.

FIG. 22 is a flow chart of a computer program used for reading the ultrasound backfat data of an animal at the ultrasound measuring station of the single-file chute shown in FIG. 5.

FIG. 25 is a flow diagram illustrating the process and formulas for calculating "Days to Finish", followed by an example calculation based on hypothetical animal measurements.

FIG. 26 is a flow diagram illustrating an alternative method to that of FIG. 25 for calculating "Days to Finish" for an individual animal, followed by an example calculation based on hypothetical measurements of the animal.

FIGS. 28a and 28b are a flow chart illustrating the process of determining feed proration to individual animals in a feedlot following a second and subsequent sets of animal measurements in the feedlot.

DETAILED DESCRIPTION OF PREFERRED EMBODIMENTS

Figure 1:
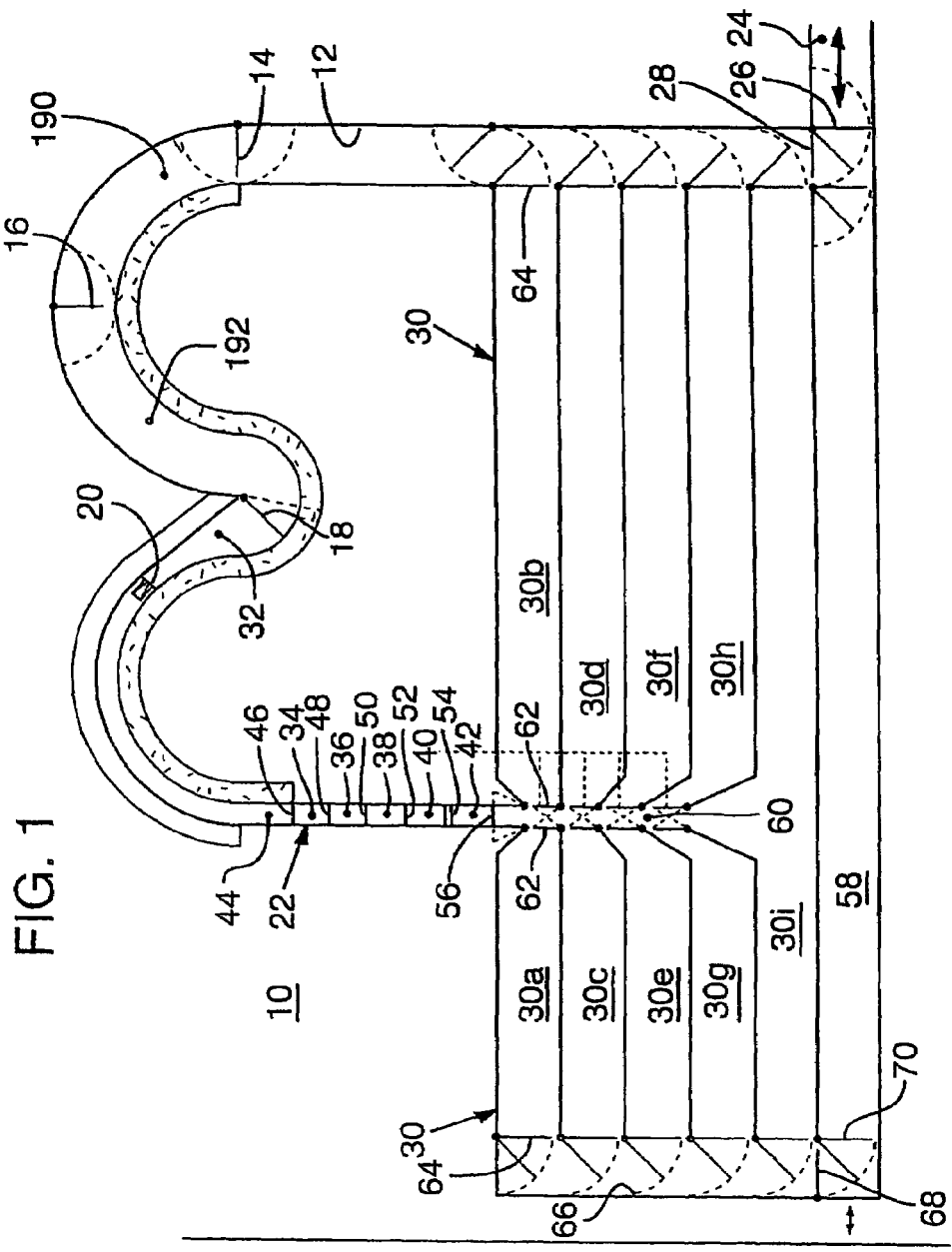
FIG. 1 is a schematic diagram of the layout of the single-file cattle processing chute and sorting pen portion of a feedlot in accordance with the invention.

A. Description of Feedlot FIG. 1 illustrates a feedlot 10 which would typically include a series of feed pens (not shown) where cattle would be fed selected feed rations and watered during their stay in the feedlot. For example, four feed pens A, B, C and D are illustrated schematically in FIG. 7. In addition to feed pens, a feedlot incorporating the cattle management system and method of the invention includes an alley 12 leading through a series of manually or power-operated gates 14, 16, 18 and a one-way gate 20 to a chute 22.

Alley 12 leads from an alley 24 which communicates with both feed pens and receiving and holding pens, where cattle are received and held for a short period upon their delivery to the feedlot from a producer. The intersection of alley 24 and the alley 12 leading to the chute 22 is gated as indicated at 26 and 28 to control the admission of cattle into alley 12 leading to the chute and to control the exit of cattle from sorting pens indicated at 30.

The gates 14, 16 and 18 subdivide the upper curved portion of alley 12 into cattle holding sections 190, 192 of about 40 head apiece so as to control the delivery of cattle into a crowding section 32 through crowd gate 18. Crowding section 32 narrows from its entrance to the one-way gate 20 so that cattle are forced single file through the gate 20 and into the chute area 22 which is a single-file chute.

Chute section 22 is subdivided into a series of longitudinally arranged stations 34, 36, 38, 40 and 42. These five stations are separated from one another and from the entrance 44 to the chute by entrance and exit gates 46, 48, 50, 52, 54, 56. The stations defined by these gates are only large enough to receive one animal at a time. The opening and closing of these gates are controlled by position sensors such as photoelectric cells under computer control to control the one at a time movement of animals through the chute. A larger scale depiction of the chute will be seen in FIG. 5.

Just downstream of the single-file chute are a series of the previously mentioned sorting pens 30, there being nine such pens illustrated in FIG. 1, including pens 30A, 30B, 30C, 30D, 30E, 30F, 30G, 30H and 30I. Below these pens in FIG. 1 is an alley 58 leading from the left-hand pen exits to the alleys 12 and 24. In addition, there is a single-file narrow alley 60 between the left-hand series of sorting pens 30A, 30C, 30D, 30E, 30G and the right-hand series of sorting pens 30B, 30D, 30F and 30H. From the layout of FIG. 1 it will be apparent that any animal proceeding through the chute and not sorted into one of the sorting gates 30A-30H will automatically end up in sorting pen 30I.

Alley 60 is normally isolated from the entrances to each of the eight sorting pens 30A-30H by a computer-operated entrance gate 62 at the entrance to each sorting pen. It will be noted that there is no entrance gate to the final sorting pen 30I. Each sorting pen also has an exit gate 64 at its opposite end opening into an alley used to direct the cattle from the sorting pens to another destination to be described in greater detail below. The exit gates 64 on pens 30A, 30C, 30E and 30G on the left-hand side of the alley 60 in FIG. 1 open into an alley 66 leading through control gates 68, 70 back to alley 58 where cattle can be directed either back through alley 12 or into alley 24 leading to the feed pens.

Each station of the single file chute 22 is set up either to prepare each animal for measurement or processing, or to actually measure or process the animal. For example, in FIG. 1, station 34 is termed the "get ready" station where one animal is admitted from the chute entrance area 44. Once the animal enters the "get ready" station 34, gate 46 closes and gate 48 remains closed so the animal remains isolated at that station. Then gate 48 is opened so that the animal enters the next station 36. Station 36 is where certain external dimensions of each animal are measured. This is preferably done through a video-imaging device or scanner suitable for this purpose such as one known commercially as an MSI Scanner available from Cattle Scanning Systems (C.S.S.) of Rapid City, S. Dak. Another video-imaging measurement system for cattle is disclosed in Hayes, U.S. Pat. No. 4,745,472.

After the animal's external dimensions are measured, gate 50 is opened and the animal proceeds into the third station 38 in the chute which contains a scale on which the animal is weighed. The scale used can be any of a number of commercially available scales but should be capable of generating an electronic signal for recording the weight at a remote location. Also at the scale station or at another desired station, an electronic identification (ED) tag is attached to the animal's ear. This EID tag remains attached to the animal throughout its residence in the feedlot and its shipment to the packing plant where it is removed upon slaughter. Through this EID tag, the animal can not only be identified but its location can be tracked and its measurement and performance data correlated to the animal throughout the duration of its feedlot stay, through its shipment to the packing plant, and until slaughter. One suitable EID tag for this purpose is manufactured by Allflex International and is described in greater detail in U.S. Pat. No. 5,315,505, issued May 24, 1994, to the assignee of the present application. The disclosure of U.S. Pat. No. 5,315,505 is incorporated herein by reference. The Allflex ED tag is a transponder which operates through a nearby antenna and an integrator reader also available from Allflex International. Each EID tag emits a signal unique to the animal to which it is attached, which is electronically "read" by the antenna and communicated to a host computer via a computer interface unit.

After an animal's weight is recorded and its EID tag attached, it moves through gate 52 to the next measuring station 40 where its internal backfat content is measured using an ultrasound measuring means and technique. For this purpose, the animal must be held fairly still, station 40 is a "squeeze chute", well known in the feedlot industry. The squeeze chute has a rear gate that pushes against the rear of an animal while its head is stabilized in a "head catcher". The ultrasound backfat measuring system used at station 40 is one that has been adapted from the experimental system used by Professor John Brethour at Kansas State University's Fort Hays Experiment Station, described in the September, 1994 issue of *DJ Feeder Management* magazine.

After backfat measurement, the gate 54 is opened and the animal proceeds to station 42 for processing. Station 42 is also a squeeze chute. Typically, processing at station 42 will include individual drug administration, growth hormone implantation, castration and dehorning. After processing, the chute gate 56 is opened and the animal is sorted into one of the sorting pens in a manner to be described hereinafter.

The enlarged schematic version of the single-file chute 22 shown in FIG. 5 is sufficiently similar to the chute 22 shown schematically in FIG. 1 that the same reference numerals will be used in describing both chutes. With reference to FIG. 5, it includes the same five processing and measuring stations 34, 36, 38, 40 and 42 as in FIG. 1. However, at the downstream end of the chute 22 of FIG. 5 there are only seven sorting pens 30 shown and designated sort pens 1-7, rather than nine such pens as shown in FIG. 1.

As shown most clearly in FIG. 5, the single-file chute includes at its downstream end just downstream of chute exit gate 56 from the processing station 42 a pair of access gates 72, 74 for the admission of feedlot personnel into the chute when necessary. These gates may be manually operated.

From FIG. 5 it will also be apparent that sorting into one of the several sorting pens is accomplished after each animal proceeds through all five stations of the chute by opening an entrance gate to one of the sorting pens while the others remain closed. Thus, for example, if an animal is to be sorted into sorting pen 3 in FIG. 5 its entrance gate 62 would open to the position 62a shown while the entrance gate 62 to all other sorting pens remain closed, thereby directing the animal into sorting pen 3.

As previously mentioned, each sorting pen entrance gate 62 and each of the chute gates 46, 48, 50, 52, 54 and 56 is operated via position sensors indicated schematically at 76 in FIG. 5 in conjunction with a host computer 78 through chute gate interfaces indicated schematically at 80.

Similarly, sort pen entrance gates 62 are operated by the position sensors 82 controlled by the host computer 78 through the sort gate interfaces 84.

The measurement taken at each of the measuring stations 36, 38 and 40 of the chute, for each animal passing through the chute, transmits a signal indicative of the measurement for that animal through an appropriate interface to the host computer 78, where the measurement data is entered and stored for use in calculating various performance characteristics of the animal.

Each measurement is correlated with a specific animal through the animal's EID tag as it passes from station to station through the chute. More specifically, the video imaging measurement (VIM) data is transmitted through a VIM interface 86 to the host computer 78. Weight data for the same animal is transmitted from the scale at station 38 through a scale interface 88 to the host computer 78. Then the ultrasound backfat data for the same animal is transmitted through the USBF interface 90 to the host computer 78. Finally, any drugs administered to the animal or other procedures performed on the animal at the processing station 42 are transmitted through the processing interface 92 to the host computer where such data is correlated with the animal processed.

Reference is made to the aforementioned U.S. Pat. No. 5,315,505 for a detailed description of how animal health data and drug administration data would be entered into the host computer from a processing station for a given animal.

Figure 2:
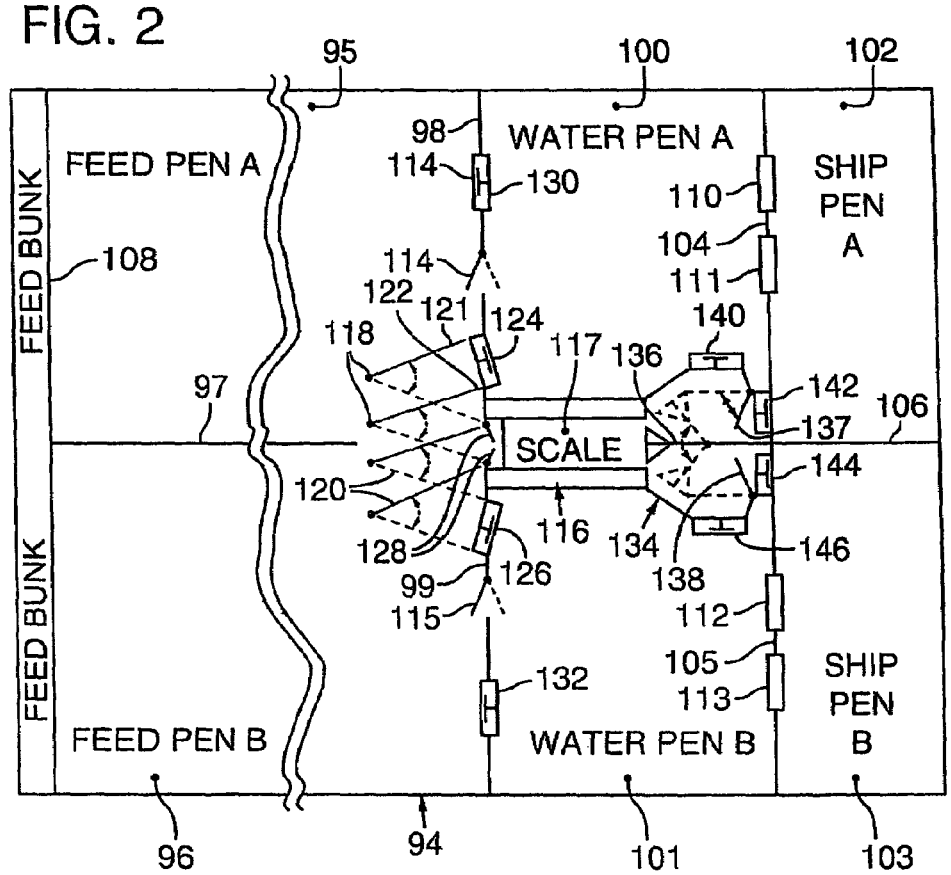
FIG. 2 is a schematic diagram of the layout of a pen sorter including feed pens, water pens and shipping pens for a feedlot in accordance with the invention.

With reference to FIG. 2, a pen sorter 94 is disclosed that is uniquely suited for use as an integral part of the system of the invention and for carrying out the method thereof. There could be one or several pen sorters 94 in a feedlot. Also, it is possible that the sorting portion of the pen sorter 94, which portion is to be described presently, could be designed as a portable unit that would be transported to a particular feed pen within the feedlot for use there within the 30 days or so prior to scheduled shipment of the group of animals within the feed pen so that the shipment date for each animal in the pen could be optimized for maximum feed efficiency and value.

In any case, the pen sorter is designed to enable weighing of individual animals on a frequent basis, such as daily or even more frequently, without removing the animals from their feed pens and without the need to send them back through the single-file chute described with respect to FIGS. 1 and 5.

The illustrated pen sorter 94 is subdivided into two feed pens 95, 96 designated feed pen A and feed pen B, separated by a partition or fence 97. Each feed pen in turn is also separated by partitions 98, 99 from adjacent water pens 100, 101, designated water pen A and water pen B. Water pens A and B are, in turn, separated from adjacent shipping pens 102, 103 by partitions 104, 105, the shipping pens being designated ship pen A and ship pen B. The ship pens in turn are separated from one another by another fence or partitions 106. Each feed pen includes a feed bunk 108 into which the daily feed ration of the animals in those pens is deposited and to which the animals in the feed pen have ready access. The water pens and ship pens are provided with respective watering troughs 110, 111, 112 and 113 so that the animals within those pens can access drinking water as desired.

The heart of the pen sorter 94 is its array of gates for directing animals in the feed pens A and B to desired locations within the larger confines of the pen sorter 94, on an individual animal basis, based on measured performance characteristics of each animal, other data such as market conditions, and a desired shipping date.

First it should be noted that animals within feed pen A are free to pass between such pen and its adjacent water pen A through a two-way gate 114 to access feed and water as desired. The same is true with respect to animals within feed pen B through a two-way gate 115 between feed pen B and water pen B. However, unless desired by feedlot personnel or dictated by the management system, cattle cannot pass from one feed pen to another or from one water pen to another and cannot pass from either water pen into either shipping pen.

A single scale stall 116 is positioned between water pen A and water pen B and is sized to accept one animal at a time. The scale stall is equipped with one scale at 117, which can be of a type similar to that used in the scale station of the single-file chute as previously described. The scale is set up to transmit automatically the weight reading of an animal through a suitable interface to the host computer. To identify the animal being weighed, the stall is also equipped with an EID tag identification means as previously described for receiving and transmitting the identification of an animal being weighed to the host computer.

Access to the scale stall is either from feed pen A or feed pen B, as desired, through one of two shuttle gates 118, 120. Both shuttle gates 118 and 120 comprise a pair of parallel gate arms 121, 122 which move in unison from a scale entrance position, as shown with respect to shuttle gate 120, to a scale blocking position, as shown with respect to shuttle gate 118 in FIG. 2. When in its scale blocking position, each shuttle gate has its arms 121, 122 directed toward a one-way gate leading into the adjacent water pen. For example, feed pen A shows shuttle gate 118 with its shuttle arms in a position for directing animals through the one-way gate 124 into water pen A. When shuttle gate 120 is in a comparable position, its arms would direct cattle through a one-way gate 126 into water pen B. Thus, depending on the position of shuttle gate 1118, animals from feed pen A can be directed either through one-way gate 124 into water pen A or into the scale stall 117. A one-way gate 128 at the entrance to the scale stall prevents an animal that has entered the scale stall from backing out. Similarly, an animal within feed pen B can be directed by shuttle gate 120 either into the scale stall 117 to be weighed or through the one-way gate 126 into water pen B.

Of course, it will apparent that an animal in feed pen A or in feed pen B can at any time pass through the two-way gates 114 and 115 between those pens and their respective water pens A and B, and back again to their respective feed pens. It will also be apparent that any animal within water pen A can also pass through a one-way gate 130 back to feed pen A. However, unless other control gates are operated, an animal in water pen A cannot pass to either shipping pen A or shipping pen B or into feed pen B. Similarly, any animal in water pen B can pass through either the two-way gate 115 or a one-way gate 132 back to feed pen B but cannot pass into shipping pen B, feed pen A or water pen A without operation of appropriate control gates.

Once an animal is within the scale stall 116, it must pass forwardly out of the stall through a complex array of sorting gates indicated generally at 134 into one of four pens, either water pen A, shipping pen A, water pen B, or shipping pen B. The operation of the sorting gate array 134 is under computer control. The scale stall 116 is provided with an EID tag antenna to identify the animal within the scale stall to the computer system, which then determines which pen the animal is to proceed to from the scale stall, after which the computer operates the sorting gate array 134 in a manner to direct the animal to the appropriate pen.

Sorting gate array 134 includes three controllable shuttle gates 136, 137 and 138. In addition, it includes a one-way gate 140 leading from the sorting area just downstream from the scale stall into water pen A, a one-way gate 142 leading from the same sorting area into shipping pen A, a third one-way gate 144 leading from the sorting area into shipping pen B and a fourth one-way gate 146 leading from the sorting area into water pen B.

The following will illustrate that an animal in, for example, feed pen A can be directed through the scale stall 116 and then either back to feed pen A, to feed pen B, to shipping pen A or to shipping pen B. The same is true with respect to an animal in feed pen B. Thus, pen sorter 94 is capable of effecting a four-way sort.

To illustrate, an animal in feed pen A with the shuttle gate 118 in the position shown, can pass freely between feed pen A and water pen A and back to feed pen A. However, with the shuttle gate 118 shifted to its position shown in dashed lines in FIG. 2, an animal in feed pen A will be directed through the one-way gate 128 into the scale stall 116 where it will be weighed and identified to the computer through its EID tag. The computer will then determine to which pen it should be sorted from the scale stall and actuate the appropriate gates to accomplish the desired sort. For example, if it is desired to return the animal to feed pen A, sorting gate 136 is shifted downward to its dashed line position shown thereby allowing the animal to move through the sorting area and through the one-way gate 140 back to water pen A where it can move freely back to feed pen A, either through the two-way gate 114 or the one-way gate 130.

If it is desired that the animal be sorted from feed pen A to feed pen B, sort gate 136 is shifted upward to its dashed line position shown, allowing the animal to travel from the scale stall freely through the sorting area and one-way gate 146 to water pen B, from which the animal can move freely through either two-way gate 115 or one-way gate 132 to feed pen B.

If it is desired that the animal move from the scale stall 116 to shipping pen A, sort gate 136 is moved to its downward position in FIG. 2 and control gate 137 is moved to its upward position shown in dashed lines in FIG. 2, enabling the animal to travel through the sorting area and through one-way gate 142 into shipping pen A.

If it is desired that the animal move from the scale stall to shipping pen B, sorting gate 136 is moved upward, control gate 138 is moved downward to its dashed line position, and the animal can thus move freely through the sorting area and one-way gate 144 into shipping pen B.

From the foregoing it will be understood that animals within feed pens A and B can be weighed as frequently as desired and sorted four ways without moving the animals any appreciable distance. Thus the pen sorter 94 provides an ideal finishing pen for use in determining the exact day within a shipping window of several days when an animal should be shipped to the packing plant for slaughter to realize the maximum return on the investment in such animal, considering animal performance, market conditions and feed efficiency.

B. Cattle Management System and Process

Figure 3:
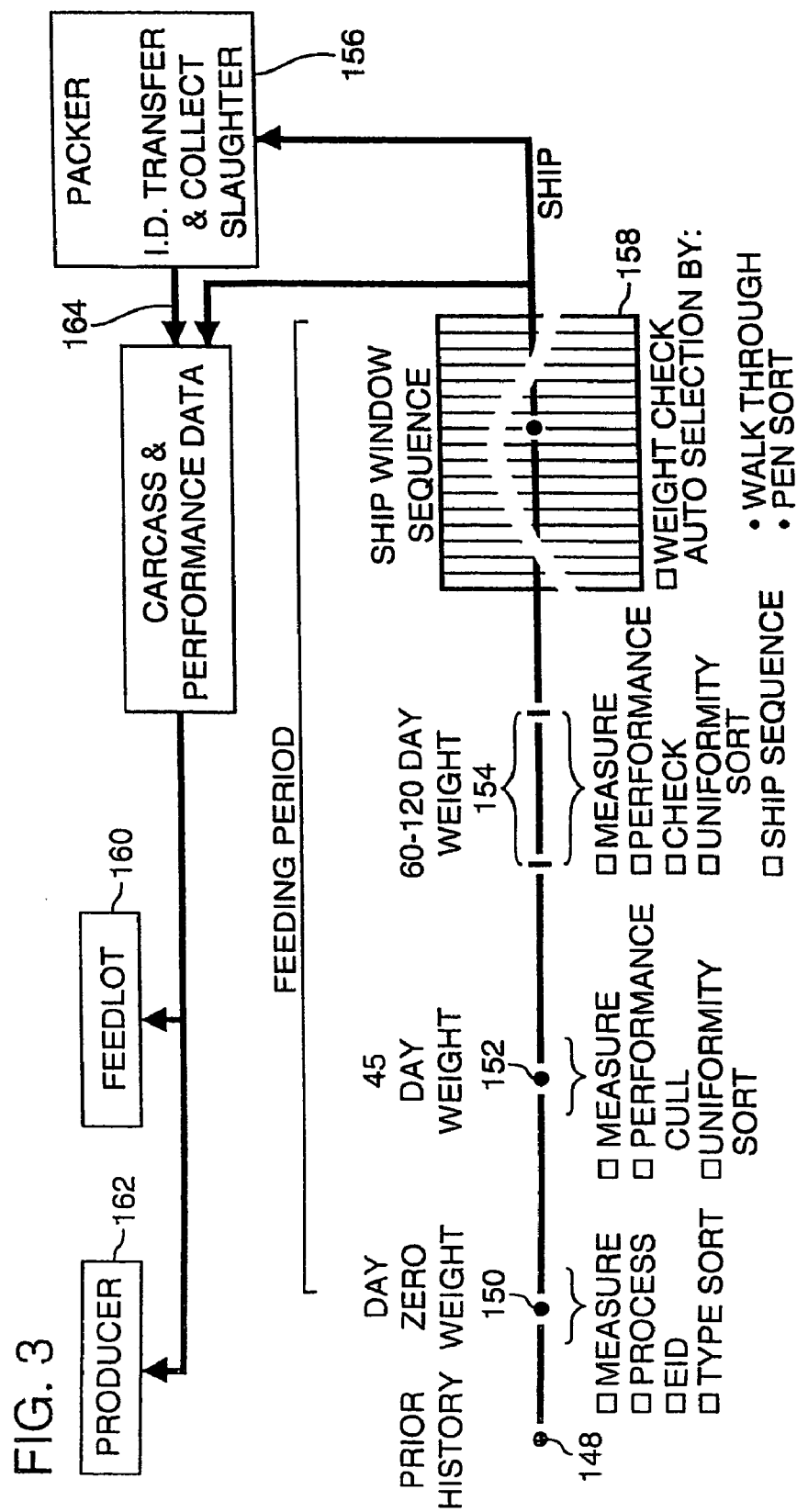
FIG. 3 is a cattle processing timeline to exemplify a method of processing and managing cattle in accordance with the invention.

FIG. 3 illustrates a hypothetical timeline in the management of cattle in accordance with the invention.

Upon arrival of a lot of cattle in the feedlot, or before, the prior history of the lot would be entered in the host computer 78, as indicated at 148. Such prior history data is illustrated, for example, in the cattle received report by "load" shown in FIG. 9A. The report indicates such things as the date the load was received, the load number, the number of head in the load, the sex of the cattle in the load and the average weight of the animals in the load. It also indicates cost information. It also gives information such as the age of the cattle, the breed, the type of pasture the load has been on and health, nutrition, stress and weather conditions applicable to the load. It also indicates the number of days the load has been feeding on pasture. Some or all of this data may be used in later calculations by the computer to determine the optimum end date (OED) or days to finish (DTF), of the group or individual animals in the group. This date is also sometimes referred to as the optimum marketing or shipping date.

On the day of their arrival, indicated on the timeline at 150, each animal in the load is measured, processed and electronically identified with an EID tag in the one-way single-file chute 22 previously described. Then, if desired, the measured and processed animals may be sorted into the sorting pens 30 in a rough sort by type (breed), weight, age, or a first estimated OED or DTF, although such a first "rough" first sort is optional.

From the sorting pens, the animals are moved to feed pens, either by sort or on an ad hoc basis, where they are fed for a period of time, such as 45 days as shown in FIG. 3, although possibly substantially longer than that.

If a 45 day weight or measurement is desired for the animals, they would be moved from their feed pens on the 45th day as indicated at 152 back through the single-file chute, where they would be remeasured. From the initial measurement and remeasurement data, the performance of each animal would be calculated by the computer, and its performance assessed. The animals would then be sorted into the sorting pens 30 according to their performance characteristics. Poorly performing animals would be culled from the group and removed from the feedlot operation as "salvage". The remaining resorted animals would be returned to the feed pens according to their sorts.

Then 60-120 days into the feeding period, indicated by the range 154 in FIG. 3, the animals from at least two feed pens at once would be moved from their pens back through the single-file chute for remeasuring once again on an individual basis. The data from these measurements together with prior data for each animal would be used by the computer to calculate a new OED or DTF for each animal and other performance criteria, such as average daily gain (ADG) and feed proration for each animal. From the single-file chute the animals would be resorted once again according to predetermined criteria such as DTF or OED. A projected shipping sequence for each animal could also be calculated at this time. Then the animals would be returned to the feed pens according to the newly determined sorts. The animals then could be removed from their pens for shipment according to their calculated shipping sequence. Whenever an animal is moved in the feedlot, its identification and data, via computer, moves with it. Its location at any time can be determined remotely by computer, and its performance data assessed.

Alternatively, a portable pen sorter of the type shown in FIG. 2 could be installed in the feed pen. Each animal would be carefully monitored and weighed, perhaps on a daily basis, until it reached its optimum shipping weight or value, at which time it would be shipped to the packer, indicated at 156.

Alternatively, animals within the feed pens could be sent to a finishing pen such as the pen sorter 94 shown on FIG. 2 where it would be confined, monitored and weighed frequently within a shipping window such as a 30 day shipping window. Within that shipping window indicated at 158, each animal as determined by frequent weight checks and market conditions, would be directed from its feed pen, such as feed pen A or feed pen B in FIG. 2, to appropriate shipping pen A or B when it is ready for shipment.

Alternatively, during an animal's shipping window, the animal could be weight checked simply by sending it back through the single-file chute periodically until it reaches its ideal shipping weight, at which time it would be shipped to the packer 156.

Alternatively, a specific shipping date for a given animal could be determined by issued inspection while the animals are within their 30-day shipping window.

When the animal leaves the feedlot, its EID tag travels with it. Its historical and performance data records would be maintained by the feedlot, indicated at 160, and also transmitted to the producer, indicated at 162. At the same time, the packer would record the carcass data for each slaughtered animal, identified by its EID tag, and transmit the carcass data, as indicated at 164, to the feedlot and producer for correlation with the animal's live performance data from the feedlot.

The correlation can be useful to the feedlot in projecting optimum end dates (OED), initial feed proration and production costs for future animals of a given type and similar history. This data can also be useful to cattle producers in determining which breeds and individual breeding animals are most desirable from the standpoint of market value and producing the best quality of beef. The important thing to note is that the performance of each animal is tracked on an individual basis from the time it arrives in the feedlot until the time it is shipped and slaughtered, when its carcass data is collected and correlated with its performance data for use by the feedlot and producer in managing future beef production.

Another important feature of the system is its ability to update an individual animal's performance projections on a daily basis. For example, the DTF for an animal will be current for the day the projection is assessed. The same is true for other projections such as projected weight, etc.

Figure 4A:
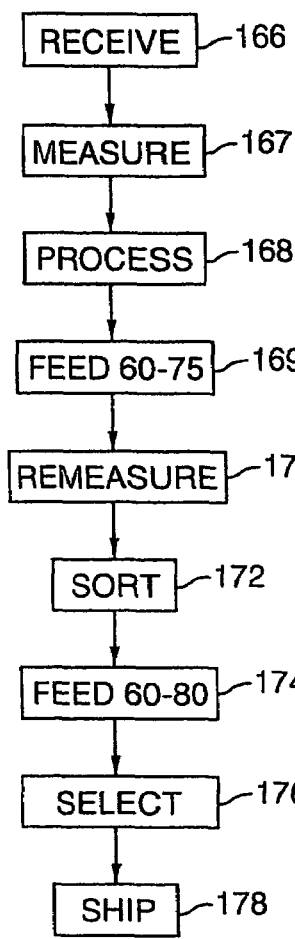
FIGS. 4A, 4B, and 4C are cattle processing diagrams illustrating three alternative methods of processing and managing cattle in a feedlot in accordance with the method of the present invention.
Figure 4B:
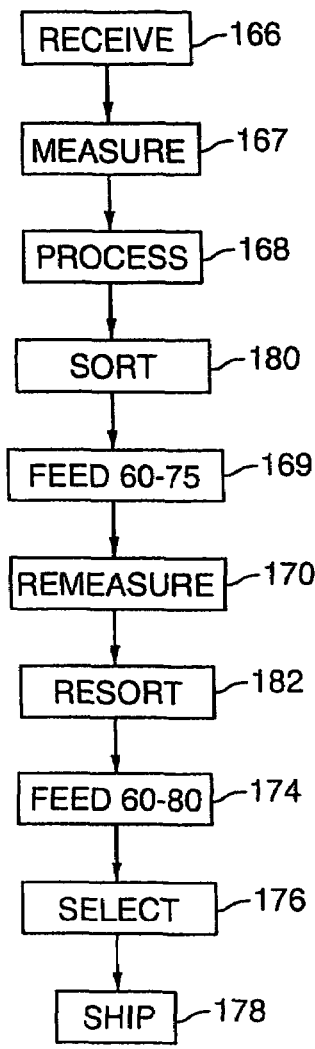
Figure 4C:
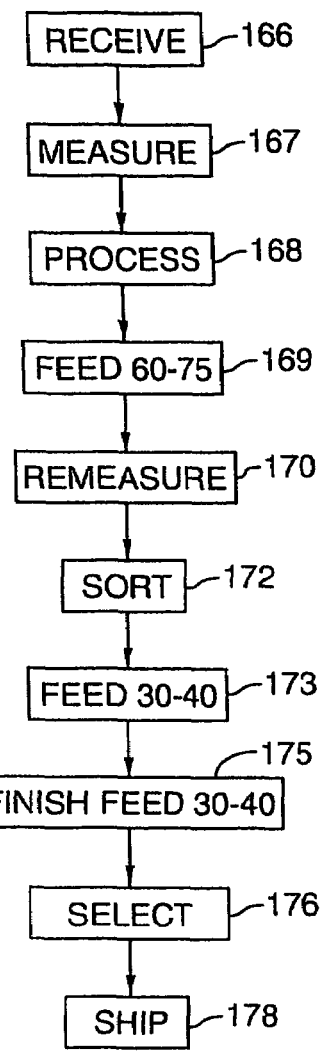

Although FIG. 3 illustrates one possible processing sequence of cattle including measuring and remeasuring steps and sorting and resorting steps for optimum feed efficiency and return, many other sequences are possible as illustrated in FIGS. 4A, 4B and 4C. For example in the sequences of FIGS. 4A, 4B and 4C the 45 day remeasurement is eliminated and instead a single 60-75 day remeasurement and uniformity sort are performed.

Referring to FIG. 4A, a load of cattle is received in the feedlot at 166 and within a few hours, measured at 167 and processed at 168 in the single-file chute. From the chute they are directed into the feed pens at 169 without an initial sort. They are fed in the feed pens for 60-75 days, then returned to the single-file chute for remeasuring at 170 and possibly reimplantation of a growth hormone, if necessary. After remeasuring, the animals undergo a uniformity sort as determined by the computer, and directed into the appropriate sorting pens 172. Upon completion of the sorting operation, they are returned to the feeding pens 174 according to their sort groups and there fed for a period of 60 to 80 days. As the cattle within the feed pens approach their individual optimum end dates they would be selected for shipment either visually, by remeasurement at the single-file chute, or by frequent reweighing in a portable pen sorter of the type shown in FIG. 2. Following selection at step 176 the animal would be shipped as at 178 to the packer.

The processing sequence of FIG. 4B for an individual animal is the same down through the initial receiving, measuring and processing steps. However after measuring and processing, according to FIG. 4B there is an initial sort step 180 that can be a rough type sort as in FIG. 3 or can be based on a first rough estimated optimum end date for each individual animal. Following the first sort 180, the animals are directed by sort group into feed pens at 169 for a feeding period of 60-75 days. At the end of the 60-75 day period the animals are removed from their pens, either individually or in groups, and returned to the single-file chute for remeasuring at 170.

After remeasuring in the single-file chute, each animal is resorted at 182 by the computer, which opens the appropriate sorting gates of the sorting pens 30. From the sorting pens, the animals are redirected back to the feed pens at 174 and placed into the pens according to their sorting groups. They remain in the feed pens for a period of 60-80 days, after which they are individually, or by group, selected for shipment, according to their last calculated OED. As previously indicated, this selection for shipment can be fine-tuned through the use of either a portable pen sorter or the pen sorter 94 of FIG. 2. After selection, the selected animals are shipped at step 178 to the packing plant for slaughter, where the carcass data and EID tag are collected.

The optional cattle processing procedure of FIG. 4C is the same as the procedure outlined in FIG. 4A down through the initial sorting step 172. However, thereafter the animals, according to the procedure in FIG. 4c, are directed back to the feed pens according to sorting group at step 173 for a feeding period of only 30-40 days. Thereafter, the animals, or at least selected animals, from the feed pens are removed to finish feed pens, such as pen sorters 94 in FIG. 2, for a finish feeding step 175 for an additional 30-40 days, which represents the shipping window 158 indicated in FIG. 3. Within the finish feeding pens, the animals can be sorted, resorted, weighed, reweighed and selected on an individual animal basis for sorting to one of the two shipping pens A and B for shipment to the packer at step 178.

C. Cattle Processing Example

FIG. 7 illustrates, in greater detail, a representative cattle processing sequence in a feedlot according to the system and process of the present invention. Steps in the processing sequence are numbered 1-9 along the left-hand side of FIG. 7.

In step 1, as indicated at 184, several lots of cattle arrive at the feedlot at about the same time, indicated as lots 1-. When they arrive, the previous history data of the lots and individual animals in the lots is entered into the host computer by data entry means (not shown) such as a computer keyboard. The previous history, as already mentioned, may include information such as shown in FIG. 9A.

According to step 2, after the cattle arrive they are directed into receiving or holding pens 186, typically by lot, where they are held just prior to initial processing. The time spent in the holding pens 186 will depend on when the lots arrived in the feedlot. For example, when they arrive in the middle of a night, they would be retained in the holding pens until feedlot personnel arrive early the next morning to process them. When ready for processing, the cattle from the holding pens 186 are directed through the appropriate alleys to the one-way single-file chute 22 where they are one-by-one led through the various chute stations, sequentially, including the get ready station 34, the video image measuring station 36, the weighing station 38 and the ultrasound backfat measuring station 40. During this process the EID and visual eartags are applied as well, and the measurement data from each of these stations is transmitted through the appropriate interfaces to the host computer 78 for recording, collection and storage. At the processing station 42 each animal is implanted with a growth hormone, given medication as needed, and dehorned and castrated as needed.

Using available information and data on the group being processed and the individual animals in the group, an initial optimum end date (OED) is determined, either through calculation by the computer or by the operator. A marketing target grade for each animal and for the group (an average) is also assigned, either by the operator from a list of data or through calculation by the computer, depending on the capability of the computer program used. In addition, at this point a projected feed intake for each animal is calculated and assigned and used in prorating the total feed ration used by a group of animals within a single feed pen, so that a fairly accurate cost of feed per animal can be calculated and assessed to the owner.

Referring to FIG. 25, the process and formulas for calculating "days to finish" (DTF) is illustrated, followed by an example calculation based on hypothetical measurements of an animal passing through the single-file chute.

Referring to FIG. 26, an alternative method of calculating DTF for an individual animal is disclosed. Following the figure is an example calculation based on hypothetical measurements taken at two different measuring dates during an animal's feeding period at the feedlot.

Using the method of FIG. 25, an animal arriving at the feedlot, after being measured in the single-file chute, is calculated to have a projected DTF of 141 days. This represents the total number of days the animal is projected to be at the feedlot before it is ready for shipment to the packing plant. However, according to FIG. 26, the same animal using the different method of FIG. 26, is calculated to have a DTF of 165 days, based on its initial measurements upon arrival at the feedlot.

In Table 1 there are set forth limiting factors to DTF projections based on maximum and minimum live weight for the animal. An example calculation follows. According to the calculation, if a maximum hot carcass weight of 800 pounds and a minimum hot carcass weight of 500 pounds is desired in the end product, the maximum live weight of the animal should be 1230 pounds and the minimum live weight of the animal should be limited to 768 pounds. Thus, if the OFW (optimum finish weight) as used in the example calculation following FIG. 25 results in a maximum live weight that exceeds 1230 pounds or a minimum live weight of less than 768 pounds, the maximum or minimum live weights from the example calculation of Table 1 should be used in the FIG. 25 calculation rather than the optimum finish weight (OFW) originally used.

It will be noted that the formula and calculation of FIG. 25 includes a "Cornell Cattle Systems" formulation. This is a well-known formula in the cattle industry which includes inputs of OFW, condition score (backfat measurement), current weight, ration, environmental factors, feed additives and input program used.

Figure 27:
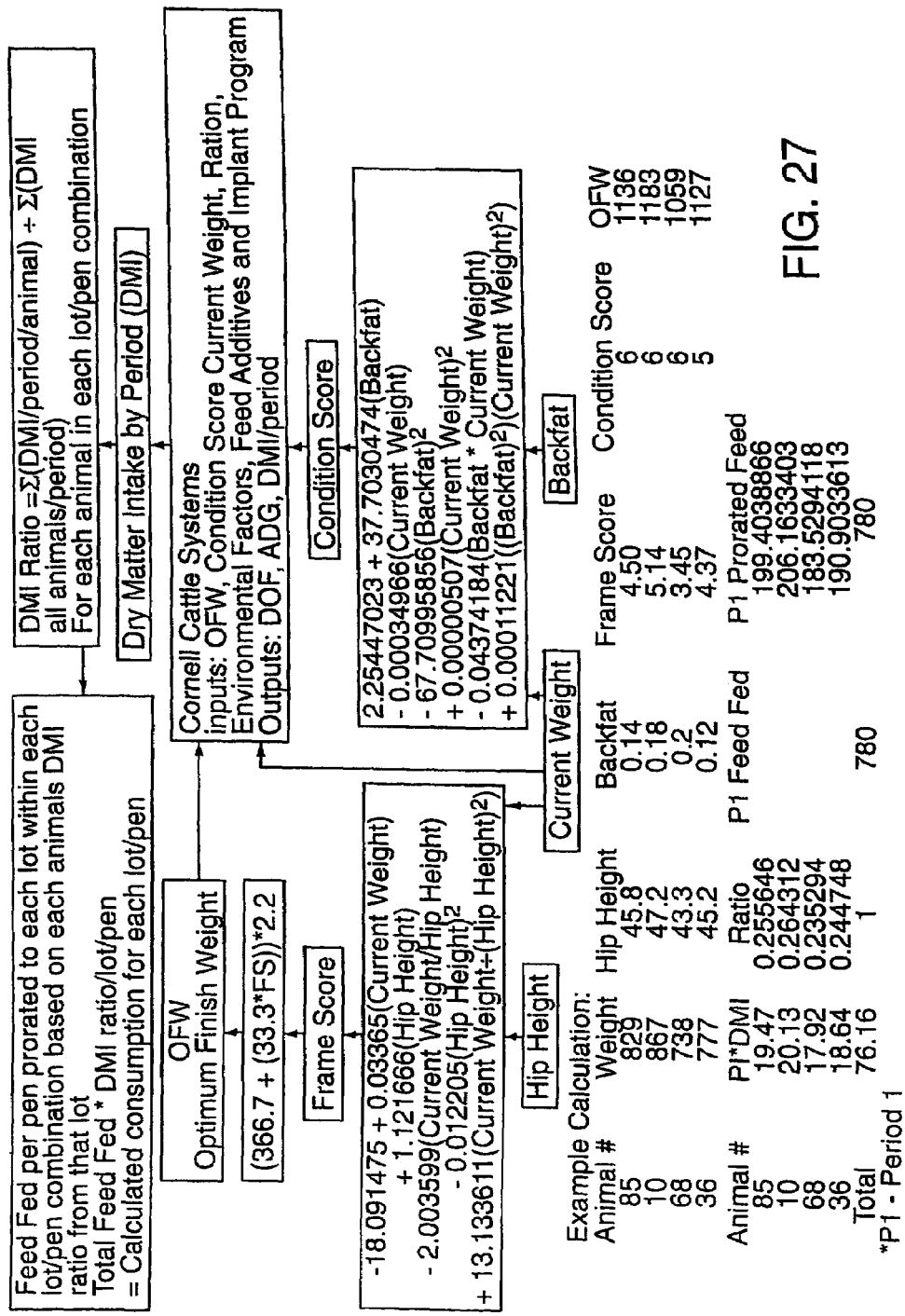
FIG. 27 is a flow diagram illustrating the process of determining feed proration to individual animals following a first set of animal measurements in the feedlot.
Figure 28A:
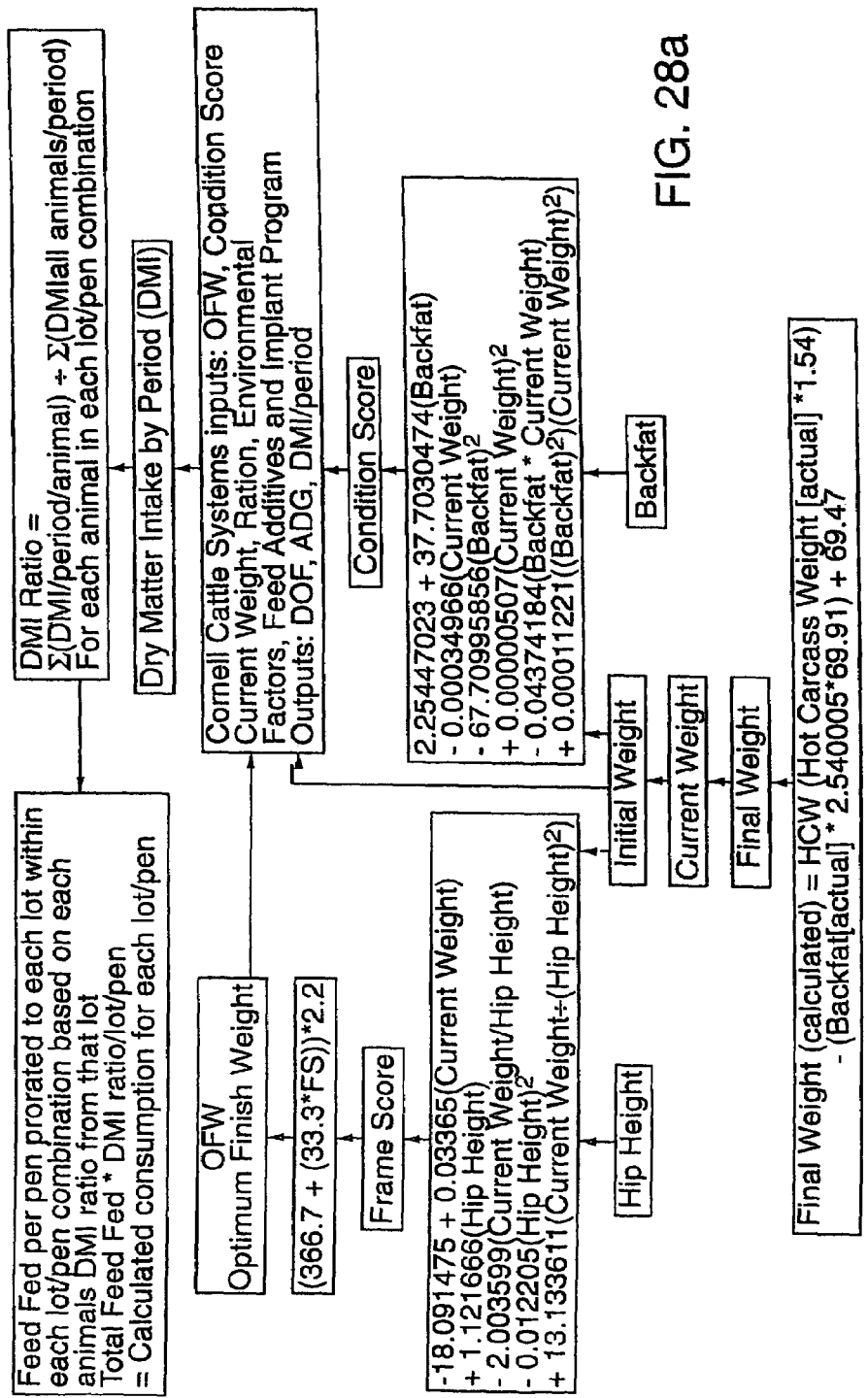

FIG. 27 shows the calculation and the process of calculating feed proration to each animal as determined following the first set of measurements at the single-file chute. FIG. 27 is followed by an example calculation using the formula and method indicated in the figure. In the figure DMI indicates dry matter intake for a given feed period and is indicated hereinafter as (DMI). In the same method of calculation the ADG indicates the average daily gain for a given animal. All other measurements used in the formula will be self-explanatory. As indicated in the formula, the frame score is determined by a formula using both hip height and current weight. The condition score for an animal is determined using both the backfat measurement and current weight. In the example, the proration of feed fed in a given period (P1) is calculated for each animal. From the calculation a proration ratio is indicated and applied to the 780 total pounds of feed fed to a pen of four animals during the P1 feed period, resulting in a feed period total proration of feed among the four animals as indicated in the last column of the calculation. It will be noted that of the four animals, the proration ranges from a low of 190.9 pounds to a high of 206.2 pounds. This feed proration formula and calculation is used only for the first feed period following the first measurement of the animals. Following the second and subsequent measurements, a different feed proration formula and calculation is used as indicated in FIGS. 28a and 28b.

Figure 29:
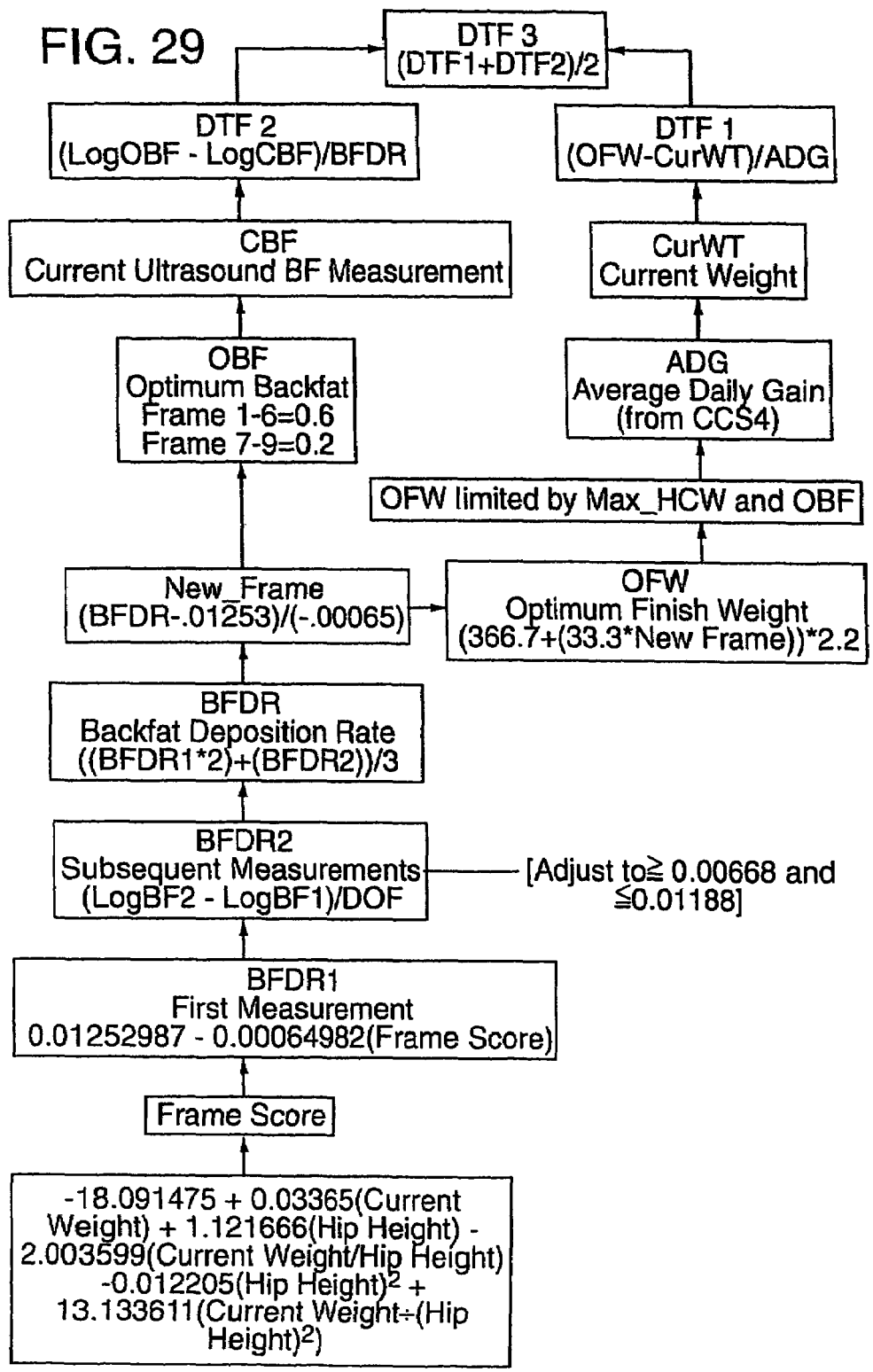
FIG. 29 is a flow diagram showing how calculations of "Days to Finish" from FIGS. 25 and 26 can be used to create an average "Days to Finish" for projecting when an individual animal will be ready to ship from a feedlot.

FIG. 29 illustrates how the calculations of DTF from 2FIGS. 25 and 26 (DTF1 and DTF2) can be used to create an average DTF (DTF3) for use in projecting when an individual animal will be ready to be shipped from the feedlot. The numbers used in 6FIGS. 25, 26 and FIG. 29 are coefficients that are obtained empirically from experience feeding cattle at a prototype feedlot managed in accordance with the method and system of the invention. The coefficients are defined and correlated with the coefficient numbers used, in Table 2.

TABLE 1

Limiting Factors to DTF Projections
Maximum Live Weight (Max_LW)
Minimum Live Weight (Min_LW)

Max_LW = (Max_HCW * 1.54) − (OBF * 2.540005 * 69.91) + 69.47
Min_LW = (Min_HCW * 1.54) − (OBF * 2.540005 * 69.91) + 69.47
Maximum Hot Carcass Weight (Max_HCW): User Input
Minimum Hot Carcass Weight (Min_HCW): User Input
Optimum Backfat (OBF): User Input TABLE 1-continued Limiting Factors to DTF Projections
Maximum Live Weight (Max_LW)
Minimum Live Weight (Min_LW)

Example Calculations:

User Inputs:

| | |
|---|---|
| Max_HCW: | 800 lbs |
| Min_HCW: | 500 lbs |
| OBF: | 0.40 in. for frame score 4 |
| Max_LW = | (800 * 1.54) − (0.40 * 2.540005 * 69.91) + 69.47 = 1230 lbs |
| Min_LW = | (500 * 1.54) − (0.40 2.540005 * 69.91) + 69.47 = 768 lbs |

TABLE 2

DTF Calculation Coefficients

Frame - Linear Regression Equation

| | |
|---|---|
| C-1 | Intercept for Regression Equation (−18.091475) |
| C-2 | Estimate for Weight parameter (0.03365) |
| C-3 | Estimate for Hip Height parameter (1.121666) |
| C-4 | Estimate for the parameter of Current Weight divided by Hip Height (2.003599) |
| C-5 | Estimate for the parameter of Hip Height Squared (−0.012205) |
| C-6 | Estimate for the parameter of Current Weight divided by Hip Height Squared (13.133611) |

BFDR-1 Linear Regression Equation

| | |
|---|---|
| C-7 | Intercept (0.01252987) |
| C-8 | Estimate for Frame Score Parameter (−0.00064982) |

BFDR-2 Logarithmic Regression Equation

| | |
|---|---|
| C-9 | Lower limit Fat Depostion Rate (0.00668) |
| C-10 | Upper limit Fat Depoation Rate (0.01188) |

BFDR - Weight Average Calculation of BFDR
New Frame

| | |
|---|---|
| C-11 | Upper Deposition Rate (−.01253) |
| C-12 | Lower Deposition Rate (−.00065) |

OBF - Conversion Tables for Frame to Back Fat
DTF1 - Logarithmic Regression Equation
OFW - Regression Equation

| | |
|---|---|
| C-13 | Intercept (366.7) |
| C-14 | Estimate for OFW (33.3) |
| C-15 | Pounds to Kilogram Conversion Factor (2.2) |

ADG - Cornell Model Output of ADG

Figure 30:
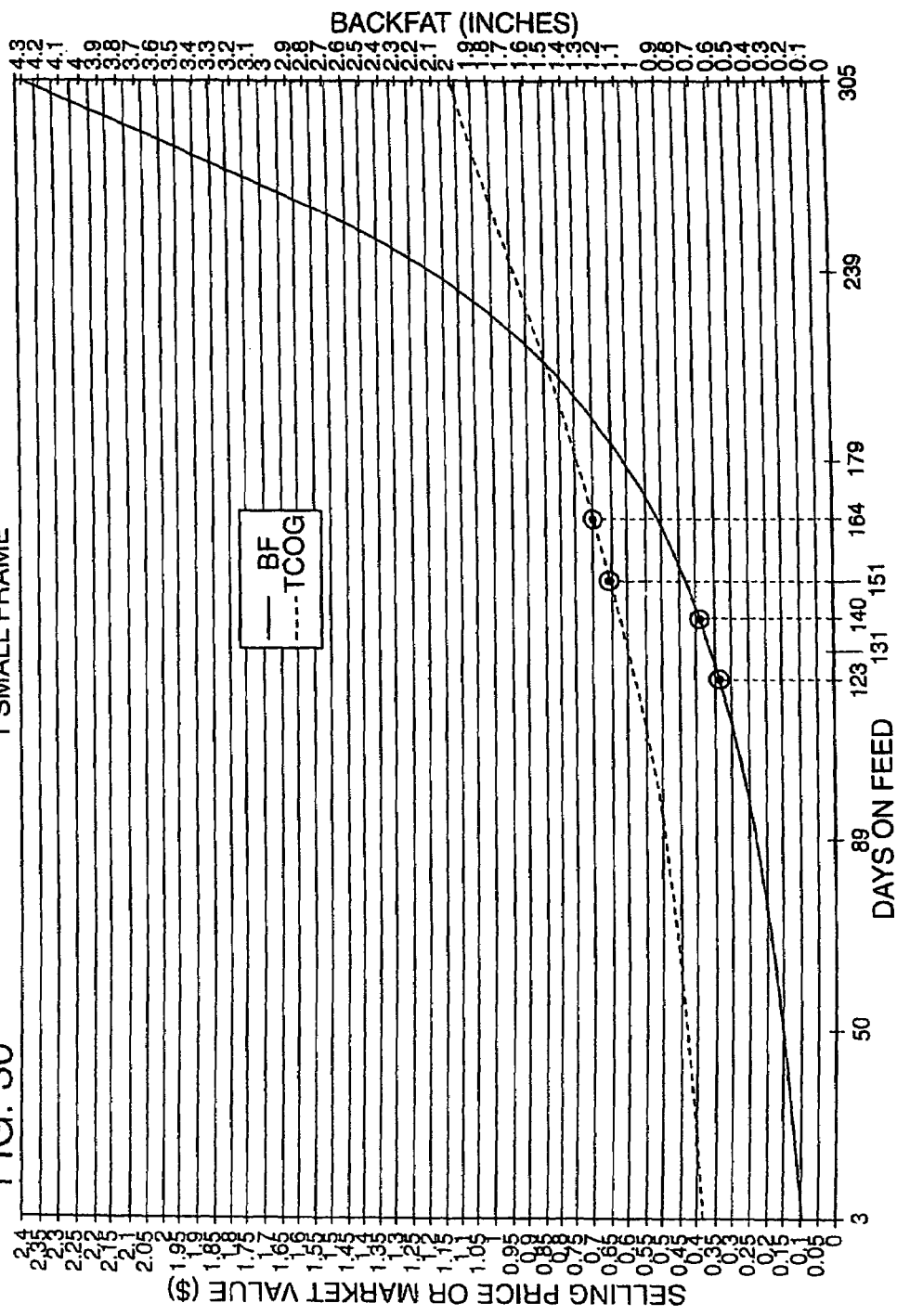
FIG. 30 is a graph plotting selling price against animal backfat along two different curves during the time that an animal is on feed in a feedlot.

The following example illustrates how a final DTF calculation can be made for determining exactly when an animal should be shipped to slaughter, based on economics (value) and the prior DTF1 and DTF2 calculations of FIGS. 25 and 26. FIG. 30 is a graph that plots selling price (left-hand vertical line) and backfat on the animal (right-hand vertical line) along two different curves, in terms of the number of days the animal is on feed (DOF). From the calculations and plotting it is determined, in the example, that the point P4 on the backfat curve should be selected for shipment of the animal. This is at 140 days into the feeding period, the most economical point for shipping. Beyond that point, the animal's backfat will exceed 0.7 inches, resulting in the animal's carcass being degraded and thus becoming less valuable. The P1 and P2 end points would result in a carcass with too much backfat. The P3 endpoint would be below the backfat limit, so the animal can be fed beyond this point to increase its value.

EXAMPLE

INDIVIDUAL ANIMAL FINAL DTF CALCULATION

1) Input: Sex, Beginning Weight, OFW, Mature Weight, Breed, Hide, Age, Number of Head, Purchase Date, Hip Height, Calculated Frame Score, Initial Back Fat, Flesh Condition Code, Ration Composition/Energy, Environmental Factors.
2) Run Cornell Calculation Method One→Outputs for 6 periods on feed.
   Average Weight for Period.
   Dry Matter Intake for Period.
   ADG for Period
   DOF for Period
3) Calculation Gain for Period=ADG□DOF Period.
4) Period Feed Cost of Gain=DMI×DOF Period×Cost Per Pound+(Yardage cost per day×DOF Period÷Gain for Period)
5) Feed Interest Cost of Gain=Calculated for all except period one
6) Cattle Interest Cost of Gain for Period I=Daily interest rate×number of days in period=$÷the gain (calculated by average weight for period less initial weight)
7) Total nos. 4)+5)+6)=Total incremental Cost of Gain
8) Calculate and project for all 6 periods and plot projection graph
9) Plot OFW (Mature Weight) on TCOG line at P-1 at 151 DOF to reach 1006 pounds (28% Body Fat Target).
10) Plot the location where total incremental COG=Selling Price ($0.70/lb) on TCOG line at P-2 at 164 DOF to reach 1041 pounds.
11) Plot Back Fat Deposition Rate-use Initial Back Fat in the DTF2 Method Two calculation to determine the rate. The rate is used to compound the initial back fat measurement daily for the entire period and is plotted on the graph as BF.
12) Plot the 0.6 BF Target on the Fat deposition rate line at P-3 for 0.6 at 123 DOF to reach 920 pounds.
13) Final DTF Number in this case is P-4, which is the predetermined maximum Back Fat limit which is selected by the computer program. This is calculated to be 140 DOF at 975 pounds. The final DTF number cannot be P-1, P-2 or P-3 because:
    a) P-1 exceeds Maximum BF to incur a dollar discount.
    b) P-2 exceeds Maximum BF to incur a dollar discount as well as causing incremental cost of gain to exceed selling price resulting in decreased profit.
    c) P-3 is the original BF target but, since the animal is still making profit, it should be fed longer.

As soon as the animal exits the processing station 42 to enter the sorting pen area, the computer 78 has calculated the indicated characteristics of the animal, such as projected OFW, projected ADG, projected DTF and a projected feed proration ratio according to the formula and process outlined in FIG. 27. At this point a sort may or may not be done as indicated at step 3A of the management process. If a sort is to be done, it would likely be a rough sort by animal type, weight, or OED. At this point it would usually be too early to cull animals from the feedlot because there is no performance data yet accumulated on any animal.

In the illustration of FIG. 7 the measured and processed animals would go directly to step 4 of the process, which is directly to one of four feed pens 188, feed pen A, feed pen B, feed pen C or feed pen D. There they would be provided a selected feed ration and water for a selected period that may range from 45-75 days but more typically in the 60-75 day range. During this first feeding period each animal's records are maintained and the cost of the feed ration delivered to each pen would be prorated among the individual animals for assessment to their respective owners.

At the end of the first feeding period, two or more of the feed pen cattle groups in the feed pens A-D are selected for remeasurement at the same time. This selection may be based on one or more of several factors such as the similarity of their group average OED or DTF, breed type, marketing target yields or other factors. Each animal in the selected groups is directed back through, for example, the alley 24 from its feed pen through the gates 26, 28 and back through the alley 12 leading to the single-file chute. Once within the alley 12, the animals are led into two different holding sections of the alley as defined by the manually operated alley gates 14, 16, 18 defining holding sections 190, 192. Each of the holding sections 190, 192 is capable of holding approximately 40 head of cattle. From the holding section 192 the cattle are led through a hydraulically operated crowd gate 18 into the crowding section 32 where cattle are directed one-at-a-time through a hydraulically powered one-way gate 20 leading to a single-file entrance section 44 into the one-way chute 22.

Then the animals are admitted one at a time and single file into the chute 22 where they are measured externally and internally, and weighed once again. In the processing section 42 the animals may also be reimplanted with a growth hormone as needed. The measurement data for each animal is automatically entered into the computer 78 via data entry means coupled to the measuring apparatus and there correlated with the EID of the animal.

With the historical data, original measurement data and the remeasurement data for each animal, that animal's performance through the first feeding period can be accurately calculated and gauged, much more so than with the projected performance data from the original measurements alone. Thus, upon remeasurement, each animal's ADG, OFW and DTF (or OED) is recalculated and used as the basis for a prediction of future performance and a shipping date or at least shipping window, using the methods previously outlined with respect to FIGS. 25 and 26, and Table 1. In addition, each animal's feed proration is recalculated using the method and formula outlined in FIGS. 28a and 28b. This gives a much more accurate feed proration for each animal than the initial proration determined according to FIG. 27. This new feed proration will be used to calculate each animal's feed intake for the next feeding period. Of course, for the indicated calculations, both the rate of weight gain (ADG) and the total amount of change (gain) and the fat (fat deposition rate) and external dimensions (frame, muscular growth) are used in calculating the new projected DTF and OEW for each animal.

At the same time, each animal's DTF as calculated is checked against any drug withdrawal and safe-to-ship information available from the health history of the animal, also stored in the computer system according to the system described in the aforementioned U.S. Pat. No. 5,315,505. Any OED or DTF calculated by the computer or otherwise would be adjusted as dictated by the drug withdrawal and safe-to-ship information from the animal health system and prior to any assignment of the animal to any particular sort group. This drug withdrawal and safe-to-ship check might be done either by computer or manually by the operator. Also before any growth promotant drug or implant is administered to the animal in the processing station, a decision would be made on whether to administer at all based on the calculated DTF or OED, drug cost, and efficacy. In short, no growth promotant drug need be given if the animal is predicted to remain in the feedlot for only a short time following a remeasurement.

As each animal leaves the single-file chute, the computer has determined its sort group and allocated a particular sort pen in which to direct it from the chute. Steps 6 and 7 of the diagram of FIG. 7 represent a sorting procedure that may be used following a remeasurement. Essentially, each animal is directed to one of the seven sort pens of FIG. 5 temporarily. Each of the seven sort pens indicated in step 6 will receive animals selected according to seven different sort groups. The sort group to which a particular animal is assigned may be based on any one or more of several parameters but most likely will be based on their OED or DTF, their visual scores, their weights, their physical condition, or a combination thereof.

In the illustration of FIG. 7 there are seven sort groups. These are designated, "sort group 1", "sort group 2", "flex group", "earlies", "lates", "reruns", and "trash". Before the sorting procedure is over in step 6, these seven sort groups will be reduced to four, consisting of "sort group 1", "sort group 2", "earlies", and "lates". Each of those four groups will then be directed, in turn, according to step 8, into one of the four feed pens A, B, C or D according to their sort groups. Feed pens A-D in all likelihood will be the same feed pens as used in step 4.

To explain the sort groups further, "reruns" are cattle for which one or more measurements are missing or a process was omitted after a first pass through the single-file chute. As a result, cattle sorted into sort pen 1 as reruns will be run again through the single-file chute and there sorted into one of the other six groups, as indicated in step 7.

The "earlies" group consists of cattle that are predicted to have earlier OED's or DTF's than the rest of the cattle being sorted. In other words, they are predicted to have shipping dates to the packing plant considerably earlier than the cattle in the other groups. As indicated, cattle in the earlies group will be directed from sort pen 2 in step 6 to feed pen A in step 8. It should be noted that some of the reruns from sort pen 1, after being rerun, may end up in the earlies group of sort pen 2 and be eventually directed into feed pen A.

Sort pen 6, consisting of the "lates" group, include cattle that are predicted to have late shipping dates (DTF's or OED's), as compared to the other groups. As indicated in the diagram of FIG. 7, the lates group will be directed from sort pen 6 to feed pen D. The lates group may eventually include some of the reruns of sort pen 1 after the reruns are passed again through the single-file chute.

The "trash" group is composed of non-performing or poorly performing cattle and are sorted into sort pen 7. These are cattle that have poor ADG's or other physical problems that render them unsuitable for beef production or that are unprofitable to keep in the feedlot. Cattle in the trash group are culled from the rest of the animals, removed from the feedlot and sold as salvage.

The three remaining groups are sort group 1, sort group 2 and the flex group. Whatever the parameters being used to sort, the flex group consists of animals that are close to the dividing line between sort group 1 and sort group 2. For example if sorting is by weight and sort group 1 consists of a range of lighter weight animals and sort group 2 a range of heavier weight animals, the flex group consists of animals that are somewhere in a weight range between the two principal sort groups.

For example, after a first pass through the single-file chute, sort group 1 might include 20 animals and sort group 2 might include 17 animals. The purpose of the flex group is to even out the number of animals in each of sort groups 1 and 2. In the given example, if there are 10 animals in the flex group, they would be resorted by sending them through the single-file chute again and redistributing them into either sort group 1 or sort group 2 according to weight. As a result of this resorting process with respect to the flex group, eventually there are no remaining animals in the flex group, as they have all been redistributed to either sort group 1 or sort group 2. In the given example, where sort group 1 originally includes 20 animals, sort group 2 17 animals and the flex group 10 animals, eventually sort group 1 may end up with 24 animals, sort group 2 with 23 animals and the flex group with none. When the flex group has been redistributed, the animals in sort groups 1 and 2 are directed respectively to feed pens B and C.

A further explanation and example of flex sorting follows.

Flex Sorting Description and Examples

Flex sorting is a method of sorting a group of random animals into sort groups of predetermined size and quantity. The particular measurement that is used for ordering is of minor importance to the flex sorting method, but some examples are current weight, finish date, and finish weight. To achieve this sort, an ordered list of animals is maintained as the data is collected, a sort group is assigned based on the position within the ordered list. As the sorting starts, insufficient data will exist to make reasonable sort decisions, so animals are placed in a flex group until enough data has been collected to be representative of the whole population. This sample size is expressed as a percent of the total population, and is configurable. Other animals that will also be placed in the flex group are ones that are too close to the split between sort groups to be certain to which group they belong. This area of uncertainty is defined by flex percent value, it is also configurable and is expressed as a percent of the data range (i.e. maximum value–minimum value). At the completion of sorting, the animals in the flex group are processed again, this time since all information is known about the population the correct sort decision can be made.

EXAMPLE

| Setup parameters: | |
| --- | --- |
| total population | 5 head |
| sort distribution | 2 groups |
| first group | 2 head (40% of total) |
| second group | 3 head (60% of total) |
| sample size | 30% |
| flex percent | 10% |

Sample weight data 625, 600, 675, 610, 640

1. First weight is 625, add to ordered list, compute new median, and the area of uncertainty.

| RESULTS: | | | |
| --- | --- | --- | --- |
| Ordered List | Median Loc | Median Wt | Uncertainty |
| 625 | 1st element | 625 | N/A |

Since the number of weights (1) is less than sample size (1.5=*0.3) put this weight in flex group.

| RESULTS: | | |
|---|---|---|
| Sort Group 1 | Sort Group 2 | Flex Group |
| | | 625 |

2. Next weight is 600, add this weight to the ordered list, compute new median, and the area of uncertainty.

| RESULTS: | | | |
|---|---|---|---|
| Ordered List | Median Loc | Median Wt | Uncertainty |
| 600 | ((2 − 1) * 0.4) + 1 | AVG.(1&2) | (625 − 600) * 0.1 + |
| 625 | or between 1&2 | or 612.5 | or −2.5 |

Since the number of weights (2) is greater than the sample size (1.5), check to see if new weight is in the area of uncertainty. The area of uncertainty is 610 to 615, the new weight is not in this area and is less than the median, so it belongs in sort group one.

| RESULTS: | | |
|---|---|---|
| Sort Group 1 | Sort Group 2 | Flex Group |
| 600 | | 625 |

3. Next weight is 675, add this weight to the ordered list, compute new median, and the area of uncertainty.

| RESULTS: | | | |
|---|---|---|---|
| Ordered List | Median Loc | Median Wt | Uncertainty |
| 600 | ((3 − 1) * 0.4) + 1 | AVG (1&2) | (675 − 600) * 0.1 + or |
| 625 | or between 1&2 | or 612.5 | −7.5 |

Since the number of weights (3) is greater than the sample size (1.5), check to see if new weight is in the area of uncertainty. The area of uncertainty is 605 to 620, the new weight is not in this area and is greater than the median, so it belongs in sort group two.

| RESULTS: | | |
|---|---|---|
| Sort Group 1 | Sort Group 2 | Flex Group |
| 600 | 675 | 625 |

4. Next weight is 610, add this weight to the ordered list, compute list, compute new median, and the area of uncertainty.

| RESULTS: | | | |
|---|---|---|---|
| Ordered List | Median Loc | Median Wt | Uncertainty |
| 600 | ((4 − 1) * 0.4) + 1 | AVG (2&3) | (675 − 600) * 0.1 + or |
| 610 | or between 2&3 | or 617.5 | −7.5 |
| 625 | | | |
| 675 | | | |

Since the number of weights (4) is greater than the sample size (1.5), check to see if new weight is in the area of uncertainty. The area of uncertainty is 610 to 625, the new weight is in this area and must be placed in the flex group.

| RESULTS: | | |
|---|---|---|
| Sort Group 1 | Sort Group 2 | Flex Group |
| 600 | 675 | 625 |
| | | 610 |

5. The last weight is 640, add this weight to the ordered list, compute new median, and the area of uncertainty.

| RESULTS: | | | |
|---|---|---|---|
| Ordered List | Median Loc | Median Wt | Uncertainty |
| 600 | ((5 − 1) * 0.4) + 1 | AVG (2&3) | (675 − 600) * 0.1 + or |
| 610 | or between 2&3 | or 617.5 | −7.5 |
| 625 | | | |
| 640 | | | |
| 675 | | | |

Since the number of weights (5) is greater than the sample size (1.5), check to see if new weight is in the area of uncertainty. This area of uncertainty is 610 to 625, the new weight is not in this area and is greater than the median, so it belongs in sort group two.

| RESULTS: | | |
|---|---|---|
| Sort Group 1 | Sort Group 2 | Flex Group |
| 600 | 675 | 625 |
| | 640 | 610 |

6. Now it is time to do the flex pen, the first weight of 625 is already in the ordered list so we only need to determine which group it belongs in.

| RESULTS: | | | |
|---|---|---|---|
| Ordered List | Median Loc | Median Wt | Uncertainty |
| 600 | ((5 − 1) * 0.4) + 1 | AVG (2&3) | None |
| 610 | or between 2&3 | or 617.5 | |
| 625 | | | |
| 640 | | | |
| 675 | | | |

Since there is no area of uncertainty and the current weight is greater than the median, it belongs in group two.

RESULTS:

| Sort Group 1 | Sort Group 2 | Flex Group |
|---|---|---|
| 600 | 675 | 610 |
|  | 640 |  |
|  | 625 |  |

7. Now the last flex weight of 610 is already in the ordered list so we only need to determine which group it belongs to.

RESULTS:

| Ordered List | Median Loc | Median Wt | Uncertainty |
|---|---|---|---|
| 600 | ((5 − 1) * 0.4) + 1 | AVG (2&3) | None |
| 610 | or between 2&3 | or 617.5 |  |
| 625 |  |  |  |
| 640 |  |  |  |
| 675 |  |  |  |

Since there is no area of uncertainty and the current weight is less than the median, it belongs in group one.

RESULTS:

| Sort Group 1 | Sort Group 2 | Flex Group |
|---|---|---|
| 600 | 675 |  |
| 610 | 640 |  |
|  | 625 |  |

The above example demonstrates a two-way sort, but it can sort any number of ways. For an n-way sort there are (n−1) median locations within the ordered list to keep track of, but only one flex pen is needed to hold the animals that we are uncertain about. Also, in the example given, the sort was done without any errors or animals in the wrong pen. It is possible for the sort to end up with a different head count in the sort group than expected, or for some head to be in the wrong pen based on their sorting measurement. These mistakes occur mostly at the splits between two sort groups, and involve animals with very close measurements. One thing that should be pointed out is that this sorting method, like a lot of other sorting methods, performs better if the data is random. The worst possible scenario is for the data to already be sorted either ascending or descending.

One additional feature of this sorting method is the ability to have a human make subjective sort decisions, such as color, before running through the flex sort, in effect having two flex sort sessions running concurrently.

With the animals in feed pens A, B, C and D for the second portion of the feeding period as indicated in step 8, they may remain in their respective pens until they are ready for shipment. During this second feeding period of typically 60-80 days, selected animals or selected groups of animals may again be remeasured and resorted through the single-file chute and sorting pens if desired or economically feasible. For example the timeline of FIG. 3 indicates two remeasurements and resorts during the feeding period. However FIG. 7 illustrates a single remeasuring and single uniformity sort more like the procedure outlined in FIG. 4A.

All of the animals in feed pens A–D have new and more accurate pro rata feed intake ratios assigned to them using the method outlined in FIG. 28a and FIG. 28b, including data such as ADG, gain, external and internal measurements and other factors. Individual animal records are maintained for each animal during its remaining period of time in the feedlot. Additional weight checks or other measurements may be used to monitor actual performance during this second portion of the feeding period to confirm or modify the OED or DTF of each animal.

Also, as indicated in FIG. 4C, after a certain period within feed pens A-D, one or more of the groups may be sent to pen sorters such as pen sorter 94 in FIG. 2 for finish feeding for the time that these groups will be within their marketing window. This approach allows for "fine-tuning" of the optimum date of shipment for each individual animal based on market conditions and the individual animal's performance in its final days at the feedlot. This selection process, whether accomplished visually, by weight checks or by final feeding in a pen sorter, involves the selection process as indicated in step 8A for shipment of the animal to the packing plant. In the case of a pen sorter, this would involve sorting the animal selected for shipment from the feeding pen portion of the sorter to the shipping pen portion, as previously described.

Animals may be selected for shipment based on a selected marketing group of animals having the same average OED's or DTF's or on an individual animal basis, depending on how finely tuned the selection process desired. The selection process may be performed visually, by computer or by repeated weight checks as previously described.

Step 9 of the management system involves shipping the selected animals to the packing plant 156. At the packing plant, the animals are slaughtered for production of beef products for consumption. At the packing plant, the EID tag on each live animal is read and transferred by computer to match the identification on the resulting carcass so that the carcass data can be matched to the live animal performance and history data.

At the packing plant, the EID tags are removed from the animals and shipped in a container to a reconditioning operation where they are cleaned, tested and sorted for delivery back to the proper feedlot. The carcass data and the disbursements of funds breakdown for the original owners of the animals in a marketing group are transmitted to the appropriate feedlot. This data may also be transmitted to the original cattle producers for use in improving the genetics of the animals for future beef production.

The feed proration flow charts of FIGS. 27, 28a and 28b have been discussed. Following each table is an example calculation using the formulas and flow diagrams set forth in the figures. These examples set forth the data output from the computer when provided with software for carrying out the calculations set forth in FIGS. 27, 28a and 28b. The examples are for four animals identified as animals nos. 85, 10, 68 and 36. From the examples it will be seen that animal No. 85 had a starting weight of 829 pounds and a calculated optimum finish weight of 1136 pounds. During the initial feeding period P1 the ratio of feed allocated to it was 0.255646, so that out of a total of 780 pounds of feed fed during the first feeding period, 199.4038866 pounds of feed was prorated to it for allocating feed charges. During the next current period CP, the same ratio was used to prorate a total of 3,000 pounds of feed among the four animals, with 767 pounds being allocated to animal No. 85. However from the subsequent calculation, the DMI ratio for animal 85, based on remeasurements and original measurements, changed to 0.253206. As a result, animal 85 in the next feeding period ended up with 1,519 pounds of feed prorated to it out of a total of 6,000 pounds. It will also be noted from the calculations and data output from the computer that animal No. 85, when remeasured, had a weight of 1,028 pounds, up from an 829 pound initial weight. It also ended up with an actual weight of 1,128 pounds at final measurement compared to an original calculated optimum finish weight of 1,136 pounds.

When the four animals finally left the feedlot, their DMI numbers overall were recalculated to adjust their overall DMI ratios, resulting in a reallocation of the total feed fed to each animal. Animal No. 85 had 2,440 pounds of feed allocated to it out of a total of 9,660 pounds, based on its recalculated overall feed ratio of 0.25262. The final data output from the feed proration calculations is a ratio of feed to weight gain for each animal. Animal No. 85 ended up with a feed to weight gain ratio of 8.17, second highest in the group of four animals considered.

D. The Computer System

FIG. 8 is a general block diagram of the data inputs and data outputs to the host computer system 78. There are two categories of inputs, including the group input category 194 and the individual animal input represented by interface 196. The individual prior history of each animal is entered upon each animal's arrival at the feedlot, as indicated by the prior history input 198. Such prior history would include each animal's date of birth and its genetic background. Also entered at initial processing and on subsequent remeasurements would be each animal's weight, hip height, backfat and hide condition as indicated at input 200. These measurements are obtained at the single-file chute in the manner previously described. These individual inputs in turn are transmitted by cable or radio frequency means to the host computer 78 for storage and use in calculating the previously discussed formulas. Group information when transmitted to the computer would include prior history data such as average daily gain while in the pasture and the group condition score, visually estimated at the time of arrival at the feedlot. Other information would include the sex, age, breed and hide thickness breakdown for the animals in the group. These "cattle factors" are also input into the computer through data entry means indicated at 204 and the group input interfaces 194.

Environmental factors such as air temperature, wind, and pen conditions where the animals came from are also collected and entered through data entry means 206 into the group input interface 194.

Management factors for each group including implants, ionophores and processing information, are collected and input through data entry means 208 into the computer through the group input interfaces 194. Finally, feed factors, such as ration composition, are input through data entry means 210 and the group input interfaces 194 into the host computer 78.

Market factors are also part of the data used to calculate the desired computer outputs, such factors including purchase price, cattle futures, basis and premium/discounts for the animals in the group. These market factors are entered through data entry means 12 and the group input interface 194 into the host computer 78.

With the data collected as described, and the appropriate software, the computer system is able to calculate, using formulas such as the ones disclosed in FIGS. 25, 26, 27, 28a, 28b, and Table 1, such outputs as a projected date to finish (DTF), optimum end weight (OEW), and projected end points such as finish weight, hot carcass weight, yield grade, and USDA quality grade. The computer system also calculates a return on investment including cost, incomes and profit as indicated at 218.

Examples of the type of data collected, calculated, stored and available in reports generated by the computer system are shown in Tables 3A☐3G.

Table 3A, the cattle received report by load, has already been discussed. It discloses the information available from the producer and entered into the computer through appropriate data entry means upon the arrival of a load of cattle at the feedlot. This is a "group" report and is the sort of information entered into the computer as indicated at data entry means 202, 204 and 206 of FIG. 8.

Table 3B is a pen assignment summary report, which is another group type report and gives the sorting pen assignments 1-7 for lot No. 495 of cattle that is to be fed in pens 59, 57 and 58. The number of head of cattle in each pen 10, 11 and 11 for sorting pens 1, 2 and 4 and feed pens 59, 57 and 58 is given. This information is available from the computer after at least one measurement and sort of a lot of animals.

Still referring to Table 3B, the remaining data in the pen assignment summary report should be self-explanatory, giving information concerning the projected finish weight, the current weight, the frame size and current backfat measurements, on average, for the animals in feed pens 59, 57 and 58. In addition to the averages for each of the indicated measurements, the pen assignment summary report also gives maximum and minimum ranges for the animals in each sort group.

Table 3C is a sample of a pen assignment detail report generated by the computer system. This report indicates the lot number, the feed pen number, the sort pen number, and the ED tag number of each of the 11 animals in feed pen 57. The report also indicates that the animals in this feed pen have a shipping window ranging from May 14, 1994 to Sep. 28, 1994, indicating that the animals in this group are expected to reach their optimum condition, such as optimum finish weight, sometime within this window. The pen assignment detail report also gives individual animal measurements and calculations including video image dimensions (VID), and projected days to finish (DTF) which is the number of days the animal is projected to require to reach its optimum finish weight. Also indicated is the projected optimum finish weight (OFW), the animal's current weight (CWT), and each animal's average daily gain (ADG). Finally, the pen assignment detail report gives each animal's frame measurement score (FM) and backfat measurement (BF).

Because of the amount of information available for each animal in each feed pen in the feedlot, and at any time during the animal's stay in the feedlot, it will be readily appreciated how animals can be selected, on an individual basis if desired, for shipment to the packing plant when each animal is in optimum condition for shipment. Simply by taking repeated measurements of each animal as it nears its projected shipping date or optimum finish weight, animals can be selected for shipment and slaughter based on their individual performances and market factors rather than the performances of any particular group, if desired.

Table 3D and Table 3E are marketing yard sheets that the computer system can generate for each animal in the feedlot. The marketing yard sheet of Table 3D is for the same group of animals as the marketing yard sheet of Table 3E. However the yard sheet of Table 3D gives individual animal data for lot No. 495 of animals on the measurement date of Mar. 30, 1994, while Table 3E gives the data for the same animals in lot No. 495 approximately three weeks later, on Apr. 22, 1994.

As will be seen by the columns in the marketing yard sheets, each animal is identified by tag number, pen number and lot number. Additional data available in the other columns of both marketing yard sheets include various projections that have been calculated for each animal, a comparison of purchase weight and current weight for each animal, days on feed (DOF) information for each animal, the ration information that applies to each animal, average daily gain (ADG) information for each animal and feed intake information for each animal. Finally, the projected and actual cost information based on various treatments, processing and other factors for each animal is listed.

Table 3F is a sample of a pen closeout report generated by the computer system as a result of the various inputs, including measurement inputs for each animal and each group of animals. This gives the income and expense information for a pen of animals, broken down to an average cost per head, including feed charges, cattle insurance, yardage fees and processing fees. Other pen information included in the pen closeout report includes such information as total pounds gained by all animals in the pen, broken down to an average gain per head. Also included are average daily gain for each animal, daily feed costs per head, daily total costs per head, total pounds of feed fed for the pen and total pounds per head. Also included is average daily consumption data. Other information includes the cost of the feed fed.

In the summary at the bottom of the pen closeout report, the profit or loss from the pen is given. In the sample, there was no profit for the indicated pen, which included 10 heifers. Based on the summary, the 10 heifers in the pen had an average incoming weight of 678 pounds and an average outgoing weight of 787 pounds. Each gained an average of 3.21 pounds per day for a total of 34 days on feed. The cost of the gain was $56.21.

The final sample report is shown in Table 3G which is a Closeout Summary By Lot report. In this case the lot number is 42894, which was included in pen 553, containing a total of 27 head. The total profit for the lot was $4,957.98. Each animal in the report is identified by its visual identification tag number (VID) and the profit from each animal is calculated. In addition, each animal's performance during its stay in the feedlot is calculated. Each animal is listed under its sire and dam. This sort of information is valuable to the cattle producer in determining which sires and dams produce the most profitable offspring. This information is then used in making future breeding decisions.

Figure 6:
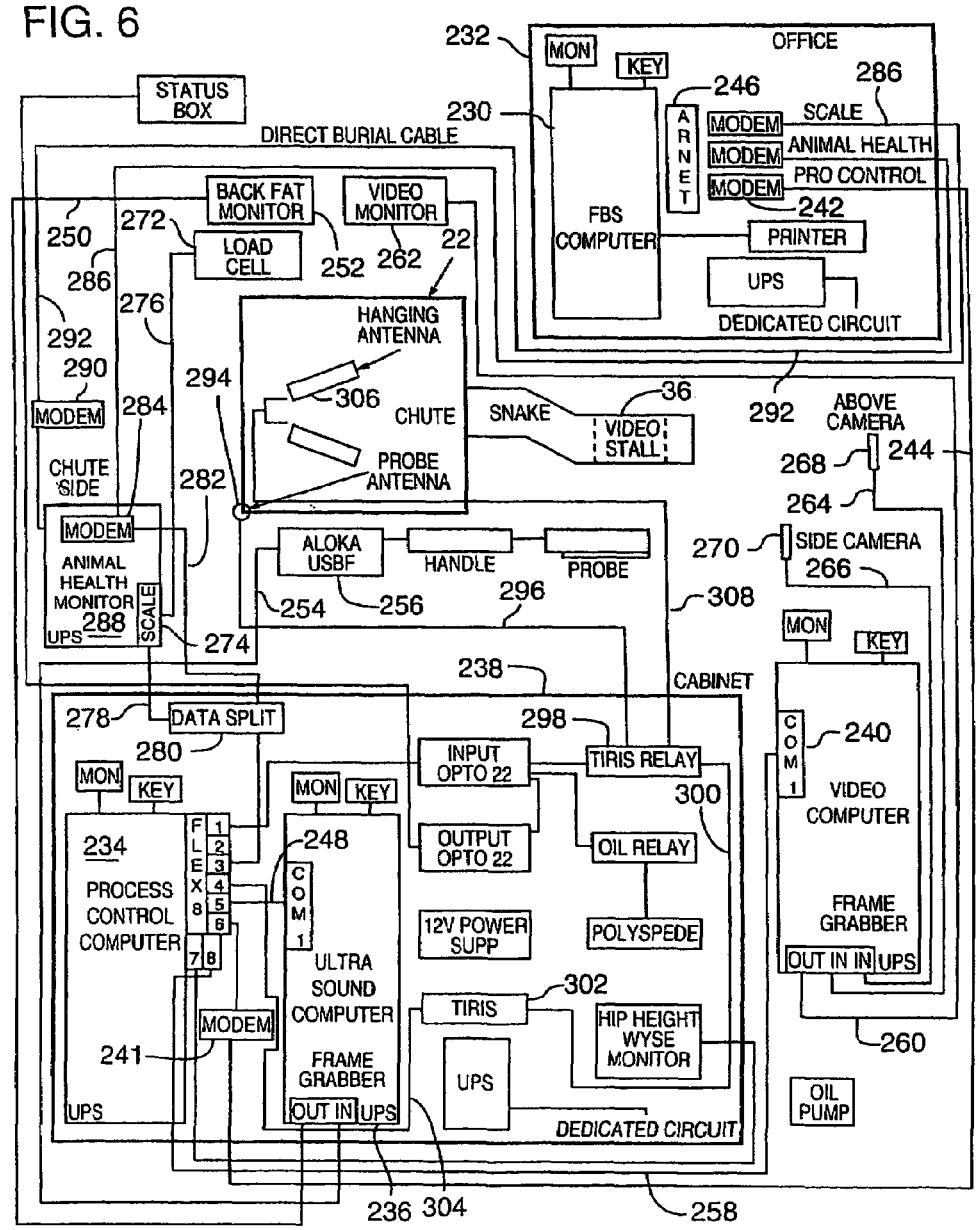
FIG. 6 is a block diagram of the computerized control system that may be used for carrying out the present invention.

A layout of the computer system used in a prototype of the present invention is shown in FIG. 6. Several different computers are used in the system. First there is a feedlot business systems (FBS) computer 230 located at the feedlot office 232. This computer stores the databases used in the system and performs most of the calculations needed in operating the system.

Remote from the FBS computer and closer to the chute area 22 are a separate process control computer 234 and an ultrasound computer 236 within a common control cabinet 238. Separate from the control cabinet and the other computers is a video computer 240.

Basically, the process control computer 234 controls the operation of all subsystems including the stall and sorting gates, weigh scale, ultrasound computer and the video computer. The process control computer communicates with the FBS computer through the modems 241, 242, line 244 and FBS interface 246. The ultrasound computer 236 communicates with the process control computer 234 through a line 248. The ultrasound computer 240 also has an output line 250 to a backfat monitor 252 and an input line 254 from the ultrasound backfat scanner 256 at the single-file chute stall 40.

The video computer 240 communicates with the process control computer 234 through a commline 258. It also has an output line 260 to a video monitor 262, and input lines 264, 266 to video cameras, including an overhead camera 268 and a side-view camera 270.

Each animal is weighed by a scale loadcell 272 at the weigh stall 38. The loadcell communicates with the scale 274 through a line 276. The scale in turn communicates with the process control computer through a line 278 and data split 280. Data from the data split also can be communicated via line 282 and a modem 284 and line 286 directly to the FBS computer 230 through the FBS interface 246.

Data concerning drugs, other animal health treatments and other information about an individual animal at the processing station or stall 42 can be entered into an animal health computer or monitor 288 at the processing station and from there communicated directly through the modem 290 and line 292 and interface 246 to the FBS computer.

As previously noted, each animal has an EID tag applied to it in the single-file chute to give each animal a unique electronic identification. This identification is transmitted from the EID tag by a probe antenna 294 at the EID/USBF stall 40 through a line 296 from the chute to a tiris relay 298 and from the relay through a line 300 to a tiris EID reader 302. The tiris reader 302 transmits the animal's EID identification through a line 304 to the process control computer 234. Alternatively, each animal's EID tag signal can be received by a hanging antenna 306 at the single-file chute and transmitted via line 308 to the tiris relay 298 and thence through line 300 to the tiris reader 302 and through the line 304 to the process control computer 234.

The FBS computer not only collects data and uses it to calculate projections, costs and other information used in the management method and system, it also collects data from other sources not shown. For example, the FBS computer performs the regular feedlot accounting functions and generates financial reports. It may also receive and store data from a computerized animal drug inventory control and animal health history and drug treatment system as disclosed in the previously mentioned U.S. Pat. No. 5,315,505. The FBS computer may also collect and store data from a computerized feed additive delivery system such as disclosed in U.S. Pat. No. 4,733,971 and the related patents previously mentioned. The FBS computer may also receive and store data concerning the amount of feed ration delivered to each of the feed pens in a feedlot, including such data collected from a computerized bunk reader system such as disclosed in U.S. Pat. No. 5,008,821. All such information, including the drug usage information, feed ration usage information, and feed additive usage information can be used together with the data concerning each animal collected from the system of the present invention and other data that may be collected and stored in the FBS computer database to prorate feed ration and feed additive costs to individual animals and thereby calculate the cost of production value and other pertinent information about each animal in the feedlot according to various formulas, a few of which are disclosed as examples and discussed.

Tables 4A–4E are sample pages of prompts that are generated by the computer programs that are used in the computer system 78 that operates the described system. The described management system is known as the electronic cattle management system (ECM) which is the computer symbol used to initiate the program. The ECM program includes four session types, one of which is entered to begin the system's operation. In Table 4B it will be seen that certain animal measurements can be keyed in, automatically entered or not recorded.

Item 7 in Table 4B gives the prompts for entering the type of sorting that is desired such as, for example, a flex sort as previously described.

At the top of Table 4C, the prompts for entering the number of animals to be sorted into the various sort pens are indicated.

Table 4D lists the various prompts for processing each animal at the single-file chute. By entering the proper prompt, the computer can be instructed to process the identified animal in a particular way such as by weight, by reading its EID, by ultrasound measurement of backfat and/or by taking external video measurements.

Additional prompts for setting the parameters for measuring and sorting are given in Table 4E and 4F.

E. Computer Programs The method and system of the present invention use a number of different computer programs to run the system as described, the operation and sequencing of which are all controlled by the previously described process control computer 234 shown in FIG. 6. These programs will now be described with reference to their respective flow charts.

First, control of the operation of the entrance and exit gates at the various stalls or stations in the single file chute will be described. First with reference to FIG. 9A, the get-ready station 34 in the single-file chute includes the entrance or tail gate 46 and the exit or head gate 48 defining the stall. Within the stall are three sensors including a tail sensor 342, a fill sensor 344 and a head sensor 346. These sensors, which may be photoelectric sensors or some other automatic sensors, detect the presence of an animal within the stall space, and when all three sensors detect the presence of an animal, the animal will be contained within the space, whereupon the tail gate 46 can be closed after being opened initially to allow entrance of the animal into the stall space. FIG. 9A also indicates the direction of travel of the animal through the single-file chute and the stall space as indicated by the arrow 316.

Referring now to FIG. 9B, the computer program for controlling the operation of the tail and head gates 46, 48 is disclosed. This computer program resides in the process control computer 234 of FIG. 6. Although not shown, obviously the sensors associated with the get ready stall and all other stations in the single-file chute and the sort pens, to be described, are in communication with the process control computer.

First the program is conditioned by another program to be described to get ready to receive the next animal that will proceed through the single file chute, as indicated at step 318. At this point, if the fill sensor is off as indicated at 320, the program assumes that the get ready stall is empty and so commands that the head gate be closed as indicated at step 322. Then the program commands opening of the tail gate 324 to allow the next animal to enter the get ready stall. After the tail gate opens, the program waits until the fill sensor at 326 detects the presence of an animal in the stall. The program then proceeds to the next step to detect when the tail sensor is turned off, at step 328. When this occurs, the program commands closing of the tail gate at step 330. If at step 326 the fill sensor does not detect the presence of an animal, the tail gate will not close. Also, as indicated at 328, if the tail sensor remains on, the tail gate will not close. Only when the fill sensor is on and the tail sensor is off can the tail gate close.

After the tail gate closes, the program inquires at step 322 whether the next station, namely the video station 86, is ready for the next animal. At this point nothing happens until the processing computer receives an indication that the video station is ready for the next animal. When this occurs, the program, as step 334, signals the video computer 240 to get ready for the next animal. At this point the head gate 48 is opened as indicated at 336. The program then inquires at step 338 as to whether the fill sensor 312 in the get ready stall is off and at step 340 whether the head sensor is off. When both the fill sensor 312 and the head sensor 314 are off, indicating that an animal has left the get ready stall and entered the video stall, the program commands the head gate 48 to reclose as indicated at step 322, and then commands the tail gate at step 324 to reopen to ready the stall for the next animal.

Figure 10A:
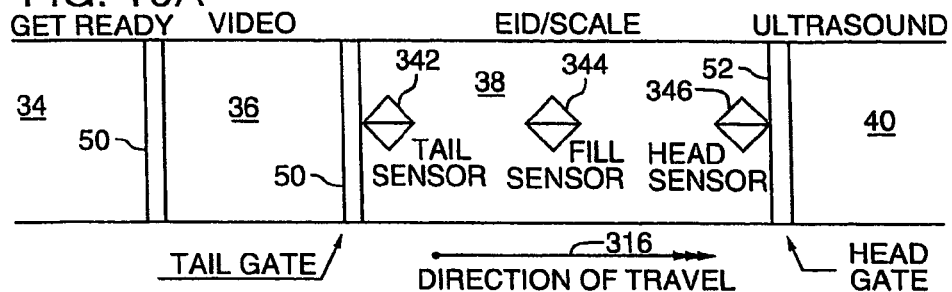
FIG. 10A is an enlarged schematic diagram of the video and EID/scale stations of the single-file chute shown in FIGS. 1 and 5, showing the locations of sensors used in operating the tail and head gates for the EID/scale station.

Referring to FIG. 10A, after the animal leaves the get ready stall 34 it walks through the video stall 36 where it is scanned for external dimensions, and proceeds, without stopping, through the open tail gate 50 directly into the EID/scale stall 38 where the animal is weighed and an EID tag is applied to the animal if necessary and read to identify it. Because of the continuous movement of the animal through the video stall, there are no tail, fill or head sensors in that stall. However the subsequent EID/scale stall requires the animal to stop while it is weighed. Thus, both the tail gate 50 and the head gate 52 must be closed while the animal is contained within the EID/scale stall, identified and weighed. Thus such stall includes a tail sensor 342, a fill sensor 344 and a head sensor 346, all of which communicate with the process control computer. Again, the direction of travel of the animal is indicated by the arrow 316.

Figure 10B:
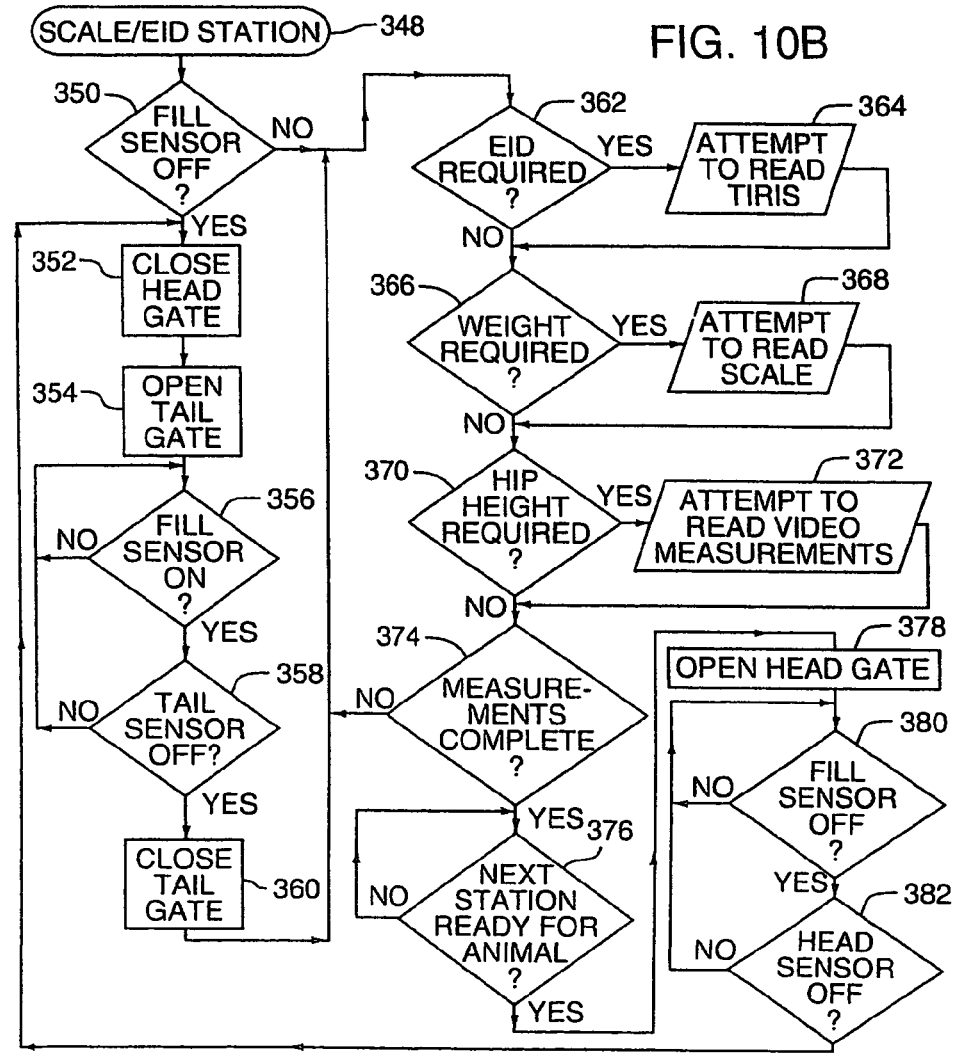
FIG. 10B is a flow diagram of the computer program used to control the operations of the tail and head gates for the EID/scale station of FIG. 10A in conjunction with the sensors of such station.
Figure 11A:
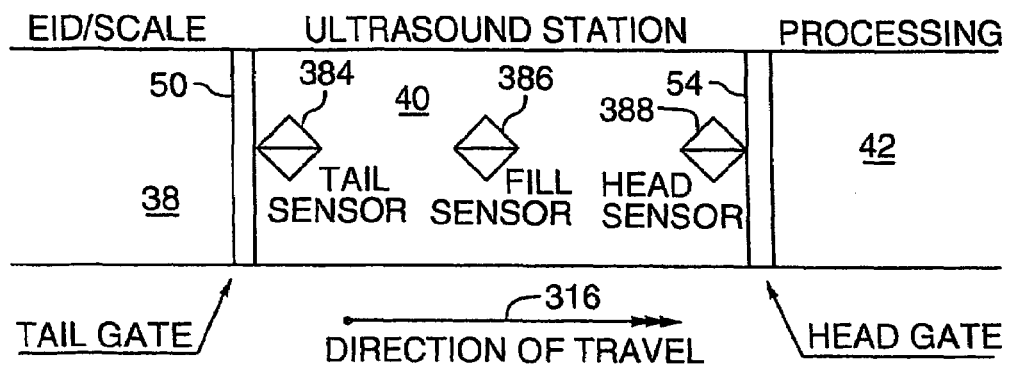
FIG. 11A is an enlarged schematic diagram of the ultrasound station portion of the single-file chute shown in FIGS. 1 and 5 showing the locations of sensors used in operating the control gates for such station.

Referring to FIG. 10B, the computer program for operating the tail gate 50 and head gate 52 at the EID/scale station is disclosed. As an animal proceeds through the video stall 36, tail gate 50 will be open if the EID/scale station is ready for the next animal, which will be determined by whether or not the head gate of such station is closed and its fill sensor and head sensors 344, 346 are off. At this point, the EID/scale station computer program 348 is initialized and ready to start its sequence of operation. First, at step 350, the program inquires whether the fill sensor 344 is off. If so, it commands the head gate 52 to close at step 352. Thereafter, at step 354 the tail gate 50 is commanded to open, allowing the next animal to enter the EID/scale stall. Next the program, at step 356, inquires whether the fill sensor is on. If so, it inquires at step 358 whether the tail sensor is off. If so, at step 360, the program commands the tail gate 50 to reclose, whereupon the animal is ready to be weighed and have its ED tag attached if necessary, and read.

With the animal in the ED/scale stall, the program inquires at step 362 whether an EID identification of the animal is required. If so, the process control computer 234 is commanded to attempt to read the tiris EID reader 302 at step 364. If no EID is required, the program next inquires whether a weight is required at step 366. If so, the process control computer at step 368 is commanded to read the animal's weight from the scale 274. After this, or if no weight is required, the program will inquire at step 370 whether a hip-height measurement of the animal is required. If so, the process control computer is commanded at step 372 to read and record the video measurements communicated from the video computer 240. After the measurements are recorded, if required, the program inquires at step 374 whether measurements are complete. If not, the program will return to step 362 and again proceed through the program to attempt to read the video measurements. Once the measurements have been recorded, the program proceeds at step 376 to inquire whether the next station, namely the ultrasound station 40, is ready for the next animal. Unless the next station is ready for the animal, the head gate 52 will not open. When the next station signals that it is ready, through the process control computer, the head gate 52 is commanded to open at step 378. Next, the program inquires whether the fill sensor 344 is off, at step 380. If not, the program will not proceed to the next step and reclose the head gate. When the fill sensor is off, the program inquires whether the head sensor is off. If the head sensor is off, indicating that the animal has left the EID/scale stall, the program commands the process control computer to reclose the head gate 52. At this point the weighed and identified animal will have entered the ultrasound stall 40, and the program returns to step 352 to command reclosing the head gate in preparation for the next animal.

Referring to FIG. 9A, the ultrasound station 40 is disclosed as having a tail sensor 384, a fill sensor 386 and a head sensor 388. It also includes the tail gate 52, which is the same gate 52 that serves as the head gate for the preceding EID/scale stall 38. It also includes the head gate 54 which serves as the tail gate for the next processing stall 42. Again, the direction of travel of the animal through the ultrasound station and through the single-file chute is indicated by the arrow 316.

Figure 11B:
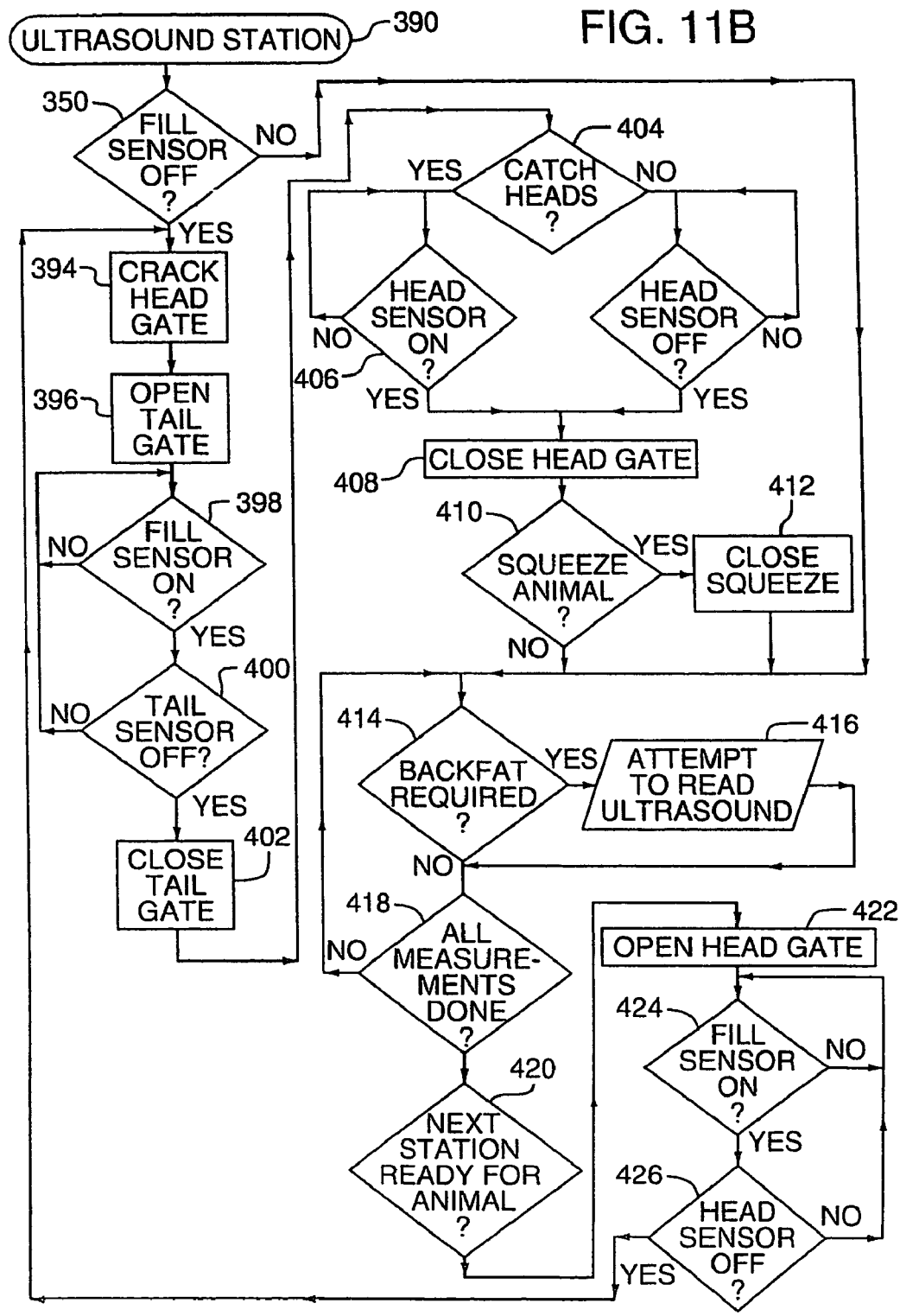
FIG. 11B is a flow diagram of a computer program used to control the operation of the tail gate and head gate of the ultrasound station of FIG. 11A in conjunction with the sensors for such station.

Referring now to FIG. 11B, the computer program for controlling the operation of the gates and thus the animal within the ultrasound station is indicated at 390. Once initiated, it first inquires at step 392 whether the fill sensor 386 is off. If not, because the preceding animal has not yet left the station, the program will return to determine whether the animal has not yet completed its ultrasound scan. However, assuming that the preceding animal has left the ultrasound station and the head gate 54 is closed, the program commands at step 394 that the head gate be cracked open. Then at step 396 the program commands the processing computer to open the tail gate. When the tail gate is opened, the program inquires whether the fill sensor is on, at step 398. If so, indicating that the next animal has entered the ultrasound station, the program inquires whether the tail sensor is off, at step 400. When the tail sensor goes off, the computer program instructs the computer to close the tail gate, at step 402, whereupon the next animal is fully within the ultrasound station and ready to be prepared for measurement. Once the tail gate is closed, the program inquires at step 404 whether the head catcher is to be employed to stabilize the animal in the station. If it is, the program inquires whether the head sensor is on at step 406. If it is, the program, at step 408, commands closing of the head gate.

Once the head gate is closed, the program at step 410 inquires whether the animal is to be "squeezed" within the station. This has reference to the device at the station commonly referred to as a "squeeze gate", which in effect squeezes the animal from behind into tight confinement within the stall so that it cannot move to any appreciable extent. If the answer is yes, the squeeze gate at 412 is commanded to close at step 412. If the answer is no, the squeeze gate is not actuated. In either case, the next programming sequence is an inquiry as to whether the animal's backfat is to be measured, at step 414. If the answer is yes, the program will attempt to take a reading from the ultrasound computer at step 416 to record the backfat measurement. If the answer is no, the program inquires whether all measurements are completed at step 418. This is also the next step after a backfat ultrasound reading is attempted at step 416. If the answer is no, the program will again attempt to take a backfat measurement. If the answer is yes, the program inquires whether the next station in the chute is ready for the animal, at step 420. If not, nothing further happens until the next station is ready for the animal. When that occurs, the head gate 54 is commanded to open at step 422. When the head gate is open, the program inquires at step 426 whether the fill sensor is off. If not, nothing further happens until the fill sensor is off. When that occurs, the program inquires at step 426 whether the head sensor is off. If not, nothing further happens until the head sensor is off. When that occurs, the program returns to step 394 to cause the head gate to crack ready for the next animal.

Figure 12A:
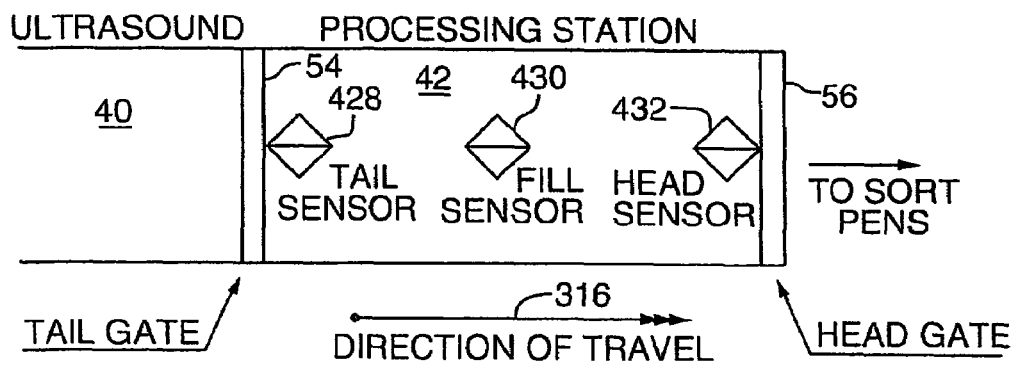
FIG. 12A is an enlarged schematic diagram of the processing station of the single-file chute of FIGS. 1 and 5 showing the location of sensors for operating the control gates of such station.

Referring to FIG. 12A, the animal proceeds from the ultrasound station 40 into the processing station 42 through the head gate 54 of the ultrasound station, which becomes the tail gate 54 of the processing station. Within the processing station are three sensors, a tail sensor 428, a fill sensor 430 and a head sensor 432.

Figure 12B:
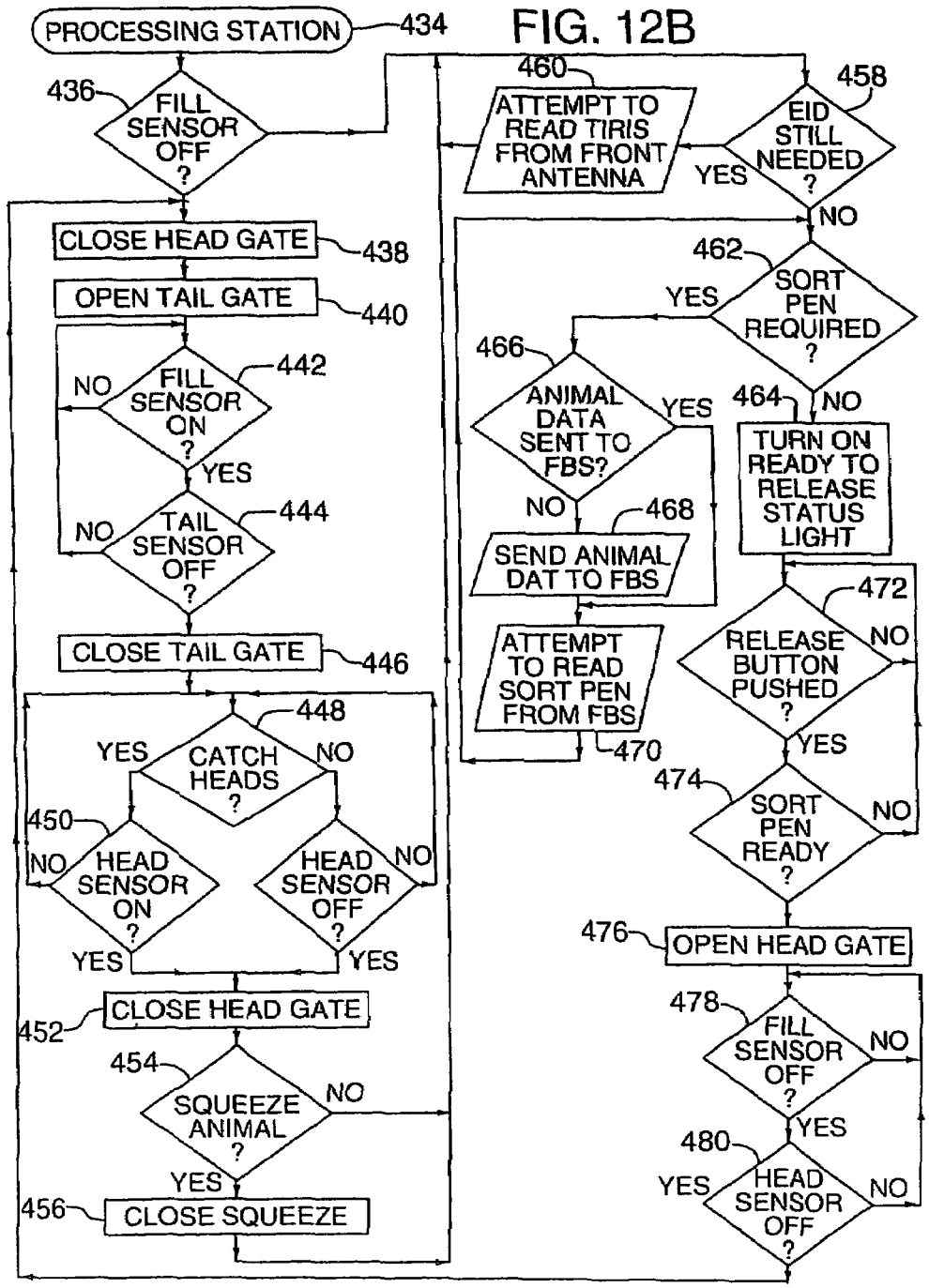
FIG. 12B is a flow diagram of a computer program used to control the operation of the tail gate and head gate for the processing station of FIG. 12A in conjunction with the sensors at such station.

Referring to FIG. 12B, the computer program for the processing station, indicated at 434, first inquires whether the fill sensor 430 is off, at step 436. If not, the head gate 56 will not close until the fill sensor does indicate that the preceding animal has left the processing station. When the fill sensor is off, head gate 56 is commanded to close at step 438 and the tail gate 54 is commanded to open at step 440 to admit the next animal into the processing station.

Next, the program inquires whether the fill sensor is on at step 442. If not, nothing further happens until the fill sensor is on. When that occurs, the program inquires whether the tail sensor 428 is off, at step 444. If the tail sensor is not off, the tail gate 54 will not close. When the tail sensor is off, indicating that the animal is completely within the processing station, the tail gate 54 is commanded to close at step 446. When the tail gate is closed the program, at step 448, inquires whether there is to be a head catch. If the answer is yes, the program inquires at step 450 whether the head sensor 432 is on. If not, nothing further happens until the head sensor is on. If the answer is yes, the head gate 56 is closed at 452 to catch the animal's head.

Next, the program inquires whether the animal is to be squeezed by the squeeze gate within the processing station, at step 454. If not, the program proceeds to the next processing sequence. If the answer is yes, the squeeze gate at the processing station is commanded to close at step 456 to confine the animal within the station. After the squeeze gate is closed, the program proceeds to the next processing sequence.

The next inquiry, at step 458, is whether the animal needs to be identified by its EID. If the answer is yes, the program instructs the process control computer at step 460 to attempt to read an identification from the tiris. Nothing further happens until the animal is identified. When the animal has been identified or if no identification is needed, the program inquires whether a sort pen for the animal is required, at step 462. If not, a status light on a control panel (not shown) at the processing station is commanded to indicate, at step 464, that the animal is ready to be released from the single-file chute.

If a sort pen is required, the program at step 466 inquires whether the animal data has been sent to the FBS computer. If the answer is no, the data is sent to the FBS computer, at step 468. If the animal data has already been sent to the FBS computer, the program bypasses step 468 and attempts to read the correct sort pen for the animal as determined by the FBS computer at step 470. The program then returns to the sort pen required inquiry step 462. If a sort pen is still required then the just described steps are repeated. If a sort pen identity is not required, then the program proceeds on through the sequence and the ready to release status light is illuminated on the aforementioned control panel.

Thereafter, an operator must manually press a release button to release an animal from the single-file chute into the alley between the sort pens. At this point the computer inquires whether the release button has been pushed, at step 472. If the answer is no, nothing further happens until the release button is pushed. When the release button has been pushed, the program inquires whether the sort pen is ready, at step 474. If not, nothing further happens until either the release button is pushed or the sort pen is ready. When the sort pen is ready, head gate 56 is commanded to open, at step 476. When the head gate is open, the program inquires whether the fill sensor is off, at step 478. If not, nothing further happens until the fill sensor is off. When it is off, the program next inquires whether the head sensor is off, at step 480. If not, nothing further happens until the head sensor is off. When it is off, the program returns to step 438 to close the head gate and prepare the stall for the next animal.

Figure 13A:
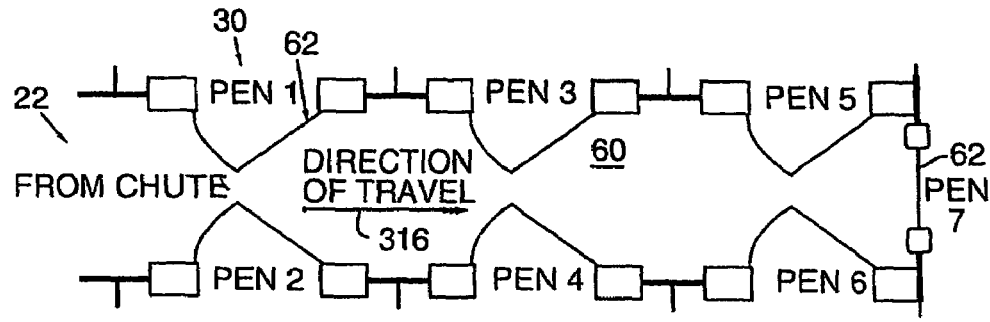
FIG. 13A is an enlarged schematic diagram of the sort pen entrance gates for the sort pens shown in FIG. 5.

Referring now to FIG. 13A, the seven sort pens 62 and their respective sorting pen entrance gates 62 are illustrated schematically. The direction of travel of the animals through the alley 60 between the two rows of sorting pens is indicated by the arrow 316 as they leave the single-file chute indicated generally at 22.

Figure 13B:
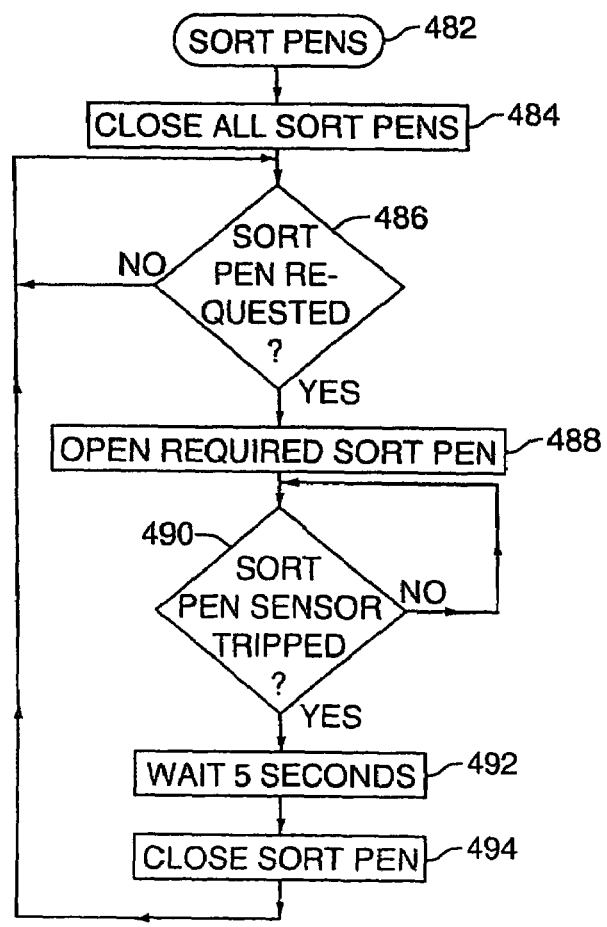
FIG. 13B is a flow diagram of a computer program used to control the operation of the entrance gates to the sort pens of FIG. 13A.

FIG. 13B is a flow diagram of the computer program 482 for operating the sort pen entrance gates 62. The first step in the programming sequence is to make sure all sort pen gates are closed at step 484. Next, the program at step 486 inquires of the process control computer whether a sort pen is requested. If not, nothing further happens and the sort pen gates remain closed, and each animal would travel through the alley 60 to an appropriate feed pen through the open gate 62 of feed pen 7 as indicated in FIG. 13A.

If a sort pen is requested, the designated sort pen is commanded to open at 488. When the sort pen gate is open the program inquires whether the sort pen gate sensor (not shown) has been tripped, at step 490. When the sort pen gate sensor is tripped, it would indicate that an animal has entered the sort pen through the open gate. The sort pen sensor, such as a photocell, would be located at the gate entrance so that its beam would be interrupted when an animal passes through the entrance into the pen with the gate open. After the sort pen sensor has been tripped, there is a five second delay, indicated at step 492, to give the animal time to pass through the open gate into the designated pen. Thereafter, the entrance gate is commanded to close again, as indicated at step 494. When the designated sort pen gate is closed, the program returns to step 486 to inquire if a sort pen is requested for the next animal. Nothing further happens until a sort pen is again requested.

Figure 14A:
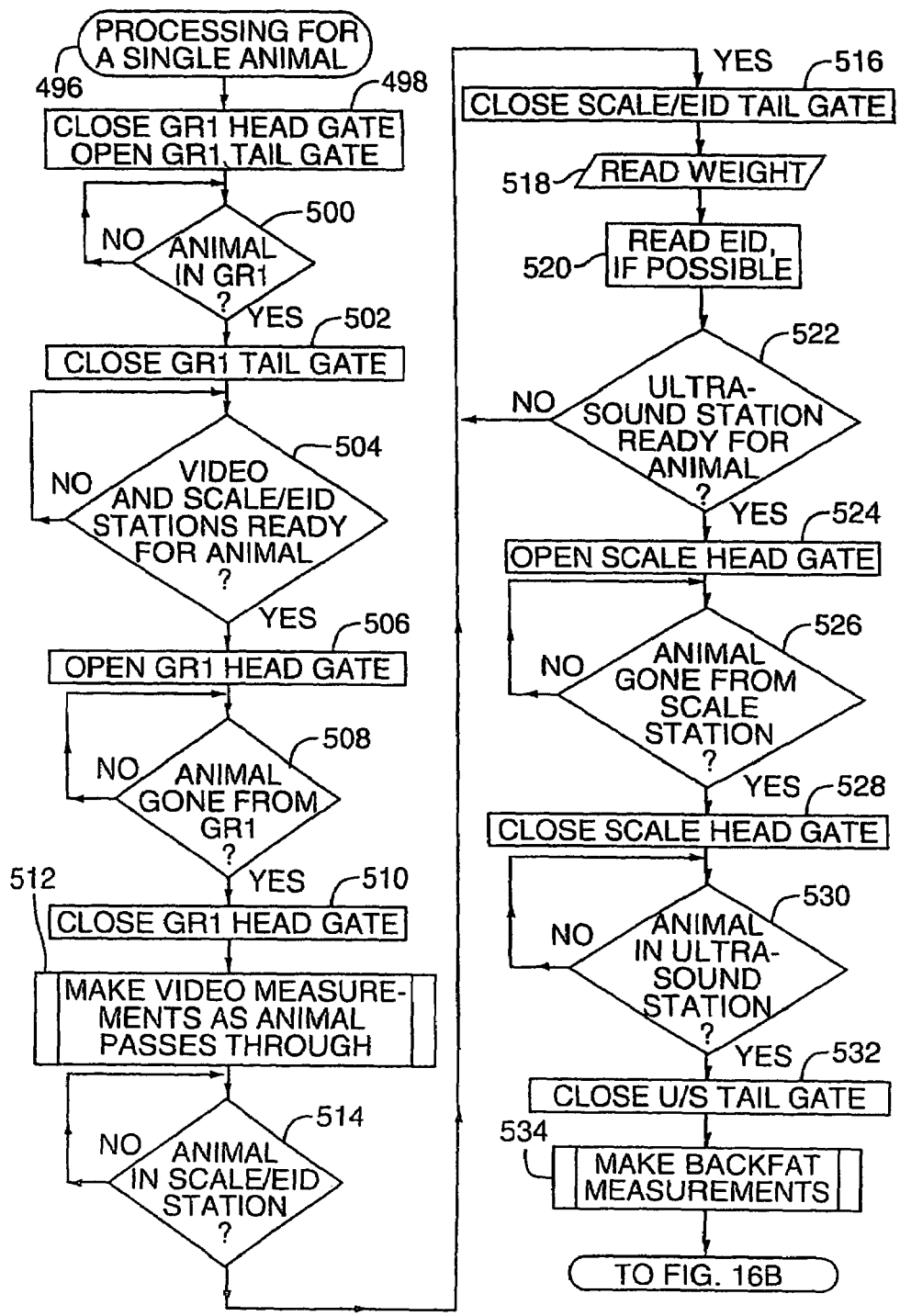
FIG. 14(AB) is a flow diagram of a computer program used to control the processing sequence for each animal proceeding through the various measuring and processing stations in the single-file chute of FIG. 5.

FIG. 14 is a flow diagram for the computer program in the process control computer that operates in conjunction with the measuring and processing station and sort pen operating programs to control the sequence of operation of the various station head and tail gates and sort pen entrance gates. The FIG. 14 program, indicated generally at 496, is for controlling the movement of a single animal through the single-file chute and its measuring and processing stations and into one of the selected sort pens. The processing sequence program 496 starts at step 498 by closing the GR1 stall head gate and opening the GR1 stall tail gate. Then at step 500 it asks whether there is an animal in the GR1 stall. If not, nothing further happens until an animal enters the GR1 stall.

When there is an animal in the stall as indicated by the fill and tail sensors in the stall, the GR1 tail gate is closed at step 502. Then the program asks if the video and scale/EID stations are ready for an animal, at step 504. If not, nothing further happens until those stalls are empty and ready for the next animal. When they are, the GR1 head gate opens at 506. Then, at step 508, when the sensors in the GR1 stall indicate that the stall is empty, the GR1 head gate closes at step 510. As the animal passes from the GR1 stall through the video stall the video measurements are made under control of the video computer, as indicated at step 512.

The animal passes from the video stall into the scale/EID station or stall as indicated at step 514. When the sensors in the scale/EID station indicate that an animal is in the station, the scale/EID tail gate is closed at step 516. Thereafter, the animal is weighed in the scale/EID station as indicated at 518. Next, there is an attempt to read the animal's EID identification at step 520. Thereafter, the program inquires whether the ultrasound station is ready for the animal at step 522. If not, nothing further happens until the ultrasound station is ready. When ready, the head gate of the scale/EID station is opened at step 524 so the animal can pass into the ultrasound station. Next, the program asks at step 526 whether the animal is gone from the scale/EID station. If not, nothing further happens until the program is told that the animal has left the station. When the animal is gone from the scale/ED station the scale/EID head gate is closed at step 528.

Next, the program asks at step 530 whether there is an animal in the ultrasound station. If not, nothing further happens until an animal is detected in the ultrasound station. Then the ultrasound tail gate is closed at step 532. Thereafter, the ultrasound computer operates the ultrasound machine to make the backfat measurements at step 534, and the process control computer is commanded to read the video measurements at step 536 by the processing station program.

Next, the processing station program asks whether the processing station is ready for the animal, at step 538. If not, nothing further happens until the processing station has cleared the previous animal and is ready for the next animal. Then, the ultrasound head gate is opened at step 540, allowing the animal to proceed into the processing station. Thereafter, the program asks whether the animal is gone from the ultrasound station, as indicated at step 542. If not, nothing further happens until the animal has cleared the ultrasound station. Thereafter, the ultrasound station head gate is closed at step 544.

Next, the program asks whether the animal has entered the processing station at step 544. If not, nothing further happens until the animal is fully within the processing station, after which the processing station tail gate is closed at step 546. After the animal is within the processing station, its EID identification is read at step 548, its measurement data from the previous measuring stations is transmitted to the FBS computer at step 550, and the FBS computer transmits to the process control computer the assigned sort pen for the animal at step 552.

At this point, within the processing station, the animal may be implanted with growth promotants or undergo additional treatment that may be indicated. When this processing is completed, a button is manually pushed by an operator to indicate that the animal is ready to leave the processing station. The computer program then asks whether the release button has been pushed at step 554 and if not, nothing further happens and the animal cannot leave the processing station. When the release button has been pushed, the program inquires whether the assigned sort pen is ready for the animal, at step 556. Until the designated sort pen is ready, nothing further happens and the animal remains in the processing station. When the sort pen is ready, the processing station head gate is opened at step 558 and the specified sort pen gate is also opened at step 560, so the animal can leave the processing station and proceed into the sort gate alley and into the open sort pen.

Next, the computer program asks whether the animal has left the processing station at step 562. If so, the head gate of the processing station is closed at step 564. Next, the program asks whether the sort pen sensor has been tripped by the animal entering through the sort pen gate, at step 566. If so, the designated sort pen gate is closed at step 568. Finally, the identification of the animal entering the sort pen is recorded at step 570 and the processing sequence program ends for that particular animal at step 572.

Figure 15:
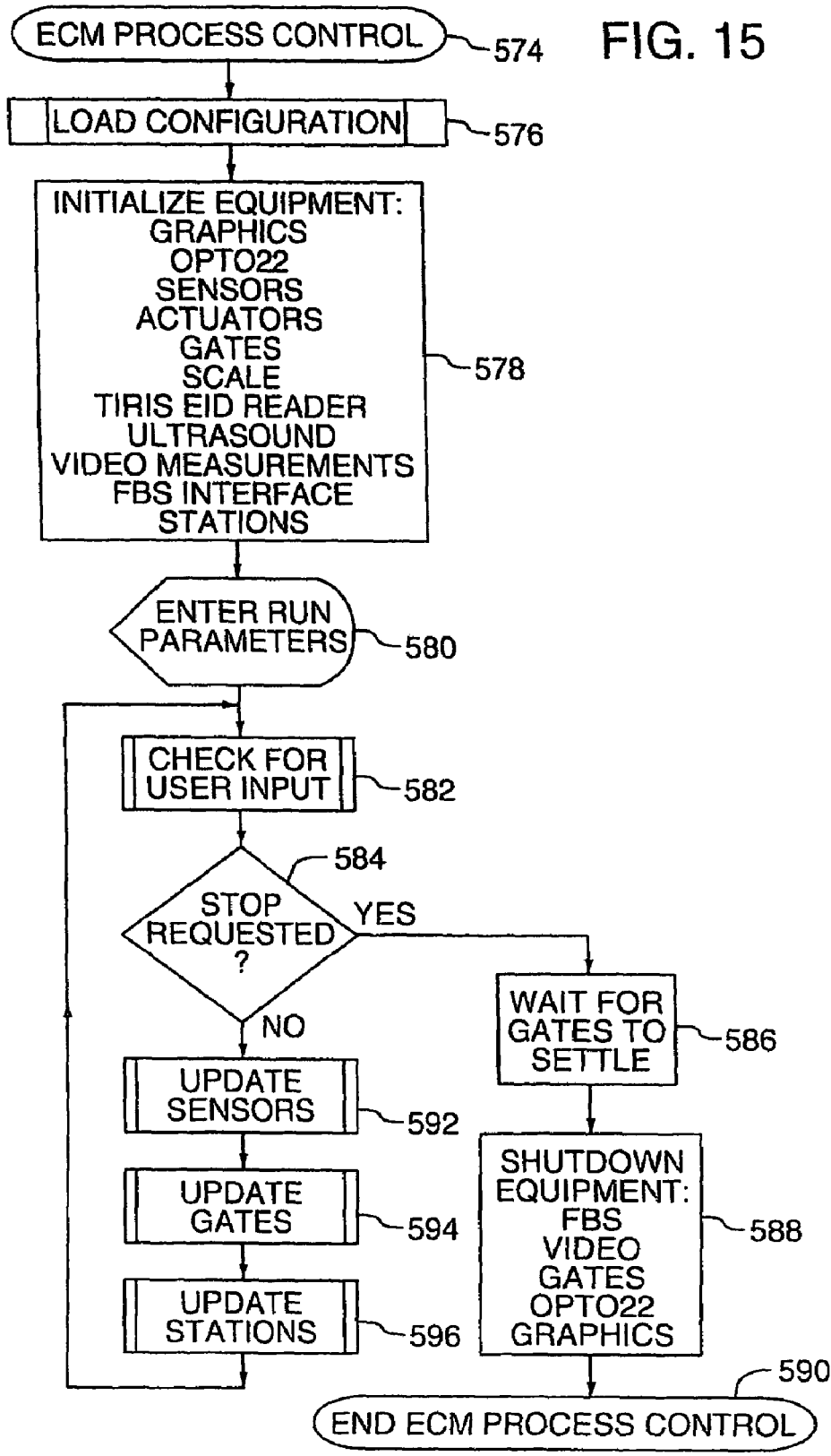
FIG. 15, is a flow diagram of the overall process control computer program for controlling the operation of the various computer-operated devices and equipment of the management system of the invention.

FIG. 15 is the overall ECM process control program in the process control computer that controls identification and shutdown of the various equipment used in the system including the sort pen gate sensors, the measuring and processing station sensors, the station gate actuators, the tiris EID reader, the ultrasound computer, the video measurement computer, the FBS computer interface and the like. The program is indicated generally at 574.

First, the particular configuration of the feedlot management system being used is loaded into the computer at step 576, and thereafter the various computers, interfaces, actuators, sensors, sort pen gates, and the like are initialized at step 578. Next, the various parameters to be used in the system are entered at step 580 through a data entry means. Next, the program checks for user inputs at step 582, and inquires whether any stopping of the operation of the system has been requested at step 584. If a stop has been requested, the system waits for the gates to settle at step 586 and then shuts down the equipment under its control at step 588 to end the ECM process control program at step 590.

If no stop of the system has been requested, then the program updates the sensors at step 592, updates the gates at 594 and updates the measurement and processing stations at step 596. Thereafter, the program returns to the portion of the program at step 582 that checks for user inputs and the program then continues to operate for the next animal proceeding through the system.

Figure 16:
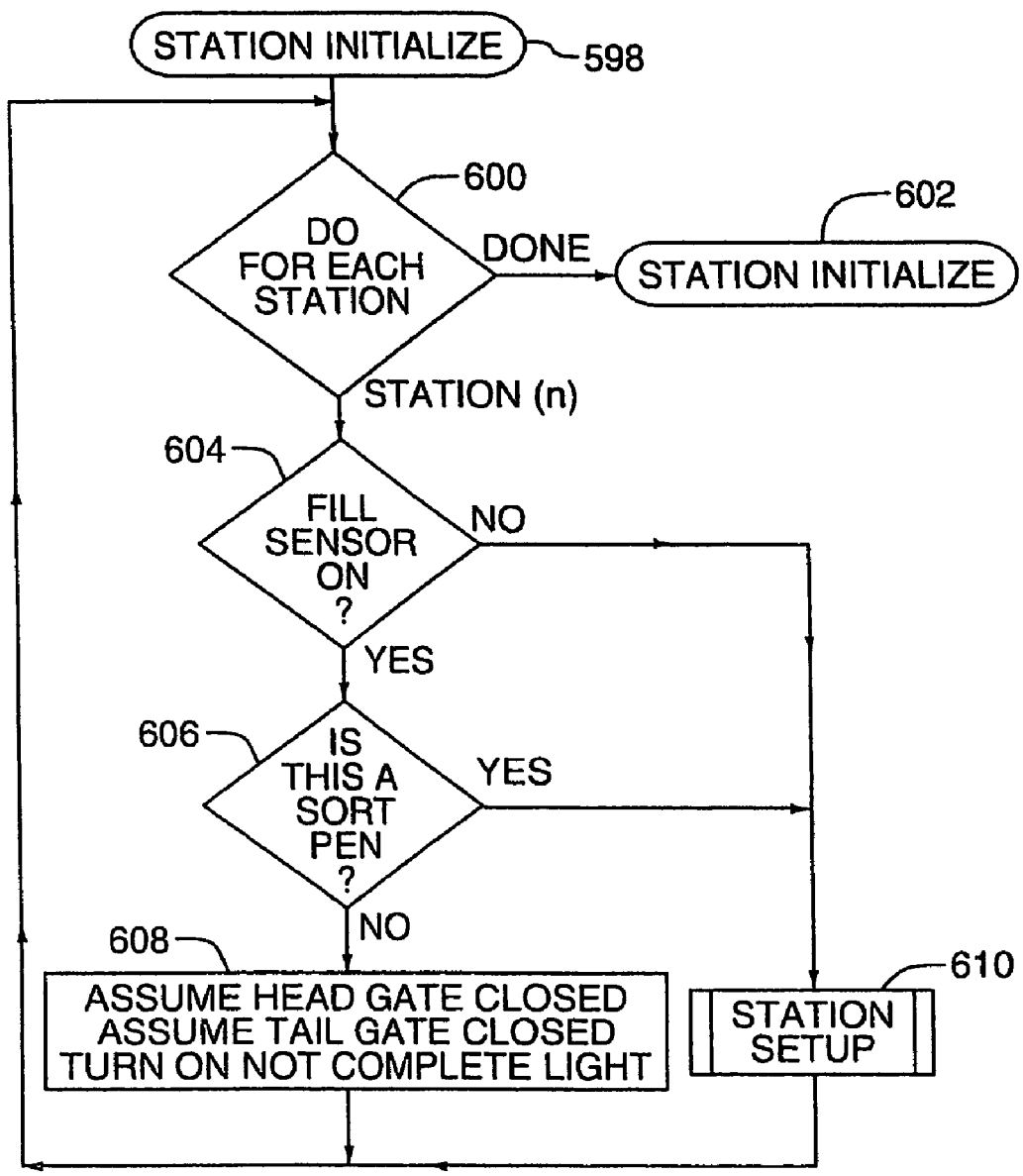
FIG. 16 is a flow diagram of a station initialization computer program for the various measuring and processing stations of the single-file chute shown in FIG. 5.

FIG. 16 is the station initialization program 598 that conditions each measuring and processing station for the receipt of the next animal. Each station is initialized at step 600, and when completed for all stations, the station initialization program ends at step 602. To initialize each station or pen, the program inquires whether the fill sensor in that station is on, at step 604. If the fill sensor is on, the program inquires whether this is a sort pen at step 606. If not, the program then assumes that the head gate is closed and that the tail gate is closed for that particular station at step 608, and then the program returns to its start at step 600 and repeats the sequence for each of (n) stations or pens. If at any station the program detects that a fill sensor is not on, at step 604 the program proceeds to a station setup step 610 and then back to the start of the programming sequence at step 600. If at step 606 of the programming sequence the program detects that this is a sort pen being initialized, then the program proceeds to the station setup step 610 before proceeding back to the start of the programming sequence at step 600.

Figure 17:
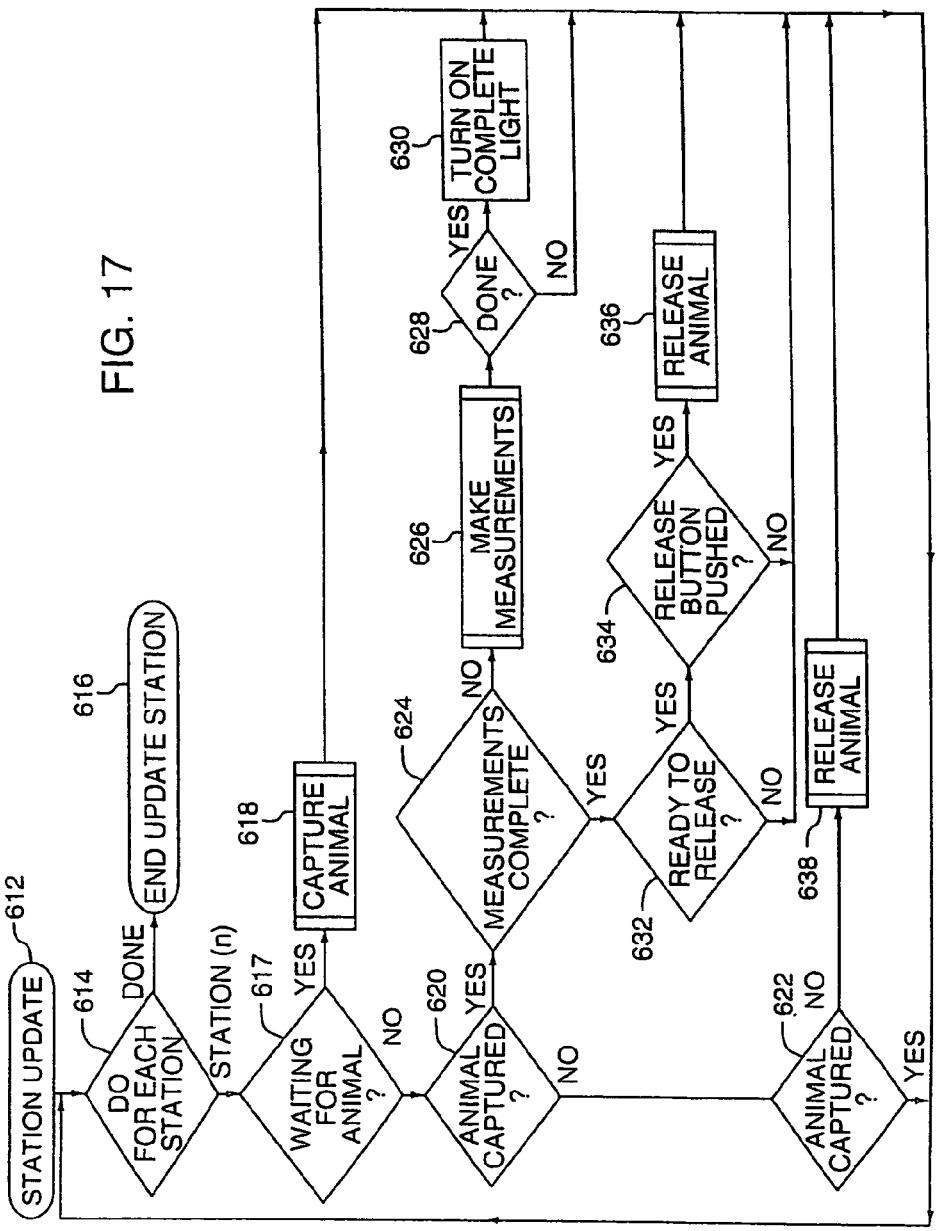
FIG. 17 is a flow diagram of a computer program used to update the data for each computer-operated measuring apparatus at each measuring and processing station of the system.

FIG. 17 is the flow chart for the "update stations" program 612. The first step in the program sequence is to update each station for the next animal as indicated at step 614. When each station of the total number of stations (n) has been updated, the update program for that station ends at step 616. The program resequences until all stations have been updated.

To update a station, the next step 616 of the program asks a station whether it is waiting for an animal. If it is, then it initiates the capture animal program at step 618, which will be described subsequently. After the capture animal program for a particular station has been run, the program sequences back to its start at step 614 and then proceeds to update the next station. If a particular station at sequencing step 616 of the program is not waiting for an animal, the program then asks whether an animal has been captured at step 620. If an animal has not been captured, it then asks at step 622 whether an animal has been released from the station. If an animal has been released, the program resequences to the beginning at step 614 to rerun the program for the next station. If for a particular station an animal is captured when the inquiry is made at step 620, the program next asks at step 624 whether the measurements are complete at that station. If the measurements are not complete, the program waits until the measurements are made at step 626.

Next, the program asks if the measurements have been completed at step 628 and if the answer is yes a light on the control panel is turned on at step 630 to indicate that the measurements are complete, and the program sequences back to the beginning at step 614. If the measurements are not complete, the program sequences back to the beginning and reruns until the measurements are complete and the "complete light" can be turned on.

If, at step 624 when the program inquires whether the measurements are complete and the answer is yes, the program then asks at step 632 whether the animal is ready for release. If the answer is no, the program sequences to the beginning and reruns through the sequences until the animal is ready for release. When the animal is ready for release at step 632 of the program, it then asks at step 634 whether the release button has been pushed. If it has, then the animal is released at step 636. If it has not, then the program sequences back to the beginning to rerun until the animal is released. If at step 622 of the program an animal has not been released, then the program commands that the animal be released at step 638 after which the program sequences back to the beginning to update the station for the next animal.

Figure 18:
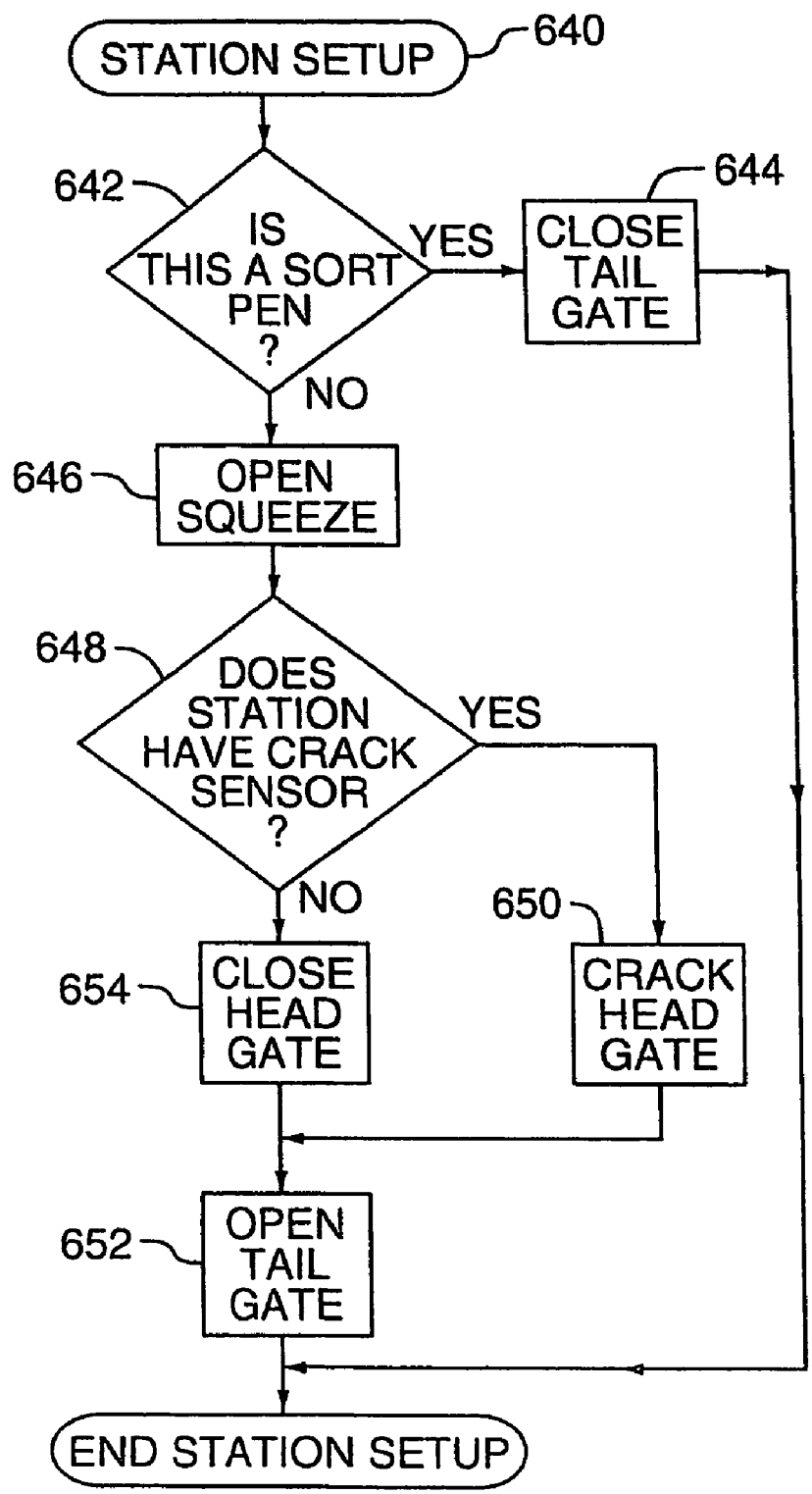
FIG. 18 is a flow diagram of a station setup computer program used to prepare each station for the receipt of an animal for measuring and processing.

FIG. 18 shows the flow chart for the "station setup" computer program 640. In the first step of the programming sequence the program asks whether this is a sort pen. If it is a sort pen, the sort pen entrance gate (indicated in the flow chart as the "tail gate" at step 644 is closed to end the station setup program for the sort pen.

If the station setup program is not being run for a sort pen, then the program commands that the squeeze gate, if any, be opened at 646. Next, the program inquires at step 648 whether the station has a crack sensor. If it does, then the program commands that the head gate be cracked at step 650. Then the program commands that the tail gate be opened at step 652 to end the setup program for that particular station.

If at the sequencing step 648 the station does not have a crack sensor, then the program commands that the station head gate be closed at step 654 and then that the tail gate be opened at step 652 to end the station setup program, at which point the station is ready to receive the next animal.

Figure 19:
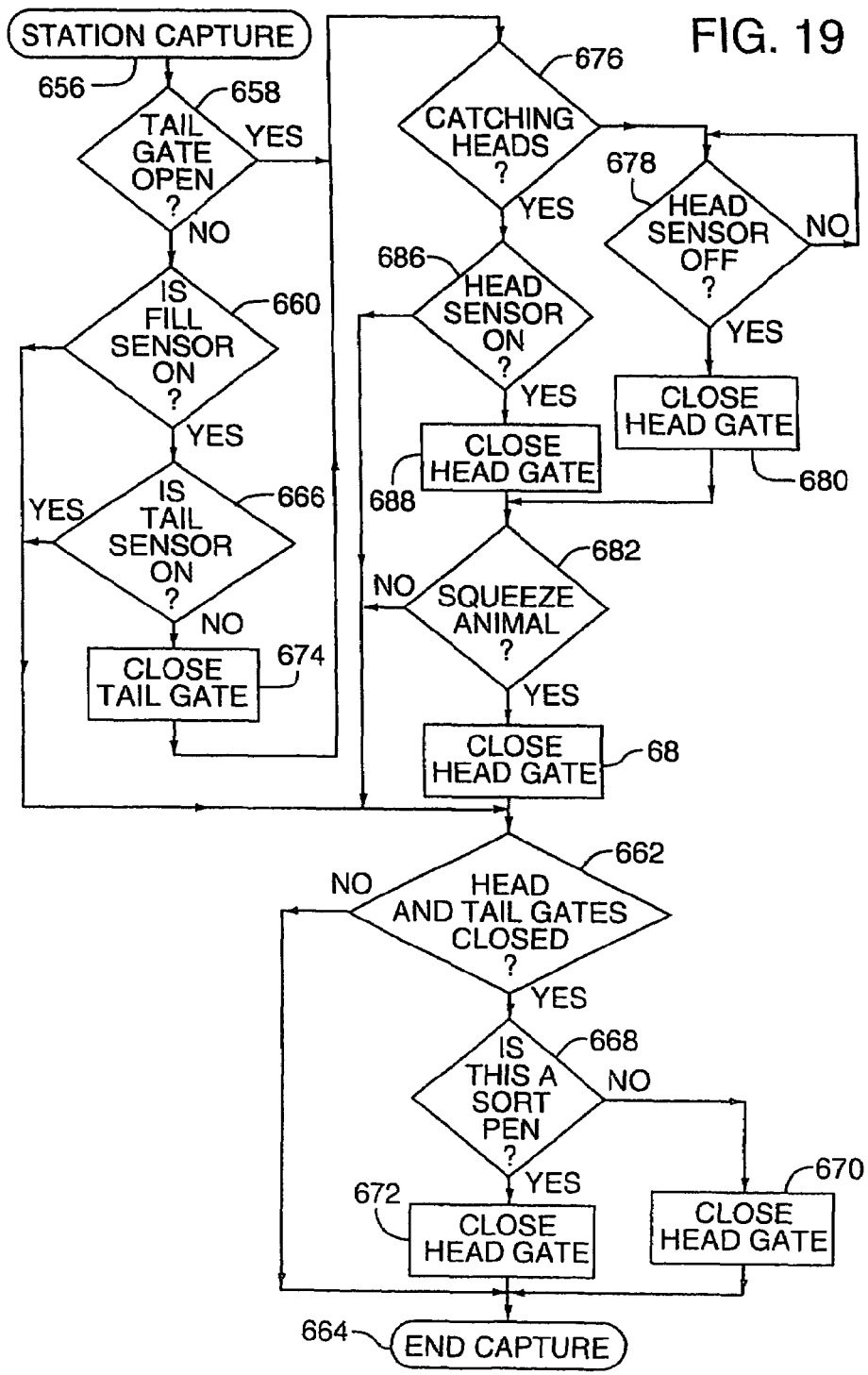
FIG. 19 is a flow diagram of a computer program used to ensure the capture of an animal within a measuring or processing station before measurements or processings are initiated at the station in the single-file chute shown in FIG. 5.

FIG. 19 is the flow chart for the "capture animal" program for each station, which, like the preceding programs, is run by the process control computer. The program, indicated at 656, first inquires whether the tail gate for a station is open at step 658. If the tail gate is not open, it inquires whether the fill sensor at the station is on at step 660. If the fill sensor is not on the program sequences to a point where it asks whether the head and tail gates are closed at step 662. If the head and tail gates are not closed, the program sequences to its end at step 664 because there is no animal present to be captured.

Returning to step 660 of the programming sequence, if the fill sensor is on, the program then inquires whether the tail sensor is on at step 666. If the tail sensor is on the program then sequences to step 662 to inquire whether the head and tail gates are closed. If the head and tail gates are closed, the programs inquires whether this is a sort pen at step 668. If it is not a sort pen, the program commands that the status light on the control panel be turned on to indicate that the measuring or processing at the station is not complete, at step 670. If at step 668 it is a sort pen, then the program commands that the animal's identity be recorded at step 672.

Returning to step 666, if the tail sensor is not on but the fill sensor is on, then the program commands that the tail gate be closed at step 674. Once the tail gate is closed, the program at step 676 inquires whether there is a head catcher at the station and if so whether the head is to be caught by it.

If the station has no head catcher, then the program at step 678 inquires whether the head sensor is off. If it is not off, nothing further happens until it does go off. Then the program commands the head gate to close at step 680. When the head gate closes the program inquires whether the station has a squeeze gate and if so whether the animal is to be squeezed, at step 682. If the animal is to be squeezed, the squeeze gate is commanded to close at step 684. After the squeeze gate is closed, the program sequences through the steps previously described at 662, 668, and 672 to the end of the capture program at 664.

If at step 676 there is an indication that there is a head catcher to be operated, the program inquires at step 686 whether the head sensor is on. If it is on then the head gate is commanded to close at step 688, and the program sequences through steps 682, 684, 662, 668 and 672 as previously described.

If at step 686, the head sensor is not on, then the program sequences to step 662 to inquire whether the head and tail gates are closed.

Figure 20A:
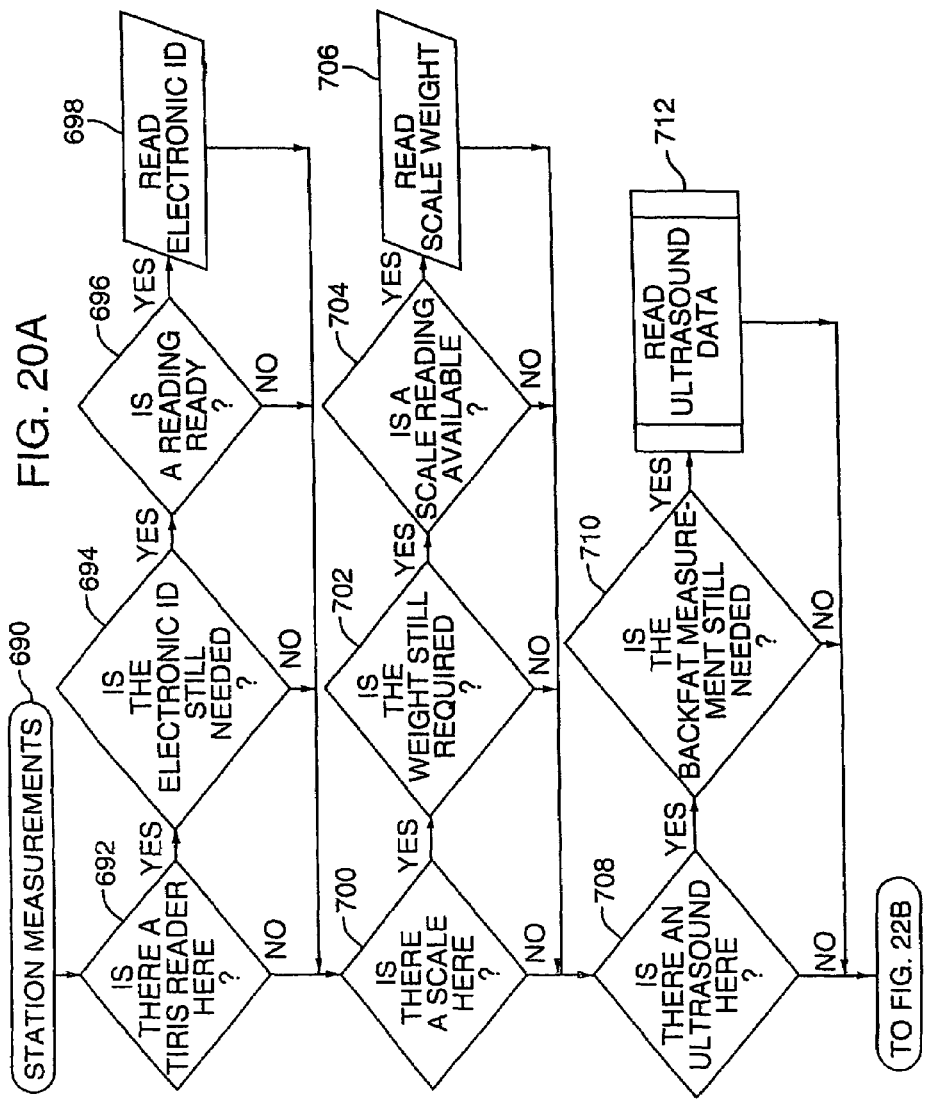
FIG. 20 is a flow diagram of a computer program used for making measurements at the various measuring stations of the single-file chute, including weight, external dimension and internal measurements.

The next program to be described is the "make measurements program, the flow diagram for which is shown in FIG. 20 and indicated generally at 690. This is the program of the process control computer that controls the operation of the computers that control the equipment for making the three basic measurements, namely a weight measurement, an external measurement via the video scanner, and an ultrasound measurement for backfat via the ultrasound machine. The program also controls the reading of the measurement data and its transmission to the FBS computer.

The first step 692 in the program is to inquire whether an animal needs to be identified through its EID tag, by asking whether there is a tiris reader. If there is a tiris reader the program inquires whether an electronic ID of the animal is still needed at step 694. If an electronic identification is needed, the program inquires whether an identity reading is ready at step 696. If the reading is ready, the program instructs the computer to read the animal's electronic identification at step 698. If at any step in the foregoing sequence, it is indicated that no electronic ID is needed or that the reading is not ready, the program proceeds to the next sequence of steps.

The sequence involves weighing, and the first step in the sequence is to inquire whether there is a scale at the station. If there is a scale at the station, the program inquires at step 708 whether a weight is required. If a weight is required the program asks if the scale reading is available at step 710. If the scale reading is available, the program instructs the computer to read the scale weight at step 712. If at any point in the foregoing weigh sequence it is indicated that a weight is not required or a weight reading is not available, the program sequences to the next series of steps for backfat measurement. The backfat steps start with an inquiry at step 708 whether there is an ultrasound machine at the station. If there is, the program inquires whether a backfat measurement is required at step 710. If a backfat measurement is required, the program commands the appropriate computer to read the ultrasound data at step 712. If a backfat measurement is not available or needed, or once the ultrasound data has been read, the program sequences to the next series of steps relating to video measurements.

The first inquiry at the next sequence of steps as indicated at step 714 is whether there is a video measurement interface at the particular station. If there is, the program inquires whether a hip-height measurement is still required at step 716. If it is, the program inquires whether the video measurements are ready to be read at step 718. If they are, a reading of the video measurements of the animal is made at step 720, and the program sequences to the next series of steps beginning at step 722. If at any point in the video measurement sequence of steps it is indicated that a measurement is not required or that the video measurements are not available to be read, the program sequences to the next series of steps.

At step 722 the program inquires whether there is an FBS computer interface at the station. If there is, the program inquires whether a sort pen is required at step 724. If one is required, the program inquires whether all measurements are completed at step 726. If all measurements are completed, then the program transmits the recorded measurement data to the FBS computer. It also requests the FBS computer to assign a sort pen to the animal at step 728. If at any point in the foregoing sequence of steps, beginning at step 722, there is no sort pen required or all measurements are not complete, the program proceeds to the end at step 730.

From the foregoing description of the "make measurements" program it will be apparent that this program can be used to control the appropriate computer and equipment at each measurement station to make the appropriate measurements, then record them and transmit the measurement data to the FBS computer, and in turn receive a sort pen assignment from the FBS computer based on such measurement data.

The next program to be described is the "release animal" program, the flow diagram of which is shown in FIG. 21 and indicated generally at 732.

The first step in the release animal programming sequence, at step 734, is to inquire whether there is an animal at the particular station. If there is no animal, the program sequences to command the head gate to open and the squeeze gate to open at step 736. Then the program sequences to inquire whether the fill sensor is off at step 738. If the fill sensor is not off, the program sequences to the end of the station release program at step 740 and the animal is not released.

If the fill sensor is off at step 738 then the program inquires whether the head sensor is off at step 742. If the head sensor is off, then the program commands the station setup program to start at step 744 and completes its sequencing at step 740. If the head sensor is not off at step 742, the program sequences to the end of the program and the animal is not released.

If at step 734 of the program sequence there is an animal in the station, the next inquiry is whether this is a sort pen, at step 736. If it is a sort pen, then the program sequences to pass the animal data to the next station at step 748 and then to turn the status lights off on the control panel at step 750. Thereafter, the program sequences to step 736 to open the squeeze and head gates to release the animal.

If at step 746 in the sequence the indication is that the station is not a sort pen then the program sequences to the next step 752 to inquire whether the next station is ready for an animal. If the answer is no, the program sequences to the end at step 740 and the animal is not released. If the answer is yes at step 752, then the animal data is passed to the next station at step 748, the status lights are turned off at step 750 and the program sequences to step 736 to release the animal.

The next program to be described, with reference to the flow diagram of FIG. 22, is the "read ultrasound data" program 754. The first step in the program sequence is to inquire whether a backfat reading is available from the ultrasound computer at step 756. If one is not available, the program sequences to the end at step 758. If a reading is available, the computer is instructed to read the backfat reading from the ultrasound at step 760. Next, the program inquires whether the backfat reading is good at step 762. If it is not, then the program commands the computer to turn on the bad reading status light on the control panel at step 764 and the program sequences to the end. If the reading is good then the "good reading" status light is turned on at the control panel at step 766. Then the good reading is added to the list of backfat readings for that animal at step 768.

After the reading, the program commands the computer at step 770 to count the number of other readings that are within 0.2 inches, as indicated at step 772. When that has been done, the program sequences back to step 770 until all such readings in the list have been counted as indicated. When that is done, the program sequences to step 774 and inquires whether there are four or more close readings. If there are four or more close readings, the next step 776 is to average the close readings. Then the computer turns on the "backfat complete" status light on the control panel at step 778 and the program ends.

If at step 774 there are not four or more close readings, then the program sequences to step 780 and asks if there are eight or more readings in the list. If there are not, the program sequences to the end at step 758. If there are, the program instructs the computer to clear the list and reset to start over at step 782 and then sequences to the end of the program at step 758.

Figure 23:
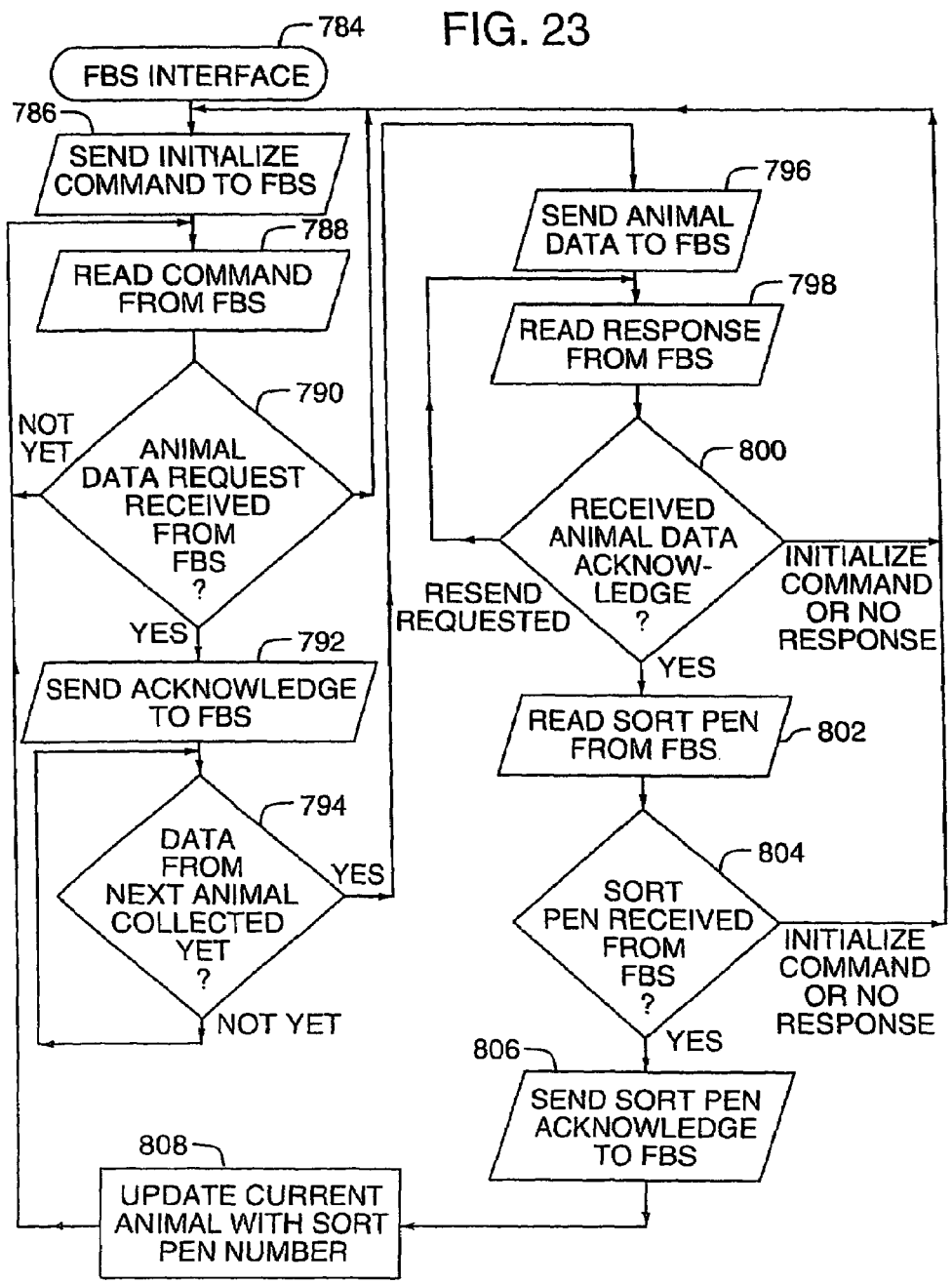
FIG. 23 is a flow chart of a computer program used to interface the process control and other computers used for collecting data at the various feedlot measuring, processing and sorting stations or pens with the main feedlot business system (FBS) computer so that data can be passed back and forth between the FBS computer and the various processing computers used in the overall computer control system.

The next program to be described is the FBS computer interface program 784 described with reference to the flow diagram of FIG. 23. This program operates the FBS interface indicated at 246 in FIG. 6. The first step 786 in the program is to send an initialize command to the FBS computer. The next step 788 in the program is to read a command from the FBS computer. The next 790 step in the program is to inquire whether an animal data request has been received from the FBS computer. If not, the program sequences back to step 788 to await a command from the FBS computer. If there is no command from the FBS computer or no response, the program sequences back to the beginning to send an initialize command to the FBS computer.

If at step 790 an animal data request is received from the FBS computer, an acknowledgement is sent to the FBS computer at step 792. Next, the program inquires whether data from the next animal is collected yet, at step 794. If the data has not yet been collected, the program returns to step 794 to await the collection of data. When data for the next animal has been collected, the program sequences to step 796 and sends the animal data to the FBS computer. Next, at step 798 the program waits to read a response from the FBS computer. Then, the program awaits receipt of an animal data acknowledgement from the FBS computer at step 800. If not received, the program requests the FBS computer to resend an acknowledgement. Upon an initialize command or no response from the FBS computer, the program sequences back to the initial step 786.

If the program receives an acknowledgement from the FBS computer that the animal data was received, the program next reads the sort pen assignment received from the FBS computer at step 802. Next, at step 804, the program inquires whether the sort pen assignment was received from the FBS computer. At this point if there is an initialize command from the FBS computer or no sort pen assignment from the FBS computer, the program sequences back to the initial step 786.

If there is a sort pen assignment received from the FBS computer, the program sends a sort pen acknowledgement to the FBS computer at step 806. Then, at step 808 the program commands the computer to update the current animal with its assigned sort pen number, in other words, to correlate the new sort pen assignment with the identified animal. The program then returns to step 788, awaiting a command from the FBS computer.

Figure 24:
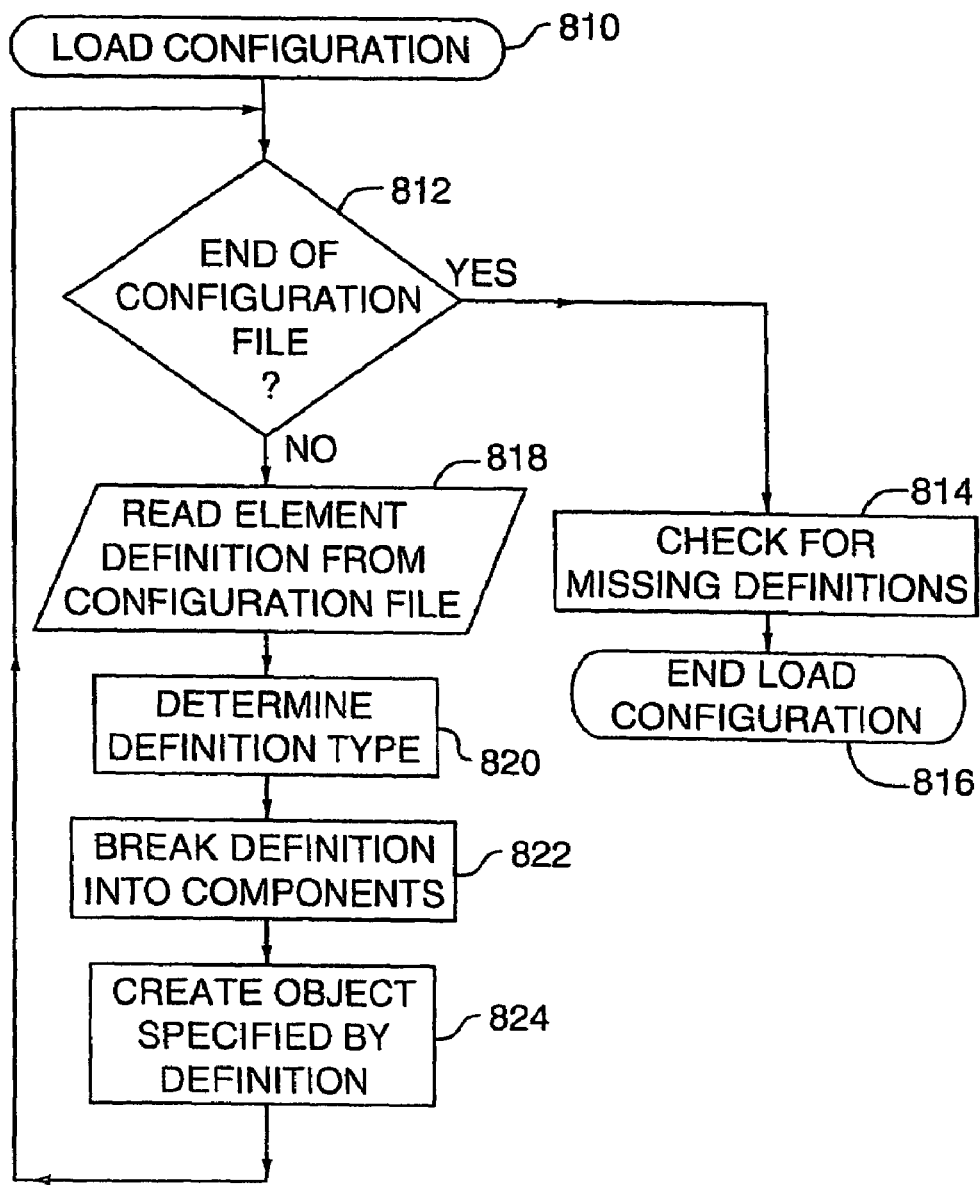
FIG. 24 is a flow diagram of a computer program used for loading station configuration information into the computer system for a particular feedlot cattle management system.

Finally, there is a program for loading the ECM (cattle management system) station configuration information into the process control computer. This program is diagrammed in FIG. 24 and indicated generally at 810. In the first step of its sequence the program inquires whether this is the end of the configuration file, at step 812. If the answer is yes, then the program sequences to step 814 to check for any missing definitions. Then the load configuration program ends at step 816. If the configuration file is not fully loaded, then from step 812 the program sequences to read the element definition from the configuration file at step 818. Then the program determines the definition type at step 820 and breaks the definition into its components at step 822 and creates the object specified by the definition at step 824 before sequencing back to the beginning of the load configuration program.

F. Summary

From the foregoing it will be appreciated that the disclosed computerized cattle management system and method provides a highly flexible system and method for measuring, sorting and processing animals, either on a group basis or an individual basis or in a combination of group and individual basis. It furthermore proves a means and method for projecting, on an individual animal basis, when that animal will be ready to be shipped from the feedlot to the packing plant for slaughter and what that animal's optimum finish weight will be. The system also provides a means and method whereby the costs of maintaining animals in the feedlot can be determined on an individual animal basis so that such costs, on an individual animal basis, can be assessed to the animal's owners, thereby providing a highly efficient cost management tool.

With the management system of the present invention, no longer is it necessary to treat a group of animals received in a feedlot as a group throughout its period of stay in the feedlot. Instead, different groups of animals as received in a feedlot can be mixed with other groups regardless of ownership, based on management criteria such as animal type, DTF, OEW or other factors. Since each animal can be identified electronically at any time and at any place during its stay in the feedlot, with its ownership easily determined, it can be grouped with other animals with similar physical characteristics or OED's rather than being kept in a common ownership group while in the feedlot. Similarly, when animals are ready for slaughter, they can be sent to the packing plant without regard to ownership because their EID tags will identify them at packing plant as to ownership and thus costs and proceeds can be properly assessed and credited without regard to group.

From the foregoing, it should be apparent that a particular animal may be in one group or lot when it arrives in a feedlot, may be moved to a different group within a feed pen during the feeding period, and may be sorted into a marketing group different than its pen feeding group when it is finally ready for shipment to the packing plant. All of this is made possible by the ability to electronically identify each animal by ownership and physical characteristics and costs at any time, irrespective of the group it happens to be in at any given time.

Having illustrated and described the principals of the invention by what are currently several preferred embodiments, it should be apparent that those embodiments can be modified in arrangement and detail without departing from those principals. I claim as my invention all such embodiments and variations thereof, and their equivalence, as come within the true spirit and scope of the following claims.

TABLE 3A

Cattle Received Report by Load

Period Mar. 18, 1994 to Mar. 20, 1994  
Research Division  
Agri-Research Feeders  
Lot: 495  
CIR117  
Seq 13  
Page

| Pen Number | Date Received | Load | | | Weight | | | | | Purchase Cost | |
|---|---|---|---|---|---|---|---|---|---|---|---|
| | | | | | Average | | | Totals | | | |
| | | Number | Head | Sex | Pay | Rec | Shrink | Pay | Rec | Total | $/CWT |
| L4 | Mar. 19, 1994 | 1 | 32 | HF | 678 | 678 | 0.00% | 21,680 | 21,680 | 16,476.80 | 7600 |
| | | AGE | | | YEARLING | | | 160.00 | | | |
| | | BACKGROUND | | | WHEAT PASTURE | | | 100.00 | | | |
| | | BREED OF FEEDER | | | ANGUS CROSS | | | 25.00 | | | |
| | | | | | CHAROLAIS | | | 6.25 | | | |
| | | | | | HEREFORD | | | 28.00 | | | |
| | | | | | HOLSTEIN CROSS | | | 18.75 | | | |
| | | | | | SHORTHORN X | | | 22.00 | | | |
| | | DAYS IN PASTURE | | | 154-161 | | | 100.00 | | | |
| | | DISPOSITION | | | DOCILE | | | 95.00 | | | |
| | | HEALTH SCORE | | | EXCELLENT | | | 100.00 | | | |
| | | MARKET TYPE | | | DIRECT | | | 100.00 | | | |
| | | NUTRITION | | | WHEAT PASTURE | | | 100.00 | | | |
| | | STRESS SCORE | | | EXCELLENT | | | 100.00 | | | |
| | | WEATHER/ ARRIVAL | | | SUNNY & MILD | | | 100.00 | | | |
| Number of Loads: | | 1 | 32 | | 678 | 678 | 0.00% | 21,680 | 21,680 | 16,476.80 | 76.00 |
| HF-HEIFERS | | 1 | 32 | | 678 | 678 | 0.00% | 21,680 | 21,680 | 16,476.80 | 76.00 |
| | | AGE | | | YEARLING | | | 100.00% | | | |
| | | BREED OF FEEDER | | | ANGUS CROSS | | | 25.00% | | | |
| | | | | | CHAROLAIS | | | 6.25% | | | |
| | | | | | HEREFORD | | | 28.00% | | | |
| | | | | | HOLSTEIN CROSS | | | 18.75% | | | |
| | | | | | SHORTHORN X | | | 22.00% | | | |
| | | BACKGROUND | | | WHEAT PASTURE | | | 100.00% | | | |
| | | DISPOSITION | | | COCILE | | | 95.00% | | | |
| | | HEALTH SCORE | | | EXCELLENT | | | 100.00% | | | |
| | | MARKET TYPE | | | DIRECT | | | 100.00% | | | |
| | | NUTRITION | | | WHEAT PASTURE | | | 100.00% | | | |
| | | DAYS ON PASTURE | | | 154-161 | | | 100.00% | | | |
| | | STRESS SCORE | | | EXCELLENT | | | 100.00% | | | |
| | | WEATHER/ ARRIVAL | | | SUNNY & MILD | | | 100.00% | | | |

TABLE 3B

Pen Assignment Summary  
Source Lot: 495  
Source Pen: 59  
Sort Type: DAYS TO FINISH

| | Pen | | | | | | |
|---|---|---|---|---|---|---|---|
| | 1 | 2 | 3 | 4 | 5 | 6 | 7 |
| Lot | 495 | 495 | 495 | | | | |
| Feed Pen | 59 | 57 | 58 | | | | |

TABLE 3B-continued

Pen Assignment Summary
Source Lot: 495
Source Pen: 59
Sort Type: DAYS TO FINISH

|  | Pen | | | | | | |
| --- | --- | --- | --- | --- | --- | --- | --- |
|  | 1 | 2 | 3 | 4 | 5 | 6 | 7 |
| Head | 10 | 11 | 11 | | | | |
| Average | 98 | 79 | 83 | | | | |
| STD | 38 | 41 | 56 | | | | |
| Max | 154 | 154 | 164 | | | | |
| Min | 36 | 17 | 9 | | | | |
| Range | 118 | 137 | 155 | | | | |
| Projected Finish Weight | | | | | | | |
| Average | 1066 | 1093 | 997 | | | | |
| STD | 158 | 137 | 126 | | | | |
| Max | 1260 | 1260 | 1177 | | | | |
| Min | 830 | 876 | 815 | | | | |
| Range | 430 | 384 | 362 | | | | |
| Current Weight | | | | | | | |
| Average | 787 | 875 | 766 | | | | |
| STD | 120 | 66 | 66 | | | | |
| Max | 1035 | 965 | 843 | | | | |
| Min | 627 | 766 | 648 | | | | |
| Range | 408 | 199 | 195 | | | | |
| Frame | | | | | | | |
| Average | 5 | 6 | 4 | | | | |
| STD | 1 | 1 | 1 | | | | |
| Max | 7 | 7 | 7 | | | | |
| Min | 3 | 3 | 3 | | | | |
| Range | 4 | 4 | 4 | | | | |
| Current Back Fat | | | | | | | |
| Average | .22 | .30 | .33 | | | | |
| STD | .12 | .11 | .19 | | | | |
| Max | .42 | .53 | .75 | | | | |
| Min | .09 | .17 | .12 | | | | |
| Range | .33 | .36 | .63 | | | | |

TABLE 3C

PEN ASSIGNMENT DETAIL

LOT: 495
PEN: 57                                    Thu Apr 28 1994
Sort Pen: 2                                      07:35:12
Run Seq: 206                                       Page 1

| EID | VID | DTF | OFW | CWT | ADG | FM | BF |
| --- | --- | --- | --- | --- | --- | --- | --- |
| Ship Window: May 14, 1994 TO Sep 28, 1994 | | | | | | | |
| 16817175 | 11 | 16 | 876 | 826 | 3.13 | 3 | 0.53 |
| 16817094 | 4 | 32 | 1004 | 905 | 3.09 | 5 | 0.41 |
| 16817763 | 22 | 45 | 1034 | 942 | 2.04 | 5 | 0.25 |
| 16816164 | 9 | 59 | 1089 | 929 | 2.71 | 7 | 0.22 |
| 16814011 | 5 | 60 | 912 | 766 | 2.43 | 3 | 0.41 |
| 16816227 | 24 | 75 | 1024 | 798 | 3.01 | 5 | 0.36 |
| 16816430 | 16 | 83 | 1132 | 897 | 2.83 | 7 | 0.25 |
| 16815742 | 28 | 98 | 1260 | 965 | 3.01 | 7 | 0.17 |
| 16816005 | 34 | 115 | 1260 | 931 | 2.86 | 7 | 0.31 |
| 16814141 | 19 | 122 | 1175 | 843 | 2.72 | 7 | 0.17 |
| 16813043 | 32 | 153 | 1260 | 824 | 2.85 | 5 | 0.24 |

TABLE 3D

MARKETING YARD SHEET
INDIVIDUAL ANIMAL LEVEL

Apr 12, 1994                                         C1###
17:55:03                                              page
Measurement Date: Mar. 30, 1994
DIV: AGR
SEX: HF
Owner: Agri Research
Origin: Little
Type: Crossbred Heifers

| | | | | Projected | | | | Weights | | DOF | | | Rution | |
| --- | --- | --- | --- | --- | --- | --- | --- | --- | --- | --- | --- | --- | --- | --- |
| TAG | PEN | HGp | LOT | DTF | Date | OFW | YG | BE | CURR | PUR | CPD | LPD | ID | No. | Days |
| 25 | 59 | | 495 | 38 | 0506 | 815 | 3.0 | 117.25 | 711 | 678 | 10 | | 10 | 8 | 10 |
| 11 | 59 | | 495 | 46 | 0514 | 876 | 3.0 | 117.25 | 757 | 678 | 10 | | 10 | 8 | 10 |
| 15 | 59 | | 495 | 53 | 0522 | 896 | 3.0 | 117.25 | 757 | 678 | 10 | | | 8 | 10 |
| 18 | 59 | | 495 | 59 | 0527 | 821 | 3.0 | 117.25 | 668 | 678 | 10 | | 10 | 8 | 10 |
| 4 | 59 | | 495 | 62 | 0530 | 1004 | 3.0 | 117.25 | 843 | 678 | 10 | | 10 | 8 | 10 |
| 3 | 59 | | 495 | 65 | 0602 | 848 | 3.0 | 117.25 | 679 | 678 | 10 | | 10 | 8 | 10 |
| 14 | 59 | | 495 | 68 | 0606 | 904 | 3.0 | 117.25 | 727 | 678 | 10 | | 10 | 8 | 10 |
| 22 | 59 | | 495 | 75 | 0612 | 1034 | 2.0 | 117.25 | 817 | 678 | 10 | | 10 | 8 | 10 |
| 9 | 59 | | 495 | 89 | 0626 | 1089 | 2.0 | 117.25 | 832 | 678 | 10 | | 10 | 8 | 10 |
| 5 | 59 | | 495 | 90 | 0627 | 912 | 3.0 | 117.25 | 679 | 678 | 10 | | 10 | 8 | 10 |
| 17 | 59 | | 495 | 92 | 0630 | 830 | 3.0 | 117.25 | 576 | 678 | 10 | | 10 | 8 | 10 |
| 20 | 58 | | 495 | 97 | 0705 | 972 | 3.0 | 117.25 | 704 | 678 | 10 | | 10 | 8 | 10 |
| 2 | 58 | | 495 | 98 | 0706 | 965 | 3.0 | 117.25 | 710 | 678 | 10 | | 10 | 8 | 10 |
| 24 | 58 | | 495 | 104 | 0712 | 1024 | 2.0 | 117.25 | 722 | 678 | 10 | | 10 | 8 | 10 |
| 26 | 58 | | 495 | 104 | 0712 | 1044 | 2.0 | 117.25 | 742 | 678 | 10 | | 10 | 8 | 10 |
| 30 | 58 | | 495 | 107 | 0715 | 1034 | 3.0 | 117.25 | 755 | 678 | 10 | | 10 | 8 | 10 |

TABLE 3D-continued

MARKETING YARD SHEET
INDIVIDUAL ANIMAL LEVEL

| 13 | 58 | 495 | 107 | 0715 | 1012 | 3.0 | 117.25 | 733 | 678 | 10 | 10 | 8 | 10 |
|---|---|---|---|---|---|---|---|---|---|---|---|---|---|
| 16 | 58 | 495 | 113 | 0720 | 1132 | 2.0 | 117.25 | 805 | 678 | 10 | 10 | 8 | 10 |
| 21 | 58 | 495 | 113 | 0720 | 990 | 3.0 | 117.25 | 697 | 678 | 10 | 10 | 8 | 10 |
| 23 | 58 | 495 | 119 | 0726 | 1260 | 2.0 | 117.25 | 915 | 678 | 10 | 10 | 8 | 10 |
| 28 | 58 | 495 | 128 | 0804 | 1260 | 2.0 | 117.25 | 890 | 678 | 10 | 10 | 8 | 10 |
| 29 | 58 | 495 | 128 | 0805 | 1090 | 3.0 | 117.25 | 738 | 678 | 10 | 10 | 8 | 10 |
| 34 | 57 | 495 | 144 | 0821 | 1260 | 2.0 | 117.25 | 841 | 678 | 10 | 10 | 8 | 10 |
| 19 | 57 | 495 | 152 | 0828 | 1175 | 3.0 | 117.25 | 757 | 678 | 10 | 10 | 8 | 10 |

| | | | | ADG | | | Feed intake | | | TREATS/HD | | PROCS/Hd | | TOTALS/Hd | |
|---|---|---|---|---|---|---|---|---|---|---|---|---|---|---|---|
| TAG | PEN | HGp | LOT | CPD | LPD | ID | PCP | ACP | L7D | ID | Proj | Act | Proj | Act | Proj | TD |
| 25 | 59 | | 495 | 5.4 | .0 | 5.4 | 18 | 22 | 23 | 22 | 1 | .00 | 5 | 4.75 | 6 | 4.75 |
| 11 | 59 | | 495 | 5.8 | .0 | 5.8 | 18 | 24 | 25 | 24 | 1 | .00 | 5 | 4.75 | 6 | 4.75 |
| 15 | 59 | | 495 | 5.8 | .0 | 5.8 | 18 | 24 | 25 | 24 | 1 | .00 | 5 | 4.75 | 6 | 4.75 |
| 18 | 59 | | 495 | 5.1 | .0 | 5.1 | 18 | 21 | 22 | 2 | 1 | .00 | 5 | 4.75 | 6 | 4.75 |
| 4 | 59 | | 495 | 6.4 | .0 | 6.4 | 18 | 27 | 28 | 27 | 1 | .00 | 5 | 4.75 | 6 | 4.75 |
| 3 | 59 | | 495 | 5.2 | .0 | 5.2 | 18 | 21 | 22 | 21 | 1 | .00 | 5 | 4.75 | 6 | 4.75 |
| 14 | 59 | | 495 | .6 | .0 | .6 | 18 | 23 | 24 | 23 | 1 | .00 | 5 | 4.75 | 6 | 4.75 |
| 22 | 59 | | 495 | 6.2 | .0 | 6.2 | 18 | 26 | 27 | 26 | 1 | .00 | 5 | 4.75 | 6 | 4.75 |
| 9 | 59 | | 495 | 2.4 | .0 | 2.4 | 18 | 26 | 27 | 26 | 1 | .00 | 5 | 4.75 | 6 | 4.75 |
| 5 | 59 | | 495 | 2.0 | .0 | 2.0 | 18 | 21 | 22 | 21 | 1 | .00 | 5 | 4.75 | 6 | 4.75 |
| 17 | 59 | | 495 | 4.4 | .0 | 4.4 | 18 | 18 | 19 | 18 | 1 | .00 | 5 | 4.75 | 6 | 4.75 |
| 20 | 58 | | 495 | 5.4 | .0 | 5.4 | 18 | 22 | 23 | 22 | 1 | .00 | 5 | 4.75 | 6 | 4.75 |
| 2 | 58 | | 495 | 5.4 | .0 | 5.4 | 18 | 22 | 23 | 22 | 1 | .00 | 5 | 4.75 | 6 | 4.75 |
| 24 | 58 | | 495 | 5.5 | .0 | 5.5 | 18 | 23 | 24 | 23 | 1 | .00 | 5 | 4.75 | 6 | 4.75 |
| 26 | 58 | | 495 | 5.7 | .0 | 5.7 | 18 | 23 | 24 | 23 | 1 | .00 | 5 | 4.75 | 6 | 4.75 |
| 30 | 58 | | 495 | 2.4 | .0 | 2.4 | 18 | 24 | 25 | 24 | 1 | .00 | 5 | 4.75 | 6 | 4.75 |
| 13 | 58 | | 495 | 5.6 | .0 | 5.6 | 18 | 23 | 24 | 23 | 1 | .00 | 5 | 4.75 | 6 | 4.75 |
| 16 | 58 | | 495 | 6.1 | .0 | 6.1 | 18 | 25 | 26 | 25 | 1 | .00 | 5 | 4.75 | 6 | 4.75 |
| 21 | 58 | | 495 | 5.3 | .0 | 5.3 | 18 | 22 | 23 | 22 | 1 | .00 | 5 | 4.75 | 6 | 4.75 |
| 23 | 58 | | 495 | 7.0 | .0 | 7.0 | 18 | 29 | 30 | 29 | 1 | .00 | 5 | 4.75 | 6 | 4.75 |
| 28 | 58 | | 495 | 6.8 | .0 | 6.8 | 18 | 28 | 29 | 28 | 1 | .00 | 5 | 4.75 | 6 | 4.75 |
| 29 | 58 | | 495 | 5.6 | .0 | 5.6 | 18 | 23 | 24 | 23 | 1 | .00 | 5 | 4.75 | 6 | 4.75 |
| 34 | 57 | | 495 | 6.4 | .0 | 6.4 | 18 | 27 | 28 | 27 | 1 | .00 | 5 | 4.75 | 6 | 4.75 |
| 19 | 57 | | 495 | 5.8 | .0 | 5.8 | 18 | 24 | 25 | 24 | 1 | .00 | 5 | 4.75 | 6 | 4.75 |

TABLE 3E

MARKETING YARD SHEET
INDIVIDUAL ANIMAL LEVEL

Apr. 27, 1994  
17:55:11  
Measurement Date: Apr. 22, 1994  
DIV: AGR  
SEX: HF  
Owner: Agri Research  
Origin: Little  
Type: Crossbred Heifers C1####  
page 1

| | | | | Projected | | | | | Weights | | DOF | | | Rution | |
|---|---|---|---|---|---|---|---|---|---|---|---|---|---|---|---|
| TAG | PEN | HGp | LOT | DTF | Date | OFW | YG | BE | CURR | PUR | CPD | LPD | ID | No. | Days |
| 25 | 59 | A | 495 | 21 | 0513 | 869 | 3.0 | 118.39 | 811 | 678 | 24 | 10 | 34 | 6 | 12 |
| 11 | 59 | A | 495 | 24 | 0156 | 888 | 3.0 | 118.04 | 826 | 678 | 24 | 10 | 34 | 6 | 12 |
| 15 | 59 | A | 495 | 32 | 0524 | 896 | 3.0 | 117.07 | 813 | 678 | 24 | 10 | 34 | 6 | 12 |
| 4 | 59 | A | 495 | 34 | 0526 | 993 | 3.0 | 117.82 | 905 | 678 | 24 | 10 | 34 | 6 | 12 |
| 3 | 59 | A | 495 | 36 | 0528 | 863 | 3.0 | 116.01 | 769 | 678 | 24 | 10 | 34 | 6 | 12 |
| 18 | 59 | A | 495 | 43 | 0604 | 856 | 3.0 | 114.76 | 744 | 678 | 24 | 10 | 34 | 6 | 12 |
| 14 | 59 | B | 495 | 43 | 0604 | 905 | 3.0 | 115.60 | 793 | 678 | 24 | 10 | 34 | 6 | 12 |
| 22 | 59 | B | 495 | 51 | 0612 | 1089 | 2.0 | 115.92 | 942 | 678 | 24 | 10 | 34 | 6 | 12 |
| 5 | 59 | B | 495 | 56 | 0617 | 912 | 3.0 | 113.99 | 766 | 678 | 24 | 10 | 34 | 6 | 12 |
| 17 | 59 | B | 495 | 58 | 0619 | 787 | 3.0 | 109.23 | 628 | 678 | 24 | 10 | 34 | 6 | 12 |
| 9 | 59 | B | 495 | 68 | 0629 | 1127 | 2.0 | 114.30 | 929 | 678 | 24 | 10 | 34 | 6 | 12 |
| 2 | 58 | A | 495 | 68 | 0629 | 970 | 3.0 | 113.64 | 793 | 678 | 24 | 10 | 34 | 6 | 12 |
| 16 | 58 | A | 495 | 68 | 0629 | 1095 | 2.0 | 113.62 | 897 | 678 | 24 | 10 | 34 | 6 | 12 |
| 20 | 58 | A | 495 | 74 | 0705 | 988 | 3.0 | 112.04 | 785 | 678 | 24 | 10 | 34 | 6 | 12 |
| 23 | 58 | A | 495 | 78 | 0709 | 1260 | 2.0 | 116.07 | 1035 | 678 | 24 | 10 | 34 | 6 | 12 |
| 24 | 58 | A | 495 | 82 | 0713 | 1035 | 2.0 | 110.62 | 798 | 678 | 24 | 10 | 34 | 6 | 12 |

TABLE 3E-continued

MARKETING YARD SHEET
INDIVIDUAL ANIMAL LEVEL

| 26 | 58 | A | 495 | 82  | 0713 | 1038 | 2.0 | 110.69 | 801 | 678 | 24 | 10 | 34 | 6 | 12 |
|----|----|---|-----|-----|------|------|-----|--------|-----|-----|----|----|----|---|----|
| 21 | 58 | A | 495 | 82  | 0713 | 962  | 3.0 | 111.62 | 749 | 678 | 24 | 10 | 34 | 6 | 12 |
| 30 | 58 | A | 495 | 90  | 0721 | 1031 | 3.0 | 112.60 | 798 | 678 | 24 | 10 | 34 | 6 | 12 |
| 29 | 58 | A | 495 | 92  | 0723 | 1097 | 3.0 | 112.39 | 843 | 678 | 24 | 10 | 34 | 6 | 12 |
| 13 | 58 | A | 495 | 94  | 0725 | 1055 | 3.0 | 112.77 | 811 | 678 | 24 | 10 | 34 | 6 | 12 |
| 28 | 58 | A | 495 | 102 | 0802 | 1260 | 2.0 | 113.93 | 965 | 678 | 24 | 10 | 34 | 6 | 12 |
| 34 | 57 | A | 495 | 113 | 0813 | 1260 | 2.0 | 112.65 | 931 | 678 | 24 | 10 | 34 | 6 | 12 |
| 19 | 57 | A | 495 | 115 | 0815 | 1159 | 3.0 | 111.58 | 843 | 678 | 24 | 10 | 34 | 6 | 12 |

|     |     |     |     | ADG | | | Feed intake | | | TREATS/HD | | PROCS/Hd | | TOTALS/Hd | |
|-----|-----|-----|-----|-----|-----|-----|-----|-----|-----|-----|-----|-----|-----|-----|-----|
| TAG | PEN | HGp | LOT | CPD | LPD | ID | PCP | ACP | L7D | ID | Proj | Act | Proj | Act | Proj | TD |
| 25 | 59 | A | 495 | 4.2 | 5.4 | 4.6 | 22 | 26 | 25 | 25 | 1 | .00 | 5 | 4.75 | 6 | 4.75 |
| 11 | 59 | A | 495 | 2.9 | 5.8 | 3.7 | 21 | 27 | 25 | 26 | 1 | .00 | 5 | 4.75 | 6 | 4.75 |
| 15 | 59 | A | 495 | 2.3 | 5.8 | 3.3 | 21 | 26 | 25 | 26 | 1 | .00 | 5 | 4.75 | 6 | 4.75 |
| 4 | 59 | A | 495 | 2.6 | 6.4 | 3.7 | 21 | 29 | 28 | 29 | 1 | .00 | 5 | 4.75 | 6 | 4.75 |
| 3 | 59 | A | 495 | 3.8 | 5.2 | 4.2 | 21 | 25 | 23 | 24 | 1 | .00 | 5 | 4.75 | 6 | 4.75 |
| 18 | 59 | A | 495 | 3.2 | 5.1 | 3.7 | 21 | 24 | 23 | 23 | 1 | .00 | 5 | 4.75 | 6 | 4.75 |
| 14 | 59 | B | 495 | 2.8 | 5.5 | 3.6 | 21 | 26 | 24 | 25 | 1 | .00 | 5 | 4.75 | 6 | 4.75 |
| 22 | 59 | B | 495 | 5.2 | 6.2 | 5.5 | 21 | 31 | 29 | 29 | 1 | .00 | 5 | 4.75 | 6 | 4.75 |
| 5 | 59 | B | 495 | 3.6 | 5.2 | 4.1 | 21 | 25 | 23 | 24 | 1 | .00 | 5 | 4.75 | 6 | 4.75 |
| 17 | 59 | B | 495 | 2.2 | 4.4 | 2.8 | 21 | 20 | 19 | 20 | 1 | .00 | 5 | 4.75 | 6 | 4.75 |
| 9 | 59 | B | 495 | 4.0 | 6.3 | 4.7 | 21 | 30 | 28 | 29 | 1 | .00 | 5 | 4.75 | 6 | 4.75 |
| 2 | 58 | A | 495 | 3.5 | 5.4 | 4.0 | 21 | 26 | 24 | 25 | 1 | .00 | 5 | 4.75 | 6 | 4.75 |
| 16 | 58 | A | 495 | 3.8 | 6.1 | 4.5 | 21 | 29 | 27 | 28 | 1 | .00 | 5 | 4.75 | 6 | 4.75 |
| 20 | 58 | A | 495 | 3.4 | 5.4 | 4.0 | 21 | 26 | 24 | 25 | 1 | .00 | 5 | 4.75 | 6 | 4.75 |
| 23 | 58 | A | 495 | 5.0 | 7.0 | 5.6 | 21 | 34 | 32 | 32 | 1 | .00 | 5 | 4.75 | 6 | 4.75 |
| 24 | 58 | A | 495 | 3.2 | 5.5 | 3.9 | 21 | 26 | 24 | 25 | 1 | .00 | 5 | 4.75 | 6 | 4.75 |
| 26 | 58 | A | 495 | 2.5 | 5.7 | 3.4 | 21 | 26 | 24 | 25 | 1 | .00 | 5 | 4.75 | 6 | 4.75 |
| 21 | 58 | A | 495 | 2.2 | 5.3 | 3.1 | 21 | 24 | 23 | 24 | 1 | .00 | 5 | 4.75 | 6 | 4.75 |
| 30 | 58 | A | 495 | 1.8 | 5.8 | 3.0 | 21 | 26 | 24 | 25 | 1 | .00 | 5 | 4.75 | 6 | 4.75 |
| 29 | 58 | A | 495 | 4.4 | 5.6 | 4.7 | 21 | 27 | 26 | 26 | 1 | .00 | 5 | 4.75 | 6 | 4.75 |
| 13 | 58 | A | 495 | 3.3 | 5.6 | 3.9 | 21 | 26 | 25 | 25 | 1 | .00 | 5 | 4.75 | 6 | 4.75 |
| 28 | 58 | A | 495 | 3.1 | 6.8 | 4.2 | 21 | 31 | 29 | 30 | 1 | .00 | 5 | 4.75 | 6 | 4.75 |
| 34 | 57 | A | 495 | 3.8 | 6.4 | 4.5 | 21 | 30 | 28 | 29 | 1 | .00 | 5 | 4.75 | 6 | 4.75 |
| 19 | 57 | A | 495 | 3.6 | 5.8 | 4.2 | 21 | 27 | 26 | 26 | 1 | .00 | 5 | 4.75 | 6 | 4.75 |

TABLE 3F

Pen Closeout Report
Research-Division
As of Apr, 22, 1994

Lot 495   Pen 59   Owner AGRI   Agri Research Center, Inc.   100.00

| | Pounds | | | Dollars | |
|---|---|---|---|---|---|
| Item | Head | Total | Avg | /CWT | /Head | Total |

INCOME

| Inventory | 10 | 7,867 | 787 | 73.25 | 576.28 | 5,762.80 |

EXPENSES

| Cattle: HEIFERS | 10 | 6,775 | 678 | 76.00 | 514.90 | 5,149.00 |

| Feed and Other: | | | | COG | /Head | Total |
|---|---|---|---|---|---|---|
| FEED CHARGES | | | | 50.15 | 54.77 | 547.60 |
| CATTLE INSURANCE | | | | 0.16 | 0.17 | 1.70 |
| YARDAGE | | | | 1.56 | 1.70 | 17.00 |
| PROCESSING | | | | 4.35 | 4.75 | 47.40 |
| Sub Total Feed and Other | | | | 56.21 | 61.38 | 613.80 |
| Total | | | | | 576.28 | 5,762.80 |
| Profit/Loss | | | | | 0.00 | 0.00 |

[Performance Data]

| Total Pounds Gained | 1,092.00 | Total Proc & Med | 47.45 |
|---|---|---|---|
| /Head | 109.20 | /Head | 4.75 |

Pen Closeout Report
Research-Division
As of Apr, 22, 1994

Lot 495   Pen 59   Owner AGRI   Agri Research Center, Inc.   100.00

| Average Daily Gain | 3.21 | Total Deads | 0.00 |
|---|---|---|---|
| Daily Feed Cost/Head | 1.61 | % Death Loss | 0.00% |
| Daily Total Cost/Head | 1.81 | % Shrink into Yard | 0.00% |
| Total Pounds Fed | 8,040.86 | Total Feed Cost | 547.69 |
| Total Pounds Fed/Head | 804.09 | Avg Ration Cost/Ton | $136.23 |
| Avg Daily Consumption | 23.65 | Cost of Gain | 56.21 |
| Wet Conversion | 7.36 | (Deads In) | |
| Dry Conversion | 6.02 | Cost of Gain | 56.21 |
| In: Mar. 19, 1994   Out: | | (Deads Out) | |
| | | Total Head Days | 340.00 |
| | | Average Days on Feed | 34.00 |

SUMMARY:

10 HEIFERS
In Wt 678 Out Wt 787
Gained 3.21 for 34 DOF
Cost of Gain: 56.21
Profit 0.00(Before Interest)

TABLE 3G

Close-Out Summary
BY LOT

LOT: 42894
PENS: 553  HEAD 27  SEX S  DATE Apr. 28, 1993

TOTAL PFT: $4,957.98

SIRE: ANGUS    DAM: BRAFORD

| VID | PFT | TCOG | ADG | FE | QG | YG | HCW | DP % | LW | PWT | DOF | FCOG | PROC | TREAT | TCOG |
|---|---|---|---|---|---|---|---|---|---|---|---|---|---|---|---|
| 567 | 329.96 | 45.00 | 3.37 | 6.31 | CH− | 4.0 | 875 | 66.5 | 1315 | 634 | 202 | 43.00 | 11.36 | 0.00 | 45.00 |
| 563 | 64.18 | 45.00 | 3.64 | 6.25 | SE+ | 5.0 | 777 | 62.8 | 1238 | 648 | 162 | 42.00 | 11.36 | 0.00 | 45.00 |
| 564 | 76.03 | 57.00 | 2.97 | 7.16 | SE+ | 4.2 | 736 | 61.8 | 1190 | 590 | 202 | 48.00 | 11.36 | 33.25 | 57.00 |
| 565 | 233.46 | 42.00 | 3.93 | 5.79 | SE− | 5.0 | 915 | 66.6 | 1373 | 736 | 162 | 39.00 | 11.36 | 0.00 | 42.00 |
| 566 | 122.80 | 66.00 | 2.47 | 9.20 | SE− | 3.3 | 699 | 65.3 | 1070 | 620 | 182 | 62.00 | 11.36 | 0.00 | 56.00 |
| AVG | 165.29 | 51.00 | 3.28 | 6.94 | | 4.30 | 800 | 65 | 1237 | 646 | 182 | 46.80 | 11.36 | 6.65 | 51.00 |

SIRE: ANGUS    DAM: BRANGUS

| VID | PFT | TCOG | ADG | FE | QG | YG | HCW | DP % | LW | PWT | DOF | FCOG | PROC | TREAT | TCOG |
|---|---|---|---|---|---|---|---|---|---|---|---|---|---|---|---|
| 423 | 151.91 | 39.00 | 3.57 | 5.98 | SE− | 2.9 | 731 | 61.9 | 1181 | 460 | 202 | 36.00 | 11.36 | 0.00 | 39.00 |
| 421 | 296.59 | 40.00 | 3.87 | 5.69 | SE− | 3.9 | 811 | 62.6 | 1296 | 592 | 182 | 38.00 | 11.36 | 0.00 | 40.00 |
| 425 | 74.46 | 63.00 | 2.23 | 9.17 | CH | 3.2 | 661 | 64.7 | 1022 | 508 | 231 | 60.00 | 11.36 | 0.00 | 63.00 |
| 420 | 113.36 | 43.00 | 3.23 | 6.61 | SE+ | 2.7 | 693 | 62.2 | 1114 | 462 | 202 | 40.00 | 11.36 | 0.00 | 43.00 |
| 427 | 282.11 | 45.00 | 3.45 | 6.38 | SE+ | 3.5 | 775 | 64.1 | 1210 | 582 | 182 | 43.00 | 11.36 | 0.00 | 45.00 |
| 422 | 198.62 | 45.00 | 3.06 | 6.97 | CH− | 3.0 | 734 | 64.5 | 1138 | 480 | 215 | 42.00 | 11.36 | 0.00 | 45.00 |
| AVG | 186.18 | 45.83 | 3.24 | 6.80 | 0.00 | 3.20 | 734 | 63 | 1160 | 514 | 202 | 43.17 | 11.36 | 0.00 | 45.83 |

SIRE: ANGUS    DAM: ANGUS

| VID | PFT | TCOG | ADG | FE | QG | YG | HCW | DP % | LW | PWT | DOF | FCOG | PROC | TREAT | TCOG |
|---|---|---|---|---|---|---|---|---|---|---|---|---|---|---|---|
| 619 | 254.93 | 42.75 | 3.25 | 7.60 | CH | 2.3 | 742 | 66.6 | 1114 | 574 | 166 | 38.73 | 10.04 | 0.00 | 42.75 |
| 616 | −129.50 | 58.02 | 2.59 | 9.50 | SE | 3.0 | 701 | 62.9 | 1114 | 558 | 215 | 50.27 | 10.04 | 19.50 | 58.02 |
| 633 | 231.38 | 46.77 | 3.17 | 8.50 | CH | 2.8 | 762 | 63.2 | 1205 | 562 | 203 | 43.17 | 10.04 | 0.00 | 46.77 |
| 628 | 222.01 | 53.51 | 3.08 | 8.60 | CH | 2.7 | 813 | 65.7 | 1238 | 612 | 203 | 45.61 | 10.04 | 25.58 | 53.51 |
| 661 | 255.60 | 43.86 | 3.15 | 7.90 | CH | 3.7 | 822 | 65.3 | 1258 | 660 | 190 | 40.12 | 10.04 | 0.00 | 43.86 |
| 929 | 154.05 | 52.96 | 2.58 | 9.70 | CH | 4.1 | 708 | 63.8 | 1109 | 554 | 215 | 48.81 | 10.04 | 0.00 | 52.96 |
| AVG | 164.75 | 49.65 | 2.97 | 8.63 | 0.00 | 3.10 | 758 | 65 | 1173 | 587 | 199 | 44.45 | 10.04 | 7.51 | 49.65 |

SIRE: ANGUS    DAM: HERF

| VID | PFT | TCOG | ADG | FE | QG | YG | HCW | DP % | LW | PWT | DOF | FCOG | PROC | TREAT | TCOG |
|---|---|---|---|---|---|---|---|---|---|---|---|---|---|---|---|
| 907 | 178.77 | 45.63 | 3.05 | 8.20 | CH | 2.1 | 741 | 64.3 | 1152 | 646 | 166 | 41.34 | 10.04 | 0.00 | 45.63 |
| 908 | 257.39 | 42.53 | 3.60 | 6.80 | CH | 2.4 | 906 | 63.1 | 1435 | 652 | 215 | 36.16 | 10.04 | 25.58 | 42.53 |
| 902 | 266.58 | 42.83 | 3.25 | 7.70 | CH | 2.9 | 811 | 63.7 | 1181 | 642 | 166 | 38.81 | 10.04 | 0.00 | 42.83 |
| 903 | 181.05 | 44.14 | 3.15 | 7.90 | SE | 2.6 | 789 | 64.6 | 1219 | 696 | 166 | 39.99 | 10.04 | 0.00 | 44.14 |
| 906 | 203.41 | 50.74 | 2.74 | 9.00 | CH | 3.1 | 748 | 69.6 | 1075 | 620 | 166 | 45.97 | 10.04 | 0.00 | 50.74 |
| 905 | 183.21 | 42.67 | 3.26 | 7.60 | SE | 2.3 | 768 | 63.7 | 1205 | 664 | 166 | 38.66 | 10.04 | 0.00 | 42.67 |
| 904 | 216.42 | 44.13 | 3.10 | 8.10 | CH | 2.5 | 809 | 63.6 | 1272 | 606 | 215 | 40.68 | 10.04 | 0.00 | 44.13 |
| 910 | 171.61 | 49.23 | 2.78 | 9.00 | CH | 3.0 | 792 | 64.4 | 1229 | 632 | 215 | 45.38 | 10.04 | 0.00 | 49.23 |
| 911 | 172.01 | 50.52 | 2.75 | 9.10 | CH | 1.2 | 686 | 63.2 | 1085 | 628 | 166 | 45.77 | 10.04 | 0.00 | 50.52 |
| 909 | 245.58 | 43.41 | 3.15 | 7.90 | CH | 3.8 | 893 | 65.0 | 1373 | 696 | 215 | 40.01 | 10.04 | 0.00 | 43.41 |
| AVG | 202.6 | 45.583 | 3.083 | 8.13 | 0 | 2.6 | 794 | 65 | 1223 | 649 | 186 | 41.277 | 10.04 | 2.558 | 45.583 |

LOT AVERAGE

| | PFT | TCOG | ADG | FE | QG | YG | HCW | DP % | LW | PWT | DOF | FCOG | PROC | TREAT | TCOG |
|---|---|---|---|---|---|---|---|---|---|---|---|---|---|---|---|
| AVG | 183.63 | 43.34 | 2.61 | 6.42 | | 2.91 | 703 | 59 | 1090 | 548 | 174 | 39.60 | 9.65 | 3.58 | 43.34 |
| STD | | 15.02 | 1.22 | 3.06 | | 1.21 | 230 | 19 | 356 | 185 | 59 | 13.72 | 3.11 | 8.66 | 15.02 |
| MAX | 329.96 | 66.00 | 3.93 | 9.70 | | 5.00 | 915 | 70 | 1435 | 736 | 231 | 62.00 | 11.36 | 33.25 | 66.00 |
| MIN | −129.50 | 39.00 | 2.23 | 5.69 | | 1.20 | 661 | 62 | 1022 | 460 | 162 | 36.00 | 10.04 | 0.00 | 39.00 |
| RANG | 469.46 | 27.00 | 1.70 | 4.01 | | 3.80 | 254 | 8 | 413 | 276 | 69 | 26.00 | 1.32 | 33.25 | 27.00 |

TABLE 4A

Feedlot Business System

Type in the three letters abs to start the Animal Health Program
1. Type EMS
2. TERM = (ANSI) typewy 150
   Feedlot Business System
   Agri Research Database
   ver 4.1
   Mar. 03, 1994
   Enter user ID_____
   Access Micro-System
3. Push the DEL key on the keyboard
4. S Type ECM
   ELECTRONIC CATTLE MANAGEMENT PROGRAM
   0 - Exit
   1 - Perform an ECM Session
   2 - Modify ECM Session Configuration
   3 - Print the Results of an ECM Session
5. Type 1 then press the Enter key
   ELECTRONIC CATTLE MANAGEMENT PROGRAM
   Currently defined Session Types:
   1   2   3   4
   Choose Session Type from above list
6. Type 2 then press the Enter key

TABLE 4B

| | | | |
|---|---|---|---|
| 1 | Session Types: 2 | | |
| 2 | Description: Demo | | |
| 3 | Process control computer present ? | [yes] | |
| 4 | Unused | [no] | |
| 5 | Type of Sorting ? | [AR] | |
| 6 | Read Electronic Ear Tag ? | [yes] | |
| 7 | Insert New Visual Ear Tags ? | [no] | |
| 8 | Cattle Type ? | [not Recorded] | |
| 9 | Frame Type ? | [not Recorded] | |
| 10 | Flesh Type ? | [not Recorded] | |
| 11 | AGE ? | [not Recorded] | |
| 12 | Weight ? | [Automatically] | |
| 13 | Back Fat ? | [Automatically] | |
| 14 | Loin Depth ? | [not Recorded] | |
| 15 | Rump Height ? | [Keyed In] | |
| 16 | Rump Width ? | [not Recorded] | |
| 17 | Shoulder Height ? | [not Recorded] | |
| 18 | Shoulder Width ? | [not Recorded] | |
| 19 | Top Length ? | [not Recorded] | |
| 20 | Body Length ? | [not Recorded] | |
| 21 | Girth ? | [not Recorded] | |

Enter row = to change. 0 to finish or 99 to delete session
7. Type 0 then push the Enter key
   1 - Sort Name: AR
   2 - Description:
   3 - Sorting Criteria ?        [Optimum END Date]
   4 - FLEX sort ?               [yes]
   5 - FLEK pen Number ?         [3]
   6 - Sort Pen Count ?          [3]
   Number to change-or-0 when finished
8. Type 0 then push the Enter key
   Number of head to be sorted in the Session

TABLE 4C

How many Animals should be sorted into each group

| | | |
|---|---|---|
| 1 - Sort Pen | 1 final count ____? | |
| 2 - Sort Pen | 2 final count ____? | |
| 3 - Flex Pen | 3 final count ____? | |
| 4 - SortPen | 4 final count ____? | |

Number to Change-or-0 when finished
9. Type 0 then press Enter key
   ELECTRONIC CATTLE MANAGEMENT PROGRAM

TABLE 4C-continued

| | | Animal ?? of?? | |
|---|---|---|---|
| Lot | Pen | Sort Pen | Head Count |
| EID Tag 0 | | 1 | 0 |
| Frame 0 | | 2 | 0 |
| Weight 0 | | FLEX | 0 |
| Rump Ht. | | 4 | 0 |
| Back fat | | 5 | 0 |
| OED Dec. 31, 1999 | | 6 | 0 |

10. Are these cattle all from the same lot?
11. . . . And what is this Lot?
12. Are these cattle all from the same Pen?
13. . . . And what is this Pen?
14. Enter the Date that sorting occurred (usually today's date)?
    Trying to establish communication with Process Control Computer

TABLE 4D

Process Control Setup

1. Power on computer
   C:ECM>
2. Type ECM
   *ENTER RUN PARAMETERS*
   LOG FILENAME ==
3. Enter today's date 040194
   Sort Types:
   0 - No Sort
   1 - FBS Sort
   2 - Weight
   3 - Days of Feed Sort
   4 - Manual Sort
   Enter Sort Type ==
4. If you Enter 0 go to #9
5. If you Enter 1 go to #16
6. If you Enter 2 go to #17
7. If you Enter 3 go to #37
8. If you Enter 4 go to #60
   Sort Type 0
9. Catch Heads (Y N) ==
10. Squeeze Animals (Y N) ==
11. Weigh Animals (Y N) ==
12. Read Electronic ID (Y N) ==
13. Do Animals already have EID Tags (Y N) ==
14. Read Back fat (Y N) ==
15. Take Video Measurements (Y N) ==
    ECM Computer is Ready to go

TABLE 4E

Sort Type 1

16. Is this a Flex Group Sort (Y N) ==
    If Y the program will start
    If N go to step #9
    Sort Type 2

17. Minimum Weight for Pen 1 ==
18. Maximum Weight for Pen 1 ==
19. Minimum Weight for Pen 2 ==
20. Maximum Weight for Pen 2 ==
21. Minimum Weight for Pen 3 ==
22. Maximum Weight for Pen 3 ==
23. Minimum Weight for Pen 4 ==
24. Maximum Weight for Pen 4 ==
25. Minimum Weight for Pen 5 ==
26. Maximum Weight for Pen 5 ==
27. Minimum Weight for Pen 6 ==
28. Maximum Weight for Pen 6 ==
29. Minimum Weight for Pen 7 ==

TABLE 4E-continued

| | |
|---|---|
| 30. | Maximum Weight for Pen 7 == |
| 31. | Lot Number == |
| 32. | Source Pen Number == |
| 33. | Head Count == |
| 34. | Breed. Frame type == |
| 35. | Average Weight == |
| 36. | Go To #9 |

TABLE 4F

| | |
|---|---|
| 37. | Sort Type 3 |
| 38. | Minimum Weight for Pen 1 == |
| 39. | Maximum Weight for Pen 1 == |
| 40. | Minimum Weight for Pen 2 == |
| 41. | Maximum Weight for Pen 2 == |
| 42. | Minimum Weight for Pen 3 == |
| 43. | Maximum Weight for Pen 3 == |
| 44. | Minimum Weight for Pen 4 == |
| 45. | Maximum Weight for Pen 4 == |
| 46. | Minimum Weight for Pen 5 == |
| 47. | Maximum Weight for Pen 5 == |
| 48. | Minimum Weight for Pen 6 == |
| 49. | Maximum Weight for Pen 6 == |
| 50. | Minimum Weight for Pen 7 == |
| 51. | Maximum Weight for Pen 7 == |
| 52. | Lot Number == |
| 53. | Source Number == |
| 54. | Head Count == |
| 55. | Bread. Frame Type == |
| 56. | Average Weight == |
| 57. | Out Weight == |
| 58. | Average Daily Gain == |
| | Days on Feed??? (calculated by computer) |
| 59. | Go To #9 |
| 60. | Sort Type 4 |
| 61. | Go To #9 |

What is claimed is:

1. A method for tracking animals destined for commercial food production which includes a time period in which groups of animals are fed in pens in feedlots prior to shipment from the feedlot for processing into food products, comprising:
   entering into the computer system identification data for an animal from an electronic identification device for the animal thereby enabling the computer system to identify each animal and distinguish it from every other animal in a group;
   entering into a computer system data relating to individual animals that have been commingled by mixing from different groups of animals and correlating the data with the identification of the individual animals in the computer system;
   entering into the computer system location data for identified individual animals for locations occupied by the identified animals;
   correlating in the computer system the location data for each animal with its identification;
   enabling a user to review a record of the location data for the identified animals;
   determining from data in the computer system locations of an initially identified animal;
   identifying in the computer system a subsequently identified animal which shared a location with the initially identified animal; and
   recycling the identification devices.

2. The method according to claim 1 where identifying comprises identifying all animals which shared a location with the initially identified animal.

3. The method according to claim 1 where entering data comprises initially recording at least two characteristics of identified animals, including a measured weight, and matching in the computer the recorded characteristics with the animal's recorded identification.

4. The method according to claim 3 further comprising:
   feeding identified animals with a group of other animals;
   storing in the computer for the identified animal a limit or target condition;
   making a computer projection of an estimated time or date for the identified animal to achieve the projected limit or target condition based at least in part on the characteristics; and
   selecting identified animals for further processing based at least in part on the estimated time or date.

5. The method according to claim 4 further comprising recording at least two characteristics of identified animals at least a first time and at least a second time, the two characteristics including a measured weight, and matching in the computer the recorded characteristics with the animal's recorded identification.

6. At least one computer readable medium having stored thereon program instructions executable on a computing device to perform the method of claim 1.

* * * * *